United States Patent
Hammerbeck et al.

(10) Patent No.: US 8,221,771 B2
(45) Date of Patent: Jul. 17, 2012

(54) FORMULATIONS CONTAINING AN IMMUNE RESPONSE MODIFIER

(75) Inventors: David M. Hammerbeck, Houlton, WI (US); Cynthia A. Guy, Osseo, MN (US); Suzanne S Leung, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1105 days.

(21) Appl. No.: 10/595,049

(22) PCT Filed: Aug. 5, 2004

(86) PCT No.: PCT/US2004/025277
§ 371 (c)(1),
(2), (4) Date: Jan. 18, 2006

(87) PCT Pub. No.: WO2005/016275
PCT Pub. Date: Feb. 24, 2005

(65) Prior Publication Data
US 2007/0292456 A1 Dec. 20, 2007

Related U.S. Application Data

(60) Provisional application No. 60/493,109, filed on Aug. 5, 2003.

(51) Int. Cl.
*A61K 45/00* (2006.01)

(52) U.S. Cl. .................................................. 424/278.1

(58) Field of Classification Search ................ 424/278.1
See application file for complete search history.

(56) References Cited

U.S. PATENT DOCUMENTS

| | | |
|---|---|---|
| 3,314,941 A | 4/1967 | Littell et al. |
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,164,194 A | 11/1992 | Hettche |
| 5,175,296 A | 12/1992 | Gerster |
| 5,238,944 A | 8/1993 | Wick et al. |
| 5,266,575 A | 11/1993 | Gerster et al. |
| 5,268,376 A | 12/1993 | Gester |
| 5,346,905 A | 9/1994 | Gerster |

(Continued)

FOREIGN PATENT DOCUMENTS

EP 0 394 026 B1 10/1990

(Continued)

OTHER PUBLICATIONS

Kublik et al. ("Nasal delivery systems and their effect on deposition and absorption" in Advanced Drug Delivery Reviews, 29 (1998), pp. 157-177).*

(Continued)

*Primary Examiner* — Blessing Fubara

(57) ABSTRACT

Pharmaceutical formulations in an aqueous (preferably, sprayable) formulation including an immune response modifier (IRM), such as those chosen from imidazoquinoline amines, tetrahydroimidazoquinoline amines, imidazopyridine amines, 6,7-fused cycloalkylimidazopyridine amines, 1,2-bridged imidazoquinoline amines, imidazonaphthyridine amines, imidazotetrahydronaphthyridine amines, oxazoloquinoline amines, thiazoloquinoline amines, oxazolopyridine amines, thiazolopyridine amines, oxazolonaphthyridine amines, thiazolonaphthyridine amines, and 1H-imidazo dimers fused to pyridine amines, quinoline amines, tetrahydroquinoline amines, naphthyridine amines, or tetrahydronaphthyridine amines, are provided. In one embodiment, the aqueous formulations are advantageous for treatment and/or prevention of allergic rhinitis, viral infections, sinusitis, and asthma.

16 Claims, 2 Drawing Sheets

U.S. PATENT DOCUMENTS

| | | | |
|---|---|---|---|
| 5,352,784 | A | 10/1994 | Nikolaides et al. |
| 5,367,076 | A | 11/1994 | Gerster |
| 5,389,640 | A | 2/1995 | Gerster et al. |
| 5,395,937 | A | 3/1995 | Nikolaides et al. |
| 5,446,153 | A | 8/1995 | Lindstrom et al. |
| 5,482,936 | A | 1/1996 | Lindstrom |
| 5,693,811 | A | 12/1997 | Lindstrom |
| 5,741,908 | A | 4/1998 | Gerster et al. |
| 5,756,747 | A | 5/1998 | Gerster |
| 5,939,090 | A | 8/1999 | Beaurline et al. |
| 6,039,969 | A | 3/2000 | Tomai et al. |
| 6,069,149 | A | 5/2000 | Nanba et al. |
| 6,083,505 | A * | 7/2000 | Miller et al. ............... 424/193.1 |
| 6,110,929 | A | 8/2000 | Gerster et al. |
| 6,194,425 | B1 | 2/2001 | Gerster et al. |
| 6,245,776 | B1 * | 6/2001 | Skwierczynski et al. ..... 514/293 |
| 6,331,539 | B1 * | 12/2001 | Crooks et al. .............. 514/228.5 |
| 6,376,669 | B1 | 4/2002 | Rice et al. |
| 6,451,810 | B1 | 9/2002 | Coleman et al. |
| 6,518,265 | B1 | 2/2003 | Kato et al. |
| 6,525,064 | B1 | 2/2003 | Dellaria et al. |
| 6,541,485 | B1 | 4/2003 | Crooks et al. |
| 6,545,016 | B1 | 4/2003 | Dellaria et al. |
| 6,545,017 | B1 | 4/2003 | Dellaria et al. |
| 6,558,951 | B1 | 5/2003 | Tomai et al. |
| 6,573,273 | B1 | 6/2003 | Crooks et al. |
| 6,647,980 | B1 * | 11/2003 | Gizurarson ............... 128/200.14 |
| 6,656,938 | B2 | 12/2003 | Crooks et al. |
| 6,660,735 | B2 | 12/2003 | Crooks et al. |
| 6,660,747 | B2 | 12/2003 | Crooks et al. |
| 6,664,260 | B2 | 12/2003 | Charles et al. |
| 6,664,264 | B2 | 12/2003 | Dellaria et al. |
| 6,664,265 | B2 | 12/2003 | Crooks et al. |
| 6,667,312 | B2 | 12/2003 | Bonk et al. |
| 6,670,372 | B2 | 12/2003 | Charles et al. |
| 6,677,347 | B2 | 1/2004 | Crooks et al. |
| 6,677,348 | B2 | 1/2004 | Heppner et al. |
| 6,677,349 | B1 * | 1/2004 | Griesgraber ................. 514/293 |
| 6,683,088 | B2 | 1/2004 | Crooks et al. |
| 6,706,728 | B2 * | 3/2004 | Hedenstrom et al. ......... 514/293 |
| 6,743,920 | B2 | 6/2004 | Lindstrom et al. |
| 6,756,382 | B2 | 6/2004 | Coleman et al. |
| 6,797,718 | B2 | 9/2004 | Dellaria et al. |
| 6,818,650 | B2 | 11/2004 | Griesgraber |
| 7,923,560 | B2 * | 4/2011 | Wightman et al. ............. 546/82 |
| 2002/0016332 | A1 | 2/2002 | Slade |
| 2002/0055517 | A1 | 5/2002 | Smith |
| 2002/0110840 | A1 | 8/2002 | Tomai et al. |
| 2003/0100764 | A1 | 5/2003 | Bonk et al. |
| 2003/0130299 | A1 | 7/2003 | Crooks et al. |
| 2003/0133913 | A1 | 7/2003 | Tomai et al. |
| 2003/0139364 | A1 | 7/2003 | Krieg et al. |
| 2003/0144283 | A1 | 7/2003 | Coleman et al. |
| 2003/0161797 | A1 | 8/2003 | Miller et al. |
| 2003/0199538 | A1 | 10/2003 | Skwierczynski et al. |
| 2004/0014779 | A1 | 1/2004 | Gorden et al. |
| 2004/0091491 | A1 | 5/2004 | Kedl et al. |
| 2004/0132079 | A1 | 7/2004 | Gupta et al. |
| 2004/0141950 | A1 | 7/2004 | Noelle et al. |
| 2004/0147543 | A1 | 7/2004 | Hays et al. |
| 2004/0162309 | A1 | 8/2004 | Gorden et al. |
| 2004/0171086 | A1 | 9/2004 | Fink et al. |
| 2004/0175336 | A1 | 9/2004 | Egging et al. |
| 2004/0176367 | A1 | 9/2004 | Griesgraber et al. |
| 2004/0180919 | A1 | 9/2004 | Miller et al. |
| 2004/0181130 | A1 | 9/2004 | Miller et al. |
| 2004/0181211 | A1 | 9/2004 | Graham et al. |
| 2004/0191833 | A1 | 9/2004 | Fink et al. |
| 2004/0192585 | A1 | 9/2004 | Owens et al. |
| 2004/0197865 | A1 | 10/2004 | Gupta et al. |
| 2004/0202720 | A1 | 10/2004 | Wightman et al. |
| 2004/0214851 | A1 | 10/2004 | Birmachu et al. |

FOREIGN PATENT DOCUMENTS

| | | |
|---|---|---|
| EP | 1 104 764 A1 | 6/2001 |
| JP | 61-106509 | 5/1986 |
| JP | 9-208584 | 8/1997 |
| JP | 9-255926 | 3/1999 |
| JP | 11-222432 | 8/1999 |
| JP | 2000-247884 | 9/2000 |
| WO | WO 98/17279 A1 | 4/1998 |
| WO | WO 99/01229 | 1/1999 |
| WO | WO 00/76519 | 12/2000 |
| WO | WO 02/36592 | 5/2002 |
| WO | WO 03/045391 A1 | 6/2003 |
| WO | WO 03/097641 | 11/2003 |
| WO | WO 2004/058759 A1 | 7/2004 |
| WO | WO 2005/020999 | 3/2005 |
| WO | WO 2005/032484 | 4/2005 |
| WO | WO 2005/051317 | 6/2005 |
| WO | WO 2005/076783 | 8/2005 |
| WO | WO 2005/094531 | 10/2005 |

OTHER PUBLICATIONS

Bachman et al., "Synthesis of Substituted Quinolylamines. Derivatives of 4-Amino-7-Chloroquinoline," *J. Org. Chem.*, 15, pp. 1278-1284 (1950).

Baranov et al., *Chem. Abs.*, 85, 94362 (1976).

Berenyi et al., "Ring Transformation of Condensed Dihydro-as-triazines," *J. Heterocyclic Chem.*, 18, pp. 1537-1540 (1981).

Brennan et al., "Automated Bioassay of Interferons in Micro-test Plates," *Biotechniques*, Jun./Jul., 78, 1983.

Burleson, "Influenza Virus Host Resistance Model for Assessment of Immunotoxicity, Immunostimulaion, and Antiviral Compounds," Methods in Immunology 2: 181-202, Wiley-Liss Inc., (1995).

Chollet et al., "Development of a Topically Active Imiquimod Formulation," *Pharmaceutical Development and Technology*, 4(1), pp. 35-43 (1999).

Encyclopedia of Pharmaceutical Technology, Second Edition, 856-860, Marcel Dekker, Inc., 2002.

Izumi et al., "1*H*-Imidazo[4,5-*c*]quinoline Derivatives as Novel Potent TNF-α Suppressors: Synthesis and Structure-Activity Relationship of 1-, 2- and 4-Substituted 1*H*-imidazo[4,5-*c*]pyridines," *Bioorganic & Medicinal Chemistry*, 11, pp. 2541-2550 (2003).

Jahnsen et al. "Extensive recruitment of IL-3Rx high Dendritic-cell Precursors to Allergic Nasal Mucosa During Allergen Challenge," Immunology Letters, vol. 69, Issue 1, 32.2, p. 123, Jun. 15, 1999 (abstracts available online Jul. 9, 1999).

Jain et al., "Chemical and Pharmacological Investigations of Some ω-Substituted Alkylamino-3-aminopyridines," *J. Med. Chem.*, 11, pp. 87-92 (1968).

Lehner et al., "The Role of γδ Cells and β-Chemokines in Mucosal Protection Against SIV Infection," Immunology Letters, vol. 69, Issue 1, 2.1, p. 25, Jun. 15, 1999 (abstracts available online Jul. 9, 1999).

Litt et al., "Mucosal Delivery of Vaccine Antigens Displayed on the Surface of *Lactococcus lactis*," Immunology Letters, vol. 69, Issue 1, 11.26, p. 61, Jun. 15, 1999 (abstracts available online Jul. 9, 1999).

Moldoveanu et al, "Poly-L-lysine as a Potential Mucosal Adjuvant," Immunology Letters, vol. 69, Issue 1, 11.28, p. 62, Jun. 15, 1999 (abstracts available online Jul. 9, 1999).

Poljakovic et al. "iNOS and COX-2 Immunoreactivity in the Mice Bladder and Kidney After Bacterial Instillation," Immunology Letters, vol. 69, Issue 1, 31.05, p. 122, Jun. 15, 1999 (abstracts available online Jul. 9, 1999).

Testerman et al., "Cytokine Induction by the Immunomodulators Imiquimod and S-27609," Journal of Leukocyte Biology, vol. 58, pp. 365-372 (Sep. 1995).

Wozniak et al., "The Animation of 3-nitro-1, 5-naphthyridines by Liquid Ammonia/Potassium Permanganate [1,2]. A New and Convenient Amination Method." *Journal of the Royal Netherlands Chemical Society*, pp. 511-513 (Dec. 13, 1983).

Supplementary European Search Report mailed Jun. 17, 2009 for Application No. 04780166.7.

Anonymous: "Aqueous cream" Retrieved from the internet: URL:http://en.wikipedia.org/wiki/Aqueous_cream [retrieved on Sep. 15, 2010].

* cited by examiner

FORMULATIONS CONTAINING AN IMMUNE RESPONSE MODIFIER

CROSS-REFERENCE TO RELATED APPLICATIONS

This application is a 371 of PCT/US04/25277 filed Aug. 5, 2004 and which claims priority to U.S. Provisional Application Ser. No. 60/493,109, filed Aug. 5, 2003, which is incorporated herein by reference in its entirety.

FIELD OF THE INVENTION

The present invention is directed to pharmaceutical formulations that include at least one immune response modifier, such as those chosen from imidazoquinoline amines, tetrahydroimidazoquinoline amines, imidazopyridine amines, 6,7-fused cycloalkylimidazopyridine amines, 1,2-bridged imidazoquinoline amines, thiazoloquinoline amines, oxazoloquinoline amines, thiazolopyridine amines, oxazolopyridine amines, imidazonaphthyridine amines, imidazotetrahydronaphthyridine amines, and thiazolonaphthyridine amines, for example. Embodiments of the present invention are directed to aqueous (preferably sprayable) solutions. Other embodiments of the present invention are directed to various methods of use of the aqueous formulations.

BACKGROUND

Many imidazoquinoline amine, imidazopyridine amine, 6,7-fused cycloalkylimidazopyridine amine, 1,2-bridged imidazoquinoline amine, thiazoloquinoline amine, oxazoloquinoline amine, thiazolopyridine amine, oxazolopyridine amine, imidazonaphthyridine amine, imidazotetrahydronaphthyridine amine, and thiazolonaphthyridine amine compounds have demonstrated potent immunostimulating, antiviral and antitumor (including anticancer) activity, and have also been shown to be useful as vaccine adjuvants and treatment of TH2-mediated diseases. These compounds are hereinafter collectively referred to as "IRM" (immune response modifier) compounds.

The mechanism for the immunostimulatory activity of these IRM compounds is thought to be due in substantial part to enhancement of the immune response by induction of various important cytokines (e.g., interferons, interleukins, tumor necrosis factor, etc.). Such compounds have been shown to stimulate a rapid release of certain monocyte/macrophage-derived cytokines and are also capable of stimulating B cells to secrete antibodies, which play an important role in these IRM compounds' activities. One of the predominant immunostimulating responses to these compounds is the induction of interferon (IFN)-$\alpha$ production, which is believed to be very important in the acute antiviral and antitumor activities seen. Moreover, up regulation of other cytokines such as, for example, tumor necrosis factor (TNF), Interleukin-1 (IL-1), IL-6, and IL-12 also have potentially beneficial activities and are believed to contribute to the antiviral and antitumor properties of these compounds.

Although some of the beneficial effects of IRMs are known, the ability to provide therapeutic benefit via topical application of an IRM compound for treatment of a particular condition at a particular location may be hindered by a variety of factors. These factors include irritation of the dermal or mucosal surface to which the formulation is applied, ciliary clearance of the formulation, formulation wash away, insolubility and/or degradation of the IRM compound in the formulation, physical instability of the formulation (e.g., separation of components, thickening, precipitation/agglomerization of active ingredient, and the like), and poor permeation, for example. Accordingly, there is a continuing need for new methods and formulations to provide the greatest therapeutic benefit from this class of compounds.

SUMMARY

The present invention is directed to aqueous formulations and methods of use. Preferably, such formulations are sprayable. Such formulations include: an immune response modifier; water; and a hydrophilic viscosity enhancing agent; with the proviso that the hydrophilic viscosity enhancing agent is not covalently bonded to the immune response modifier; wherein the formulation is a solution at room temperature and has a viscosity of less than 100 Centipoise (cps) at room temperature. Formulations of the present invention can provide desirable vehicles for immune response modifier compounds and can allow for easier manufacture and increased residence time of the immune response modifier, particularly on mucosal tissue.

In another embodiment, the present invention provides an aqueous sprayable formulation that includes: an immune response modifier selected from the group consisting of imidazoquinoline amines, tetrahydroimidazoquinoline amines, imidazopyridine amines, 6,7-fused cycloalkylimidazopyridine amines, 1,2-bridged imidazoquinoline amines, imidazonaphthyridine amines, imidazotetrahydronaphthyridine amines, oxazoloquinoline amines, thiazoloquinoline amines, oxazolopyridine amines, thiazolopyridine amines, oxazolonaphthyridine amines, thiazolonaphthyridine amines, 1H-imidazo dimers fused to pyridine amines, quinoline amines, tetrahydroquinoline amines, naphthyridine amines, or tetrahydronaphthyridine amines, and combinations thereof; water; and a hydrophilic viscosity enhancing agent selected from the group consisting of cellulose ethers, polysaccharide gums, acrylic acid polymers, and combinations thereof; with the proviso that the hydrophilic viscosity enhancing agent is not covalently bonded to the immune response modifier; wherein the formulation is a solution at room temperature and has a viscosity of less than 100 cps at room temperature.

The present invention also provides methods of using the formulations of the present invention. In one embodiment, the present invention provides a method for delivering an immune response modifier to a nasal passage of a subject. The method includes: selecting a formulation that includes: an immune response modifier; water; and a hydrophilic viscosity enhancing agent; with the proviso that the hydrophilic viscosity enhancing agent is not covalently bonded to the immune response modifier; wherein the formulation is a solution at room temperature and has a viscosity of less than 100 cps at room temperature; and applying the selected formulation into a nasal passage.

Other methods of the present invention are directed to methods of treating and/or preventing allergic rhinitis by applying (e.g., spraying) a formulation of the present invention into a nasal passage of a subject (typically, an animal, preferably, a mammal, and more preferably, a human). Other methods of the present invention are directed to methods of treating and/or preventing a viral infection by applying (e.g., spraying) a formulation of the present invention into a nasal passage of a subject (typically, an animal, preferably, a mammal, and more preferably, a human). Other methods of the present invention are directed to methods of treating and/or preventing sinusitis by applying (e.g., spraying) a formulation of the present invention into a nasal passage of a subject (typically, an animal, preferably, a mammal, and more preferably, a human). Other methods of the present invention are directed to methods of treating and/or preventing asthma by applying (e.g., spraying) a formulation of the present invention into the respiratory tract of a subject (typically, an animal, preferably, a mammal, and more preferably, a human).

The present invention also provides a method of desensitizing a subject to an antigen. The method involves administering to the subject an IRM compound in a formulation of the present invention, after the subject has been sensitized to the antigen, in an amount effective to desensitize the subject to the antigen. Preferably, the IRM compound is administered to the subject at least four hours prior to re-exposure of the subject to the antigen.

The term "solution" refers to a combination of two or more substances uniformly dispersed throughout a single phase, so that the combination is homogeneous at the molecular or ionic level.

The terms "comprises" and variations thereof do not have a limiting meaning where these terms appear in the description and claims.

As used herein, "a," "an," "the," "at least one," and "one or more" are used interchangeably. Thus, for example, an aqueous formulation that comprises "an" immune response modifier can be interpreted to mean that the formulation includes "one or more" immune response modifiers. Similarly, a formulation comprising "a" hydrophilic viscosity enhancing agent can be interpreted to mean that the formulation includes "one or more" hydrophilic viscosity enhancing agents.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
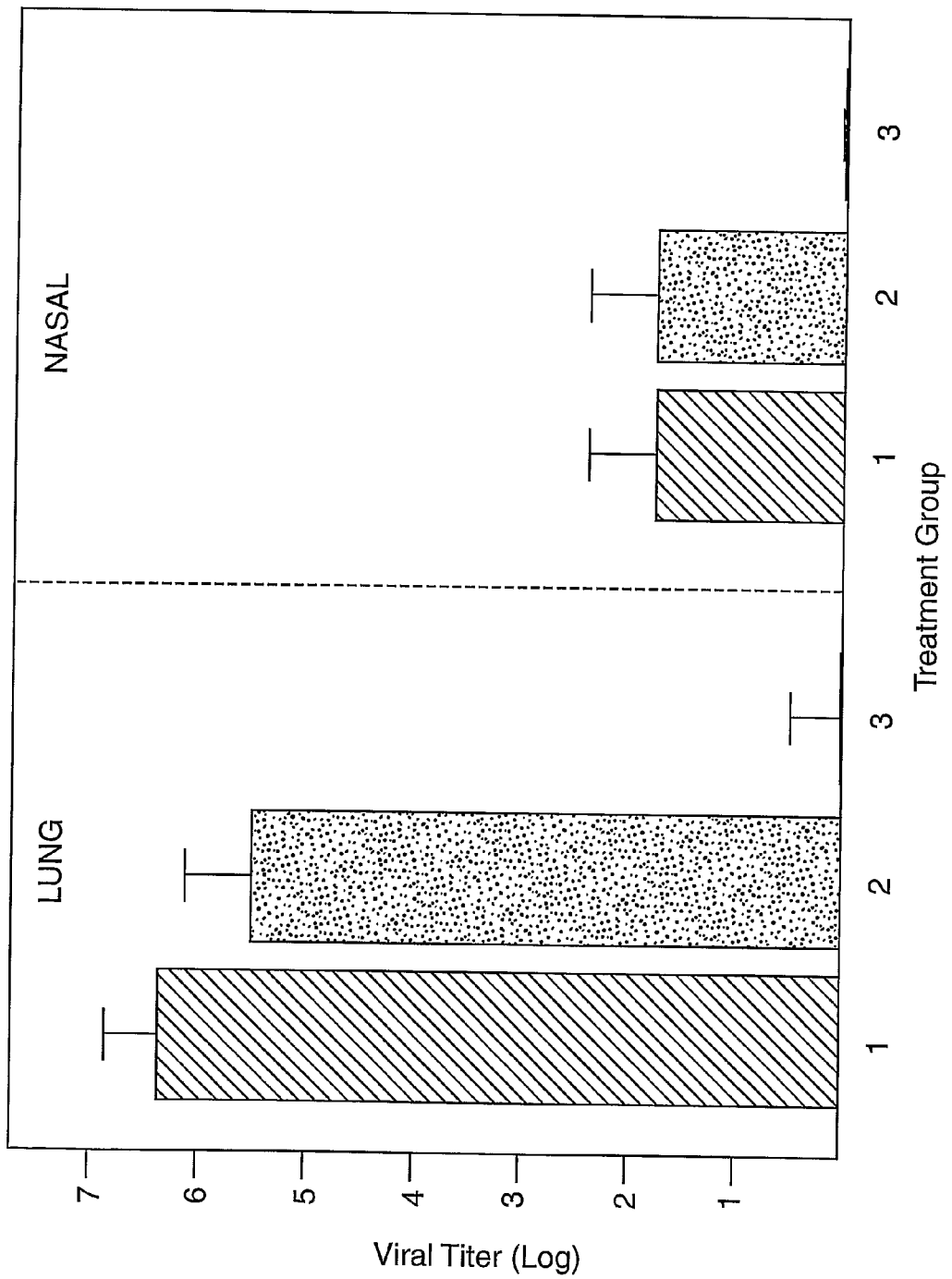
FIG. 1 is a bar graph comparing viral titers in rats after treatment with vehicle, IFN-α, or IRM compound four hours before viral challenge.

The present invention provides aqueous (preferably, sprayable) formulations and methods of use. Such formulations include: an immune response modifier (IRM); water; and a hydrophilic viscosity enhancing agent; with the proviso that the hydrophilic viscosity enhancing agent is not covalently bonded to the immune response modifier; wherein the formulation is a solution at room temperature and has a viscosity of less than 100 cps at room temperature.

Such formulations are in solution form at room temperature (i.e., 25° C.-30° C.). That is, the formulations include two or more substances uniformly dispersed throughout a single phase, so that the combination is homogeneous at the molecular or ionic level. Also, such formulations are sufficiently low in viscosity (less than 100 centipoise (cps)) at room temperature. At such low viscosity level, the compositions are typically and preferably sprayable. In this context, "sprayable" means the formulation can be delivered using a conventional pump spray device, such as those described in *Encyclopedia of Pharmaceutical Technology*, Second Edition, 856-860, Marcel Dekker, Inc., 2002.

Although preferred formulations are sprayable solutions, they do not have to be administered to a subject by spraying. That is, formulations of the present invention can be administered to a subject (e.g., mammal, particularly a human) in various ways by spraying, injection, inhalation, etc. They can be administered, for example, intranasally, intraperitoneally, topically, orally, intratracheally via inhalation (e.g., from a nebulizer or spray pump atomizer), or subcutaneously.

Preferably, formulations of the present invention are administered intranasally by spraying into the nasal passages of a mammal. Depending on the particular IRM compound, IRM compound concentration, and formulation composition, the therapeutic effect of the IRM compound may extend only to the superficial layers of the nasal passages or to tissues below the surface. In some embodiments, the above-described formulations are particularly advantageous for application for a period of time sufficient to obtain a desired therapeutic effect without undesired systemic absorption of the IRM.

In certain embodiments the immune response modifier is a positively charged immune response modifier. Analogously, in certain embodiments, the hydrophilic viscosity enhancing agent is negatively charged.

IRM Compounds

Preferred IRM compounds suitable for use in the formulations of the invention preferably include compounds having a 2-aminopyridine fused to a five membered nitrogen-containing heterocyclic ring. Other small organic molecules known to function as IRM compounds are also suitable for use in the formulations of the invention.

Certain IRMs are small organic molecules (e.g., molecular weight under about 1000 Daltons, preferably under about 500 Daltons, as opposed to large biologic protein, peptides, and the like) such as those disclosed in, for example, U.S. Pat. Nos. 4,689,338; 4,929,624; 4,988,815; 5,037,986; 5,175,296; 5,238,944; 5,266,575; 5,268,376; 5,346,905; 5,352,784; 5,367,076; 5,389,640; 5,395,937; 5,446,153; 5,482,936; 5,693,811; 5,741,908; 5,756,747; 5,939,090; 6,039,969; 6,083,505; 6,110,929; 6,194,425; 6,245,776; 6,331,539; 6,376,669; 6,451,810; 6,525,064; 6,545,016; 6,545,017; 6,558,951; 6,573,273; 6,656,938; 6,660,735; 6,660,747; 6,664,260; 6,664,264; 6,664,265; 6,667,312; 6,670,372; 6,677,347; 6,677,348; 6,677,349; 6,683,088; 6,756,382; European Patent 0 394 026; U.S. Patent Publication Nos. 2002/0016332; 2002/0055517; 2002/0110840; 2003/0133913; 2003/0199538; and 2004/0014779; and International Patent Publication No. WO 04/058759.

IRM compounds suitable for use in the invention preferably include compounds having a 2-aminopyridine fused to a five membered nitrogen-containing heterocyclic ring. Such compounds include, for example, imidazoquinoline amines, including but not limited to, substituted imidazoquinoline amines such as, for example, amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, and 6-, 7-, 8-, or 9-aryl or heteroaryl substituted imidazoquinoline amines; tetrahydroimidazoquinoline amines, including but not limited to, amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, and thioether substituted tetrahydroimidazoquinoline amines; imidazopyridine amines, including but not limited to, amide substituted imidazopyridine amines, sulfonamide substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; imidazotetrahydronaphthyridine amines; oxazoloquinoline amines; thiazoloquinoline amines; oxazolopyridine amines; thiazolopyridine amines; oxazolonaphthyridine amines; thiazolonaphthyridine amines; and 1H-imidazo dimers fused to pyridine amines, quinoline amines, tetrahydroquinoline amines, naphthyridine amines, or tetrahydronaphthyridine amines.

Exemplary IRM Compounds

In certain embodiments of the present invention the IRM compound can be chosen from 1H-imidazo[4,5-c]quinolin-4-amines defined by one of Formulas I-V below:

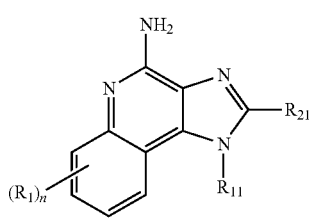

I wherein $R_{11}$ is selected from alkyl of one to ten carbon atoms, hydroxyalkyl of one to six carbon atoms, acyloxyalkyl wherein the acyloxy moiety is alkanoyloxy of two to four carbon atoms or benzoyloxy, and the alkyl moiety contains one to six carbon atoms, benzyl, (phenyl)ethyl and phenyl, said benzyl, (phenyl)ethyl or phenyl substituent being optionally substituted on the benzene ring by one or two moieties independently selected from alkyl of one to four carbon atoms, alkoxy of one to four carbon atoms and halogen, with the proviso that if said benzene ring is substituted by two of said moieties, then said moieties together contain no more than six carbon atoms;

$R_{21}$ is selected from hydrogen, alkyl of one to eight carbon atoms, benzyl, (phenyl)ethyl and phenyl, the benzyl, (phenyl)ethyl or phenyl substituent being optionally substituted on the benzene ring by one or two moieties independently selected from alkyl of one to four carbon atoms, alkoxy of one to four carbon atoms and halogen, with the proviso that when the benzene ring is substituted by two of said moieties, then the moieties together contain no more than six carbon atoms; and each $R_1$ is independently selected from alkoxy of one to four carbon atoms, halogen, and alkyl of one to four carbon atoms, and n is an integer from 0 to 2, with the proviso that if n is 2, then said $R_1$ groups together contain no more than six carbon atoms;

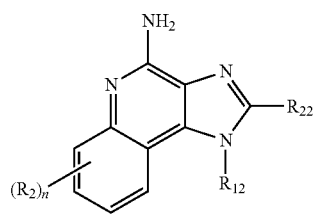

II wherein $R_{12}$ is selected from straight chain or branched chain alkenyl containing two to ten carbon atoms and substituted straight chain or branched chain alkenyl containing two to ten carbon atoms, wherein the substituent is selected from straight chain or branched chain alkyl containing one to four carbon atoms and cycloalkyl containing three to six carbon atoms; and cycloalkyl containing three to six carbon atoms substituted by straight chain or branched chain alkyl containing one to four carbon atoms; and $R_{22}$ is selected from hydrogen, straight chain or branched chain alkyl containing one to eight carbon atoms, benzyl, (phenyl)ethyl and phenyl, the benzyl, (phenyl)ethyl or phenyl substituent being optionally substituted on the benzene ring by one or two moieties independently selected from straight chain or branched chain alkyl containing one to four carbon atoms, straight chain or branched chain alkoxy containing one to four carbon atoms, and halogen, with the proviso that when the benzene ring is substituted by two such moieties, then the moieties together contain no more than six carbon atoms; and each $R_2$ is independently selected from straight chain or branched chain alkoxy containing one to four carbon atoms, halogen, and straight chain or branched chain alkyl containing one to four carbon atoms, and n is an integer from zero to 2, with the proviso that if n is 2, then said $R_2$ groups together contain no more than six carbon atoms;

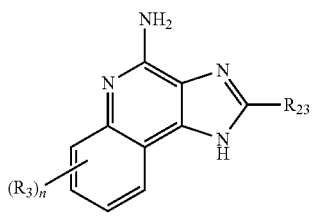

III wherein $R_{23}$ is selected from hydrogen, straight chain or branched chain alkyl of one to eight carbon atoms, benzyl, (phenyl)ethyl and phenyl, the benzyl, (phenyl)ethyl or phenyl substituent being optionally substituted on the benzene ring by one or two moieties independently selected from straight chain or branched chain alkyl of one to four carbon atoms, straight chain or branched chain alkoxy of one to four carbon atoms, and halogen, with the proviso that when the benzene ring is substituted by two such moieties, then the moieties together contain no more than six carbon atoms; and each $R_3$ is independently selected from straight chain or branched chain alkoxy of one to four carbon atoms, halogen, and straight chain or branched chain alkyl of one to four carbon atoms, and n is an integer from zero to 2, with the proviso that if n is 2, then said $R_3$ groups together contain no more than six carbon atoms;

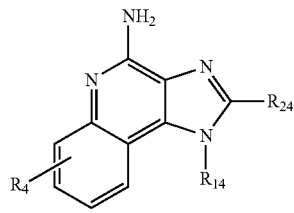

wherein $R_{14}$ is —$CHR_xR_y$, wherein $R_y$ is hydrogen or a carbon-carbon bond, with the proviso that when $R_y$ is hydrogen $R_x$ is alkoxy of one to four carbon atoms, hydroxyalkoxy of one to four carbon atoms, 1-alkynyl of two to ten carbon atoms, tetrahydropyranyl, alkoxyalkyl wherein the alkoxy moiety contains one to four carbon atoms and the alkyl moiety contains one to four carbon atoms, or 2-, 3-, or 4-pyridyl, and with the further proviso that when $R_y$ is a carbon-carbon bond $R_y$ and $R_x$ together form a tetrahydrofuranyl group optionally substituted with one or more substituents independently selected from hydroxy and hydroxyalkyl of one to four carbon atoms;

$R_{24}$ is selected from hydrogen, alkyl of one to four carbon atoms, phenyl, and substituted phenyl wherein the substituent is selected from alkyl of one to four carbon atoms, alkoxy of one to four carbon atoms, and halogen; and $R_4$ is selected from hydrogen, straight chain or branched chain alkoxy containing one to four carbon atoms, halogen, and straight chain or branched chain alkyl containing one to four carbon atoms;

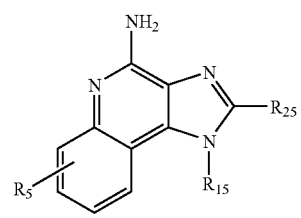

wherein $R_{15}$ is selected from hydrogen; straight chain or branched chain alkyl containing one to ten carbon atoms and substituted straight chain or branched chain alkyl containing one to ten carbon atoms, wherein the substituent is selected from cycloalkyl containing three to six carbon atoms and cycloalkyl containing three to six carbon atoms substituted by straight chain or branched chain alkyl containing one to four carbon atoms; straight chain or branched chain alkenyl containing two to ten carbon atoms and substituted straight chain or branched chain alkenyl containing two to ten carbon atoms, wherein the substituent is selected from cycloalkyl containing three to six carbon atoms and cycloalkyl containing three to six carbon atoms substituted by straight chain or branched chain alkyl containing one to four carbon atoms; hydroxyalkyl of one to six carbon atoms; alkoxyalkyl wherein the alkoxy moiety contains one to four carbon atoms and the alkyl moiety contains one to six carbon atoms; acyloxyalkyl wherein the acyloxy moiety is alkanoyloxy of two to four carbon atoms or benzoyloxy, and the alkyl moiety contains one to six carbon atoms; benzyl; (phenyl)ethyl; and phenyl; said benzyl, (phenyl)ethyl or phenyl substituent being optionally substituted on the benzene ring by one or two moieties independently selected from alkyl of one to four carbon atoms, alkoxy of one to four carbon atoms, and halogen, with the proviso that when said benzene ring is substituted by two of said moieties, then the moieties together contain no more than six carbon atoms;

$R_{25}$ is

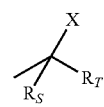

wherein $R_S$ and $R_T$ are independently selected from hydrogen, alkyl of one to four carbon atoms, phenyl, and substituted phenyl wherein the substituent is selected from alkyl of one to four carbon atoms, alkoxy of one to four carbon atoms, and halogen;

X is selected from alkoxy containing one to four carbon atoms, alkoxyalkyl wherein the alkoxy moiety contains one to four carbon atoms and the alkyl moiety contains one to four carbon atoms, hydroxyalkyl of one to four carbon atoms, haloalkyl of one to four carbon atoms, alkylamido wherein the alkyl group contains one to four carbon atoms, amino, substituted amino wherein the substituent is alkyl or hydroxyalkyl of one to four carbon atoms, azido, chloro, hydroxy, 1-morpholino, 1-pyrrolidino, alkylthio of one to four carbon atoms; and $R_5$ is selected from hydrogen, straight chain or branched chain alkoxy containing one to four carbon atoms, halogen, and straight chain or branched chain alkyl containing one to four carbon atoms;

and pharmaceutically acceptable salts of any of the foregoing.

In another embodiment, the IRM compound can be chosen from 6,7 fused cycloalkylimidazopyridine amines defined by Formula VI below:

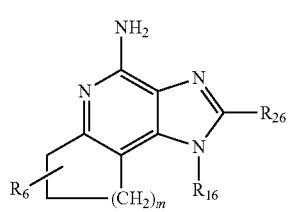

wherein m is 1, 2, or 3;

$R_{16}$ is selected from hydrogen; cyclic alkyl of three, four, or five carbon atoms; straight chain or branched chain alkyl containing one to ten carbon atoms and substituted straight chain or branched chain alkyl containing one to ten carbon atoms, wherein the substituent is selected from cycloalkyl containing three to six carbon atoms and cycloalkyl containing three to six carbon atoms substituted by straight chain or branched chain alkyl containing one to four carbon atoms; fluoro- or chloroalkyl containing from one to ten carbon atoms and one or more fluorine or chlorine atoms; straight chain or branched chain alkenyl containing two to ten carbon atoms and substituted straight chain or branched chain alkenyl containing two to ten carbon atoms, wherein the substituent is selected from cycloalkyl containing three to six carbon atoms and cycloalkyl containing three to six carbon atoms substituted by straight chain or branched chain alkyl containing one to four carbon atoms; hydroxyalkyl of one to six carbon atoms; alkoxyalkyl wherein the alkoxy moiety contains one to four carbon atoms and the alkyl moiety contains one to six carbon atoms; acyloxyalkyl wherein the acyloxy moiety is alkanoyloxy of two to four carbon atoms or benzoyloxy, and the alkyl moiety contains one to six carbon atoms, with the proviso that any such alkyl, substituted alkyl, alkenyl, substituted alkenyl, hydroxyalkyl, alkoxyalkyl, or acyloxyalkyl group does not have a fully carbon substituted carbon atom bonded directly to the nitrogen atom; benzyl; (phenyl)ethyl; and phenyl; said benzyl, (phenyl)ethyl or phenyl substituent being optionally substituted on the benzene ring by one or two moieties independently selected from alkyl of one to four carbon atoms, alkoxy of one to four carbon atoms, and halogen, with the proviso that when said benzene ring is substituted by two of said moieties, then the moieties together contain no more than six carbon atoms; and —CHR$_x$R$_y$, wherein R$_y$ is hydrogen or a carbon-carbon bond, with the proviso that when R$_y$ is hydrogen R$_x$ is alkoxy of one to four carbon atoms, hydroxyalkoxy of one to four carbon atoms, 1-alkynyl of two to ten carbon atoms, tetrahydropyranyl, alkoxyalkyl wherein the alkoxy moiety contains one to four carbon atoms and the alkyl moiety contains one to four carbon atoms, 2-, 3-, or 4-pyridyl, and with the further proviso that when R$_y$ is a carbon-carbon bond R$_y$ and R$_x$ together form a tetrahydrofuranyl group optionally substituted with one or more substituents independently selected from hydroxy and hydroxyalkyl of one to four carbon atoms;

R$_{26}$ is selected from hydrogen; straight chain or branched chain alkyl containing one to eight carbon atoms; straight chain or branched chain hydroxyalkyl containing one to six carbon atoms; morpholinoalkyl; benzyl; (phenyl)ethyl; and phenyl, the benzyl, (phenyl)ethyl, or phenyl substituent being optionally substituted on the benzene ring by a moiety selected from methyl, methoxy, and halogen; and —C(R$_S$)(R$_T$)(X) wherein R$_S$ and R$_T$ are independently selected from hydrogen, alkyl of one to four carbon atoms, phenyl, and substituted phenyl wherein the substituent is selected from alkyl of one to four carbon atoms, alkoxy of one to four carbon atoms, and halogen;

X is selected from alkoxy containing one to four carbon atoms, alkoxyalkyl wherein the alkoxy moiety contains one to four carbon atoms and the alkyl moiety contains one to four carbon atoms, haloalkyl of one to four carbon atoms, alkylamido wherein the alkyl group contains one to four carbon atoms, amino, substituted amino wherein the substituent is alkyl or hydroxyalkyl of one to four carbon atoms, azido, alkylthio of one to four carbon atoms, and morpholinoalkyl wherein the alkyl moiety contains one to four carbon atoms; and R$_6$ is selected from hydrogen, fluoro, chloro, straight chain or branched chain alkyl containing one to four carbon atoms, and straight chain or branched chain fluoro- or chloroalkyl containing one to four carbon atoms and at least one fluorine or chlorine atom;

and pharmaceutically acceptable salts thereof.

In another embodiment, the IRM compound can be chosen from imidazopyridine amines defined by Formula VII below:

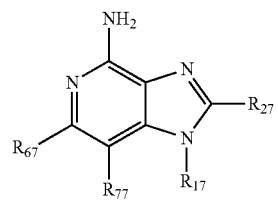

VII wherein

R$_{17}$ is selected from hydrogen; —CH$_2$R$_W$ wherein R$_W$ is selected from straight chain, branched chain, or cyclic alkyl containing one to ten carbon atoms, straight chain or branched chain alkenyl containing two to ten carbon atoms, straight chain or branched chain hydroxyalkyl containing one to six carbon atoms, alkoxyalkyl wherein the alkoxy moiety contains one to four carbon atoms and the alkyl moiety contains one to six carbon atoms, and phenylethyl; and —CH=CR$_Z$R$_Z$ wherein each R$_Z$ is independently straight chain, branched chain, or cyclic alkyl of one to six carbon atoms;

R$_{27}$ is selected from hydrogen; straight chain or branched chain alkyl containing one to eight carbon atoms; straight chain or branched chain hydroxyalkyl containing one to six carbon atoms; alkoxyalkyl wherein the alkoxy moiety contains one to four carbon atoms and the alkyl moiety contains one to six carbon atoms; benzyl, (phenyl)ethyl and phenyl, the benzyl, (phenyl)ethyl and phenyl being optionally substituted on the benzene ring by a moiety selected from methyl, methoxy, and halogen; and morpholinoalkyl wherein the alkyl moiety contains one to four carbon atoms;

R$_{67}$ and R$_{77}$ are independently selected from hydrogen and alkyl of one to five carbon atoms, with the proviso that R$_{67}$ and R$_{77}$ taken together contain no more than six carbon atoms, and with the further proviso that when R$_{77}$ is hydrogen then R$_{67}$ is other than hydrogen and R$_{27}$ is other than hydrogen or morpholinoalkyl, and with the further proviso that when R$_{67}$ is hydrogen then R$_{77}$ and R$_{27}$ are other than hydrogen;

and pharmaceutically acceptable salts thereof.

In another embodiment, the IRM compound can be chosen from 1,2 bridged imidazoquinoline amines defined by Formula VIII below:

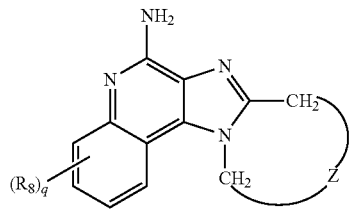

VIII wherein

Z is selected from

—(CH$_2$)$_p$— wherein p is 1 to 4;

—(CH$_2$)$_a$—C(R$_D$R$_E$)(CH$_2$)$_b$—, wherein a and b are integers and a+b is 0 to 3, R$_D$ is hydrogen or alkyl of one to four carbon atoms, and R$_E$ is selected from alkyl of one to four carbon atoms, hydroxy, —OR$_F$ wherein R$_F$ is alkyl of one to four carbon atoms, and —NR$_G$R'$_G$ wherein R$_G$ and R'$_G$ are independently hydrogen or alkyl of one to four carbon atoms; and —$(CH_2)_a$—(Y)—$(CH_2)_b$— wherein a and b are integers and a+b is 0 to 3, and Y is O, S, or —$NR_j$— wherein $R_j$ is hydrogen or alkyl of one to four carbon atoms;

q is 0 or 1; and $R_8$ is selected from alkyl of one to four carbon atoms, alkoxy of one to four carbon atoms, and halogen, and pharmaceutically acceptable salts thereof.

In another embodiment, the IRM compound can be chosen from thiazoloquinoline amines, oxazoloquinoline amines, thiazolopyridine amines, oxazolopyridine amines, thiazolonaphthyridine amines and oxazolonaphthyridine amines defined by Formula IX below:

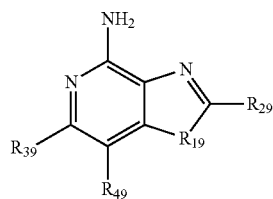

IX wherein:

$R_{19}$ is selected from oxygen, sulfur and selenium;

$R_{29}$ is selected from

-hydrogen;
-alkyl;
-alkyl-OH;
-haloalkyl;
-alkenyl;
-alkyl-X-alkyl;
-alkyl-X-alkenyl;
-alkenyl-X-alkyl;
-alkenyl-X-alkenyl;
-alkyl-$N(R_{59})_2$;
-alkyl-$N_3$;
-alkyl-O—C(O)—$N(R_{59})_2$;
-heterocyclyl;
-alkyl-X-heterocyclyl;
-alkenyl-X-heterocyclyl;
-aryl;
-alkyl-X-aryl;
-alkenyl-X-aryl;
-heteroaryl;
-alkyl-X-heteroaryl; and
-alkenyl-X-heteroaryl;

$R_{39}$ and $R_{49}$ are each independently:
-hydrogen;
—X-alkyl;
-halo;
-haloalkyl;
—$N(R_{59})_2$;

or when taken together, $R_{39}$ and $R_{49}$ form a fused aromatic, heteroaromatic, cycloalkyl or heterocyclic ring;

X is selected from —O—, —S—, —$NR_{59}$—, —C(O)—, —C(O)O—, —OC(O)—, and a bond; and each $R_{59}$ is independently H or $C_{1-8}$alkyl;

and pharmaceutically acceptable salts thereof.

In another embodiment, the IRM compound can be chosen from imidazonaphthyridine amines and imidazotetrahydronaphthyridine amines defined by Formulas X and XI below:

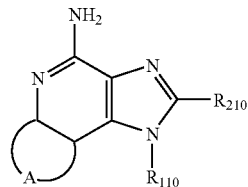

X wherein

A is =N—CR=CR—CR=; =CR—N=CR—CR=; =CR—CR=N—CR=; or =CR—CR=CR—N=;

$R_{110}$ is selected from:
-hydrogen;
—$C_{1-20}$ alkyl or $C_{2-20}$ alkenyl that is unsubstituted or substituted by one or more substituents selected from:
-aryl;
-heteroaryl;
-heterocyclyl;
—O—$C_{1-20}$ alkyl;
—O—$(C_{1-20}$ alkyl$)_{0-1}$-aryl;
—O—$(C_{1-20}$ alkyl$)_{0-1}$-heteroaryl;
—O—$(C_{1-20}$ alkyl$)_{0-1}$-heterocyclyl;
—CO—O—$C_{1-20}$ alkyl;
—$S(O)_{0-2}$—$C_{1-20}$ alkyl;
—$S(O)_{0-2}$—$(C_{1-20}$ alkyl$)_{0-1}$-aryl;
—$S(O)_{0-2}$—$(C_{1-20}$ alkyl$)_{0-1}$-heteroaryl;
—$S(O)_{0-2}$—$(C_{1-20}$ alkyl$)_{0-1}$-heterocyclyl;
—$N(R_{310})_2$;
—$N_3$;
oxo;
-halogen;
—$NO_2$;
—OH; and
—SH; and —$C_{1-20}$ alkyl-$NR_{310}$-Q-X—$R_{410}$ or —$C_{2-20}$ alkenyl-$NR_{310}$-Q-X—$R_{410}$ wherein Q is —CO— or —$SO_2$—; X is a bond, —O— or —$NR_{310}$— and $R_{410}$ is aryl; heteroaryl; heterocyclyl; or —$C_{1-20}$ alkyl or $C_{2-20}$ alkenyl that is unsubstituted or substituted by one or more substituents selected from:
-aryl;
-heteroaryl;
-heterocyclyl;
—O—$C_{1-20}$ alkyl;
—O—$(C_{1-20}$ alkyl$)_{0-1}$-aryl;
—O—$(C_{1-20}$ alkyl$)_{0-1}$-heteroaryl;
—O—$(C_{1-20}$ alkyl$)_{0-1}$-heterocyclyl;
—CO—O—$C_{1-20}$ alkyl;
—$S(O)_{0-2}$—$C_{1-20}$ alkyl;
—$S(O)_{0-2}$—$(C_{1-20}$ alkyl$)_{0-1}$-aryl;
—$S(O)_{0-2}$—$(C_{1-20}$ alkyl$)_{0-1}$-heteroaryl;
—$S(O)_{0-2}$—$(C_{1-20}$ alkyl$)_{0-1}$-heterocyclyl;
—$N(R_{310})_2$;
—$NR_{310}$—CO—O—$C_{1-20}$ alkyl;
—$N_3$;
oxo;
-halogen;
—$NO_2$;
—OH; and
—SH; or $R_{410}$ is

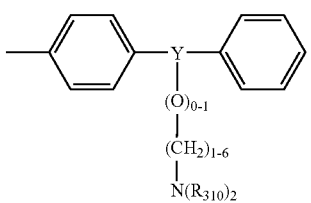

wherein Y is —N— or —CR—;
R$_{210}$ is selected from:
- hydrogen;
- —C$_{1-10}$ alkyl;
- —C$_{2-10}$ alkenyl;
- -aryl;
- —C$_{1-10}$ alkyl-O—C$_{1-10}$ alkyl;
- —C$_{1-10}$ alkyl-O—C$_{2-10}$ alkenyl; and
- —C$_{1-10}$ alkyl or C$_{2-10}$ alkenyl substituted by one or more substituents selected from:
  - —OH;
  - -halogen;
  - —N(R$_{310}$)$_2$;
  - —CO—N(R$_{310}$)$_2$;
  - —CO—C$_{1-10}$ alkyl;
  - —N$_3$;
  - -aryl;
  - -heteroaryl;
  - -heterocyclyl;
  - —CO-aryl; and
  - —CO-heteroaryl;

each R$_{310}$ is independently selected from hydrogen and C$_{1-10}$ alkyl; and each R is independently selected from hydrogen, C$_{1-10}$ alkyl, C$_{1-10}$ alkoxy, halogen and trifluoromethyl;

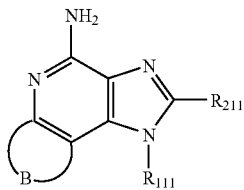

XI wherein
B is —NR—C(R)$_2$—C(R)$_2$—C(R)$_2$—; —C(R)$_2$—NR—C(R)$_2$—C(R)$_2$—; —C(R)$_2$—C(R)$_2$—NR—C(R)$_2$— or —C(R)$_2$—C(R)$_2$—C(R)$_2$—NR—;

R$_{111}$ is selected from:
- -hydrogen;
- —C$_{1-20}$ alkyl or C$_{2-20}$ alkenyl that is unsubstituted or substituted by one or more substituents selected from:
  - -aryl;
  - -heteroaryl;
  - -heterocyclyl;
  - —O—C$_{1-20}$ alkyl;
  - —O—(C$_{1-20}$ alkyl)$_{0-1}$-aryl;
  - —O—(C$_{1-20}$ alkyl)$_{0-1}$-heteroaryl;
  - —O—(C$_{1-20}$ alkyl)$_{0-1}$-heterocyclyl;
  - —CO—O—C$_{1-20}$ alkyl;
  - —S(O)$_{0-2}$—C$_{1-20}$ alkyl;
  - —S(O)$_{0-2}$—(C$_{1-20}$ alkyl)$_{0-1}$-aryl;
  - —S(O)$_{0-2}$—(C$_{1-20}$ alkyl)$_{0-1}$-heteroaryl;
  - —S(O)$_{0-2}$—(C$_{1-20}$ alkyl)$_{0-1}$-heterocyclyl;
  - —N(R$_{311}$)$_2$;
  - —N$_3$;
  - oxo;
  - -halogen;
  - —NO$_2$;
  - —OH; and
  - —SH; and
- —C$_{1-20}$ alkyl-NR$_{311}$-Q-X—R$_{411}$ or —C$_{2-20}$ alkenyl-NR$_{311}$-Q-X—R$_{411}$ wherein Q is —CO— or —SO$_2$—; X is a bond, —O— or —NR$_{311}$— and R$_{411}$ is aryl; heteroaryl; heterocyclyl; or —C$_{1-20}$ alkyl or C$_{2-20}$ alkenyl that is unsubstituted or substituted by one or more substituents selected from:
  - -aryl;
  - -heteroaryl;
  - -heterocyclyl;
  - —O—C$_{1-20}$ alkyl;
  - —O—(C$_{1-20}$ alkyl)$_{0-1}$-aryl;
  - —O—(C$_{1-20}$ alkyl)$_{0-1}$-heteroaryl;
  - —O—(C$_{1-20}$ alkyl)$_{0-1}$-heterocyclyl;
  - —CO—O—C$_{1-20}$ alkyl;
  - —S(O)$_{0-2}$—C$_{1-20}$ alkyl;
  - —S(O)$_{0-2}$—(C$_{1-20}$ alkyl)$_{0-1}$-aryl;
  - —S(O)$_{0-2}$—(C$_{1-20}$ alkyl)$_{0-1}$-heteroaryl;
  - —S(O)$_{0-2}$—(C$_{1-20}$ alkyl)$_{0-1}$-heterocyclyl;
  - —N(R$_{311}$)$_2$;
  - —NR$_{311}$—CO—O—C$_{1-20}$ alkyl;
  - —N$_3$;
  - oxo;
  - -halogen;
  - —NO$_2$;
  - —OH; and
  - —SH; or R$_{411}$ is

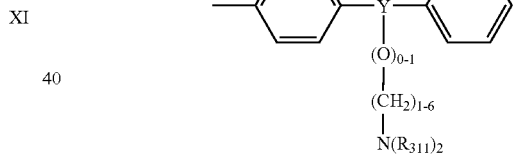

wherein Y is —N— or —CR—;
R$_{211}$ is selected from:
- -hydrogen;
- —C$_{1-10}$ alkyl;
- —C$_{2-10}$ alkenyl;
- -aryl;
- —C$_{1-10}$ alkyl—O—C$_{1-10}$-alkyl;
- —C$_{1-10}$ alkyl-O—C$_{2-10}$ alkenyl; and
- —C$_{1-10}$ alkyl or C$_{2-10}$ alkenyl substituted by one or more substituents selected from:
  - —OH;
  - -halogen;
  - —N(R$_{311}$)$_2$;
  - —CO—N(R$_{311}$)$_2$;
  - —CO—C$_{1-10}$ alkyl;
  - —N$_3$;
  - -aryl;
  - -heteroaryl;
  - -heterocyclyl;
  - —CO-aryl; and
  - —CO-heteroaryl;

each R$_{311}$ is independently selected from hydrogen and C$_{1-10}$ alkyl; and each R is independently selected from hydrogen, $C_{1-10}$ alkyl, $C_{1-10}$ alkoxy, halogen, and trifluoromethyl;
and pharmaceutically acceptable salts thereof.

In another embodiment, the IRM compound can be chosen from 1H-imidazo[4,5-c]quinolin-4-amines and tetrahydro-1H-imidazo[4,5-c]quinolin-4-amines defined by Formulas XII, XIII and XIV below:

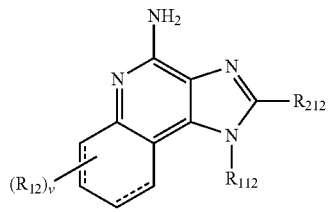

XII wherein $R_{112}$ is -alkyl-$NR_{312}$—CO—$R_{412}$ or -alkenyl-$NR_{312}$—CO—$R_{412}$ wherein $R_{412}$ is aryl, heteroaryl, alkyl or alkenyl, each of which may be unsubstituted or substituted by one or more substituents selected from:
- -alkyl;
- -alkenyl;
- -alkynyl;
- -(alkyl)$_{0-1}$-aryl;
- -(alkyl)$_{0-1}$-(substituted aryl);
- -(alkyl)$_{0-1}$-heteroaryl;
- -(alkyl)$_{0-1}$-(substituted heteroaryl);
- —O-alkyl;
- —O-(alkyl)$_{0-1}$-aryl;
- —O-(alkyl)$_{0-1}$-(substituted aryl);
- —O-(alkyl)$_{0-1}$-heteroaryl;
- —O-(alkyl)$_{0-1}$-(substituted heteroaryl);
- —CO-aryl;
- —CO-(substituted aryl);
- —CO-heteroaryl;
- —CO-(substituted heteroaryl);
- —COOH;
- —CO—O-alkyl;
- —CO-alkyl;
- —S(O)$_{0-2}$-alkyl;
- —S(O)$_{0-2}$-(alkyl)$_{0-1}$-aryl;
- —S(O)$_{0-2}$-(alkyl)$_{0-1}$-(substituted aryl);
- —S(O)$_{0-2}$-(alkyl)$_{0-1}$-heteroaryl;
- —S(O)$_{0-2}$-(alkyl)$_{0-1}$-(substituted heteroaryl);
- —P(O)(O$R_{312}$)$_2$;
- —$NR_{312}$—CO—O-alkyl;
- —$N_3$;
- -halogen;
- —$NO_2$;
- —CN;
- -haloalkyl;
- —O-haloalkyl;
- —CO-haloalkyl;
- —OH;
- —SH; and in the case that $R_{412}$ is alkyl, alkenyl, or heterocyclyl, oxo;

or $R_{412}$ is

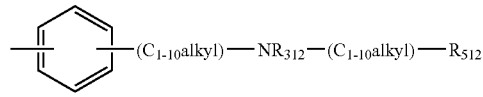

wherein $R_{512}$ is an aryl, (substituted aryl), heteroaryl, (substituted heteroaryl), heterocyclyl or (substituted heterocyclyl) group;

$R_{212}$ is selected from:
- -hydrogen;
- -alkyl;
- -alkenyl;
- -aryl;
- -(substituted aryl);
- -heteroaryl;
- -(substituted heteroaryl);
- -heterocyclyl;
- -(substituted heterocyclyl);
- -alkyl-O-alkyl;
- -alkyl-O-alkenyl; and
- -alkyl or alkenyl substituted by one or more substituents selected from:
  - —OH;
  - -halogen;
  - —N($R_{312}$)$_2$;
  - —CO—N($R_{312}$)$_2$;
  - —CO—$C_{1-10}$ alkyl;
  - —CO—O—$C_{1-10}$ alkyl;
  - —$N_3$;
  - -aryl;
  - -(substituted aryl);
  - -heteroaryl;
  - -(substituted heteroaryl);
  - -heterocyclyl;
  - -(substituted heterocyclyl);
  - —CO-aryl; and
  - —CO-heteroaryl;

each $R_{312}$ is independently selected from hydrogen; $C_{1-10}$ alkyl-heteroaryl; $C_{1-10}$ alkyl-(substituted heteroaryl); $C_{1-10}$ alkyl-aryl; $C_{1-10}$ alkyl-(substituted aryl) and $C_{1-10}$ alkyl;

v is 0 to 4;

and each $R_{12}$ present is independently selected from $C_{1-10}$ alkyl, $C_{1-10}$ alkoxy, halogen, and trifluoromethyl;

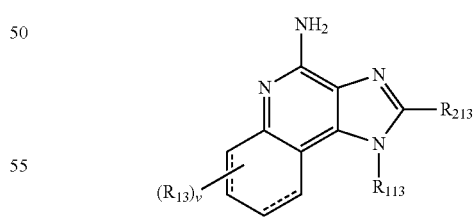

XIII wherein $R_{113}$ is -alkyl-$NR_{313}$—$SO_2$—X—$R_{413}$ or -alkenyl-$NR_{313}$—$SO_2$—X—$R_{413}$;

X is a bond or —$NR_{513}$—;

$R_{413}$ is aryl, heteroaryl, heterocyclyl, alkyl or alkenyl, each of which may be unsubstituted or substituted by one or more substituents selected from:
- -alkyl;
- -alkenyl;

-aryl;
-heteroaryl;
-heterocyclyl;
-substituted cycloalkyl;
-substituted aryl;
-substituted heteroaryl;
-substituted heterocyclyl;
—O-alkyl;
—O-(alkyl)$_{0-1}$-aryl;
—O-(alkyl)$_{0-1}$-substituted aryl;
—O-(alkyl)$_{0-1}$-heteroaryl;
—O-(alkyl)$_{0-1}$-substituted heteroaryl;
—O-(alkyl)$_{0-1}$-heterocyclyl;
—O-(alkyl)$_{0-1}$-substituted heterocyclyl;
—COOH;
—CO—O-alkyl;
—CO-alkyl;
—S(O)$_{0-2}$-alkyl;
—S(O)$_{0-2}$-(alkyl)$_{0-1}$-aryl;
—S(O)$_{0-2}$-(alkyl)$_{0-1}$-substituted aryl;
—S(O)$_{0-2}$-(alkyl)$_{0-1}$-heteroaryl;
—S(O)$_{0-2}$-(alkyl)$_{0-1}$-substituted heteroaryl;
—S(O)$_{0-2}$-(alkyl)$_{0-1}$-heterocyclyl;
—S(O)$_{0-2}$-(alkyl)$_{0-1}$-substituted heterocyclyl;
-(alkyl)$_{0-1}$-NR$_{313}$R$_{313}$;
-(alkyl)$_{0-1}$-NR$_{313}$—CO—O-alkyl;
-(alkyl)$_{0-1}$-NR$_{313}$—CO-alkyl;
-(alkyl)$_{0-1}$-NR$_{313}$—CO-aryl;
-(alkyl)$_{0-1}$-NR$_{313}$—CO-substituted aryl;
-(alkyl)$_{0-1}$-NR$_{313}$—CO-heteroaryl;
-(alkyl)$_{0-1}$-NR$_{313}$—CO-substituted heteroaryl;
—N$_3$;
-halogen;
-haloalkyl;
-haloalkoxy;
—CO-haloalkyl;
—CO-haloalkoxy;
—NO$_2$;
—CN;
—OH;
—SH; and in the case that R$_{413}$ is alkyl, alkenyl, or heterocyclyl, oxo;
R$_{213}$ is selected from:
-hydrogen;
-alkyl;
-alkenyl;
-aryl;
-substituted aryl;
-heteroaryl;
-substituted heteroaryl;
-alkyl-O-alkyl;
-alkyl-O-alkenyl; and
-alkyl or alkenyl substituted by one or more substituents
 selected from:
   —OH;
   -halogen;
   —N(R$_{313}$)$_2$;
   —CO—N(R$_{313}$)$_2$;
   —CO—C$_{1-10}$ alkyl;
   —CO—O—C$_{1-10}$ alkyl;
   —N$_3$;
   -aryl;
   -substituted aryl;
   -heteroaryl;
   -substituted heteroaryl;
   -heterocyclyl;
   -substituted heterocyclyl;
   —CO-aryl;
   —CO-(substituted aryl);
   —CO-heteroaryl; and
   —CO-(substituted heteroaryl);
each R$_{313}$ is independently selected from hydrogen and C$_{1-10}$ alkyl; or when X is a bond R$_{313}$ and R$_{413}$ can join to form a 3 to 7 membered heterocyclic or substituted heterocyclic ring;
R$_{513}$ is selected from hydrogen and C$_{1-10}$ alkyl, or R$_{413}$ and R$_{513}$ can combine to form a 3 to 7 membered heterocyclic or substituted heterocyclic ring;
v is 0 to 4;
and each R$_{13}$ present is independently selected from C$_{1-10}$ alkyl, C$_{1-10}$ alkoxy, halogen, and trifluoromethyl;

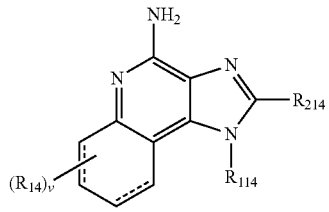

XIV wherein
R$_{114}$ is -alkyl-NR$_{314}$—CY—NR$_{514}$—X—R$_{414}$ or
-alkenyl-NR$_{314}$—CY—NR$_{514}$—X—R$_{414}$
wherein
Y is =O or =S;
X is a bond, —CO— or —SO$_2$—;
R$_{414}$ is aryl, heteroaryl, heterocyclyl, alkyl or alkenyl, each of which may be unsubstituted or substituted by one or more substituents selected from:
-alkyl;
-alkenyl;
-aryl;
-heteroaryl;
-heterocyclyl;
-substituted aryl;
-substituted heteroaryl;
-substituted heterocyclyl;
—O-alkyl;
—O-(alkyl)$_{0-1}$-aryl;
—O-(alkyl)$_{0-1}$-substituted aryl;
—O-(alkyl)$_{0-1}$-heteroaryl;
—O-(alkyl)$_{0-1}$-substituted heteroaryl;
—O-(alkyl)$_{0-1}$-heterocyclyl;
—O-(alkyl)$_{0-1}$-substituted heterocyclyl;
—COOH;
—CO—O-alkyl;
—CO-alkyl;
—S(O)$_{0-2}$-alkyl;
—S(O)$_{0-2}$-(alkyl)$_{0-1}$-aryl;
—S(O)$_{0-2}$-(alkyl)$_{0-1}$-substituted aryl;
—S(O)$_{0-2}$-(alkyl)$_{0-1}$-heteroaryl;
—S(O)$_{0-2}$-(alkyl)$_{0-1}$-substituted heteroaryl;
—S(O)$_{0-2}$-(alkyl)$_{0-1}$-heterocyclyl;
—S(O)$_{0-2}$-(alkyl)$_{0-1}$-substituted heterocyclyl;
-(alkyl)$_{0-1}$-NR$_{314}$R$_{314}$;
-(alkyl)$_{0-1}$-NR$_{314}$—CO—O-alkyl;
-(alkyl)$_{0-1}$-NR$_{314}$—CO-alkyl;
-(alkyl)$_{0-1}$-NR$_{314}$—CO-aryl;
-(alkyl)$_{0-1}$-NR$_{314}$—CO-substituted aryl;
-(alkyl)$_{0-1}$-NR$_{314}$—CO-heteroaryl;
-(alkyl)$_{0-1}$-NR$_{314}$—CO-substituted heteroaryl;

—N₃;
-halogen;
-haloalkyl;
-haloalkoxy;
—CO-haloalkoxy;
—NO₂;
—CN;
—OH;
—SH; and, in the case that $R_{414}$ is alkyl, alkenyl or heterocyclyl, oxo;

with the proviso that when X is a bond $R_{414}$ can additionally be hydrogen;

$R_{214}$ is selected from:
-hydrogen;
-alkyl;
-alkenyl;
-aryl;
-substituted aryl;
-heteroaryl;
-substituted heteroaryl;
-alkyl-O-alkyl;
-alkyl-O-alkenyl; and
-alkyl or alkenyl substituted by one or more substituents selected from:
    —OH;
    -halogen;
    —N($R_{314}$)₂;
    —CO—N($R_{314}$)₂;
    —CO—$C_{1-10}$ alkyl;
    —CO—O—$C_{1-10}$ alkyl;
    —N₃;
    -aryl;
    -substituted aryl;
    -heteroaryl;
    -substituted heteroaryl;
    -heterocyclyl;
    -substituted heterocyclyl;
    —CO-aryl;
    —CO-(substituted aryl);
    —CO-heteroaryl; and
    —CO-(substituted heteroaryl);

each $R_{314}$ is independently selected from hydrogen and $C_{1-10}$ alkyl;

$R_{514}$ is selected from hydrogen and $C_{1-10}$ alkyl, or $R_{414}$ and $R_{514}$ can combine to form a 3 to 7 membered heterocyclic or substituted heterocyclic ring;

v is 0 to 4;

and each $R_{14}$ present is independently selected from $C_{1-10}$ alkyl, $C_{1-10}$ alkoxy, halogen, and trifluoromethyl;

and pharmaceutically acceptable salts thereof.

In another embodiment, the IRM compound can be chosen from 1H-imidazo[4,5-c]quinolin-4-amines and tetrahydro-1H-imidazo[4,5-c]quinolin-4-amines defined by Formulas XV, XVI, XVII, XVIII, XIX, XX, XXI, XXII, XXIII, XXIV, XXV, and XXVI below:

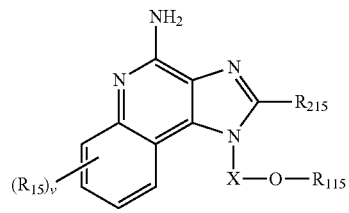

XV wherein: X is —$CHR_{515}$—, —$CHR_{515}$-alkyl-, or —$CHR_{515}$-alkenyl-;

$R_{115}$ is selected from:
    —$R_{415}$—$CR_{315}$-Z-$R_{615}$-alkyl;
    $R_{415}$—$CR_{315}$-Z-$R_{615}$-alkenyl;
    —$R_{415}$—$CR_{315}$-Z-$R_{615}$-aryl;
    —$R_{415}$—$CR_{315}$-Z-$R_{615}$-heteroaryl;
    —$R_{415}$—$CR_{315}$-Z-$R_{615}$-heterocyclyl;
    —$R_{415}$—$CR_{315}$-Z-H;
    —$R_{415}$—$NR_{715}$—$CR_{315}$—$R_{615}$-alkyl;
    —$R_{415}$—$NR_{715}$—$CR_{315}$—$R_{615}$-alkenyl;
    —$R_{415}$—$NR_{715}$—$CR_{315}$—$R_{615}$-aryl;
    —$R_{415}$—$NR_{715}$—$CR_{315}$—$R_{615}$-heteroaryl;
    —$R_{415}$—$NR_{715}$—$CR_{315}$—$R_{615}$-heterocyclyl; and
    —$R_{415}$—$NR_{715}$—$CR_{315}$—$R_{815}$;

Z is —$NR_{515}$—, —O—, or —S—;

$R_{215}$ is selected from:
    -hydrogen;
    -alkyl;
    -alkenyl;
    -aryl;
    -heteroaryl;
    -heterocyclyl;
    -alkyl-Y-alkyl;
    -alkyl-Y-alkenyl;
    -alkyl-Y-aryl; and
    -alkyl or alkenyl substituted by one or more substituents selected from:
        —OH;
        -halogen;
        —N($R_{515}$)₂;
        —CO—N($R_{515}$)₂;
        —CO—$C_{1-10}$ alkyl;
        —CO—O—$C_{1-10}$ alkyl;
        —N₃;
        -aryl;
        -heteroaryl;
        -heterocyclyl;
        —CO-aryl; and
        —CO-heteroaryl;

$R_{315}$ is =O or =S;

$R_{415}$ is alkyl or alkenyl, which may be interrupted by one or more —O— groups;

each $R_{515}$ is independently H or $C_{1-10}$ alkyl;

$R_{615}$ is a bond, alkyl, or alkenyl, which may be interrupted by one or more —O— groups;

$R_{715}$ is H, $C_{1-10}$ alkyl, or arylalkyl; or $R_{415}$ and $R_{715}$ can join together to form a ring;

$R_{815}$ is H or $C_{1-10}$ alkyl; or $R_{715}$ and $R_{815}$ can join together to form a ring;

Y is —O— or —$S(O)_{0-2}$—;

v is 0 to 4; and each $R_{15}$ present is independently selected from $C_{1-10}$ alkyl, $C_{1-10}$ alkoxy, hydroxy, halogen, and trifluoromethyl;

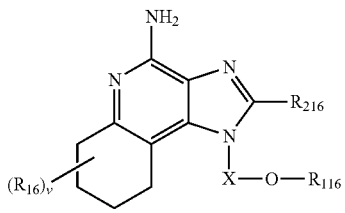

XVI wherein: X is —CHR$_{516}$—, —CHR$_{516}$-alkyl-, or —CHR$_{516}$-alkenyl-;
R$_{416}$ is selected from:
—R$_{416}$—CR$_{316}$-Z-R$_{616}$-alkyl;
—R$_{416}$—CR$_{316}$-Z-R$_{616}$-alkenyl;
—R$_{416}$—CR$_{316}$-Z-R$_{616}$-aryl;
—R$_{416}$—CR$_{316}$-Z-R$_{616}$-heteroaryl;
—R$_{416}$—CR$_{316}$-Z-R$_{616}$-heterocyclyl;
—R$_{416}$—CR$_{316}$-Z-H;
—R$_{416}$—NR$_{716}$—CR$_{316}$—R$_{616}$-alkyl;
—R$_{416}$—NR$_{716}$—CR$_{316}$—R$_{616}$-alkenyl;
—R$_{416}$—NR$_{716}$—CR$_{316}$—R$_{616}$-aryl;
—R$_{416}$—NR$_{716}$—CR$_{316}$—R$_{616}$-heteroaryl;
—R$_{416}$—NR$_{716}$—CR$_{316}$—R$_{616}$-heterocyclyl; and
—R$_{416}$—NR$_{716}$—CR$_{316}$—R$_{816}$;
Z is —NR$_{516}$—, —O—, or —S—;
R$_{216}$ is selected from:
-hydrogen;
-alkyl;
-alkenyl;
-aryl;
-heteroaryl;
-heterocyclyl;
-alkyl-Y-alkyl;
-alkyl-Y-alkenyl;
-alkyl-Y-aryl; and
-alkyl or alkenyl substituted by one or more substituents selected from:
—OH;
-halogen;
—N(R$_{516}$)$_2$;
—CO—N(R$_{516}$)$_2$;
—CO—C$_{1-10}$ alkyl;
—CO—O—C$_{1-10}$ alkyl;
—N$_3$;
-aryl;
-heteroaryl;
-heterocyclyl;
—CO-aryl; and
—CO-heteroaryl;
R$_{316}$ is =O or =S;
R$_{416}$ is alkyl or alkenyl, which may be interrupted by one or more —O— groups;
each R$_{516}$ is independently H or C$_{1-10}$ alkyl;
R$_{616}$ is a bond, alkyl, or alkenyl, which may be interrupted by one or more —O— groups;
R$_{716}$ is H, C$_{1-10}$ alkyl, arylalkyl; or R$_{416}$ and R$_{716}$ can join together to form a ring;
R$_{816}$ is H or C$_{1-10}$ alkyl; or R$_{716}$ and R$_{816}$ can join together to form a ring;
Y is —O— or —S(O)$_{0-2}$—;
v is 0 to 4; and
each R$_{16}$ present is independently selected from C$_{1-10}$ alkyl, C$_{1-10}$ alkoxy, hydroxy, halogen, and trifluoromethyl;

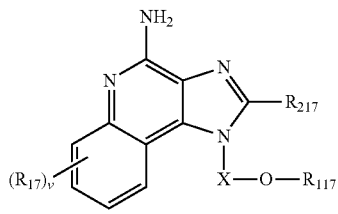

XVII wherein: X is —CHR$_{317}$—, —CHR$_{317}$-alkyl-, or —CHR$_{317}$-alkenyl-;
R$_{117}$ is selected from:
-alkenyl;
-aryl; and
—R$_{417}$-aryl;
R$_{217}$ is selected from:
-hydrogen;
-alkyl;
-alkenyl;
-aryl;
-heteroaryl;
-heterocyclyl;
-alkyl-Y-alkyl;
-alkyl-Y-alkenyl;
-alkyl-Y-aryl; and
-alkyl or alkenyl substituted by one or more substituents selected from:
—OH;
-halogen;
—N(R$_{317}$)$_2$;
—CO—N(R$_{317}$)$_2$;
—CO—C$_{1-10}$ alkyl;
—CO—O—C$_{1-10}$ alkyl;
—N$_3$;
-aryl;
-heteroaryl;
-heterocyclyl;
—CO-aryl; and
—CO-heteroaryl;
R$_{417}$ is alkyl or alkenyl, which may be interrupted by one or more —O— groups;
each R$_{317}$ is independently H or C$_{1-10}$ alkyl;
each Y is independently —O— or —S(O)$_{0-2}$—;
v is 0 to 4; and
each R$_{17}$ present is independently selected from C$_{1-10}$ alkyl, C$_{1-10}$ alkoxy, hydroxy, halogen, and trifluoromethyl;

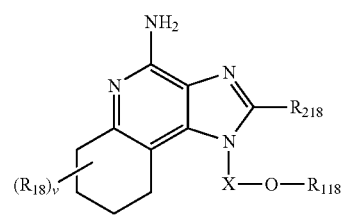

XVIII wherein: X is —CHR$_{318}$—, —CHR$_{318}$-alkyl-, or —CHR$_{318}$-alkenyl-;

$R_{118}$ is selected from:
- -aryl;
- -alkenyl; and
- —$R_{418}$-aryl;

$R_{218}$ is selected from:
- -hydrogen;
- -alkyl;
- -alkenyl;
- -aryl;
- -heteroaryl;
- -heterocyclyl;
- -alkyl-Y-alkyl;
- -alkyl-Y-aryl;
- -alkyl-Y-alkenyl; and
- -alkyl or alkenyl substituted by one or more substituents selected from:
  - —OH;
  - -halogen;
  - —$N(R_{318})_2$;
  - —CO—$N(R_{318})_2$;
  - —CO—$C_{1-10}$ alkyl;
  - —CO—O—$C_{1-10}$ alkyl;
  - —$N_3$;
  - -aryl;
  - -heteroaryl;
  - -heterocyclyl;
  - —CO-aryl; and
  - —CO-heteroaryl;

$R_{418}$ is alkyl or alkenyl, which may be interrupted by one or more —O— groups;
each $R_{318}$ is independently H or $C_{1-10}$ alkyl;
each Y is independently —O— or —$S(O)_{0-2}$—;
v is 0 to 4; and
each $R_{18}$ present is independently selected $C_{1-10}$ alkyl, $C_{1-10}$ alkoxy, hydroxy, halogen, and trifluoromethyl;

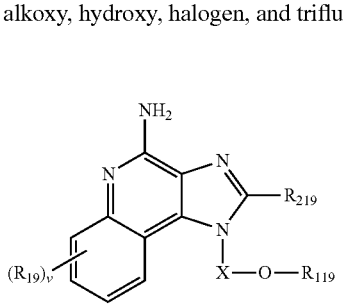

XIX wherein: X is —$CHR_{319}$—, —$CHR_{319}$-alkyl-, or —$CHR_{319}$-alkenyl-;

$R_{119}$ is selected from:
- -heteroaryl;
- -heterocyclyl;
- —$R_{419}$-heteroaryl; and
- —$R_{419}$-heterocyclyl;

$R_{219}$ is selected from:
- -hydrogen;
- -alkyl;
- -alkenyl;
- -aryl;
- -heteroaryl;
- -heterocyclyl;
- -alkyl-Y-alkyl;
- -alkyl-Y-alkenyl;
- -alkyl-Y-aryl; and
- -alkyl or alkenyl substituted by one or more substituents selected from:
  - —OH;
  - -halogen;
  - —$N(R_{319})_2$;
  - —CO—$N(R_{319})_2$;
  - —CO—$C_{1-10}$ alkyl;
  - —CO—O—$C_{1-10}$ alkyl;
  - —$N_3$;
  - -aryl;
  - -heteroaryl;
  - -heterocyclyl;
  - —CO-aryl; and
  - —CO-heteroaryl;

$R_{419}$ is alkyl or alkenyl, which may be interrupted by one or more —O— groups;
each $R_{319}$ is independently H or $C_{1-10}$ alkyl;
each Y is independently —O— or —$S(O)_{0-2}$—;
v is 0 to 4; and
each $R_{19}$ present is independently selected from $C_{1-10}$ alkyl, $C_{1-10}$ alkoxy, hydroxy, halogen, and trifluoromethyl;

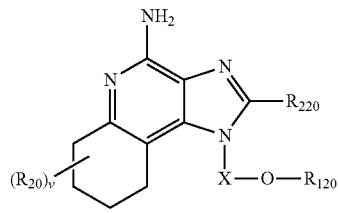

XX wherein: X is —$CHR_{320}$—, —$CHR_{320}$-alkyl-, or —$CHR_{320}$-alkenyl-;

$R_{120}$ is selected from:
- -heteroaryl;
- -heterocyclyl;
- —$R_{420}$-heteroaryl; and
- —$R_{420}$-heterocyclyl;

$R_{220}$ is selected from:
- -hydrogen;
- -alkyl;
- -alkenyl;
- -aryl;
- -heteroaryl;
- -heterocyclyl;
- -alkyl-Y-alkyl;
- -alkyl-Y-alkenyl;
- -alkyl-Y-aryl; and
- -alkyl or alkenyl substituted by one or more substituents selected from:
  - —OH;
  - -halogen;
  - —$N(R_{320})_2$;
  - —CO—$N(R_{320})_2$;
  - —CO—$C_{1-10}$ alkyl;
  - —CO—O—$C_{1-10}$ alkyl;
  - —$N_3$;
  - -aryl;
  - -heteroaryl;
  - -heterocyclyl;
  - —CO-aryl; and
  - —CO-heteroaryl;

$R_{420}$ is alkyl or alkenyl, which may be interrupted by one or more —O— groups;

each $R_{320}$ is independently H or $C_{1-10}$ alkyl;
each Y is independently —O— or —S(O)$_{0-2}$—;
v is 0 to 4; and
each $R_{20}$ present is independently selected from $C_{1-10}$ alkyl, $C_{1-10}$ alkoxy, hydroxy, halogen, and trifluoromethyl;

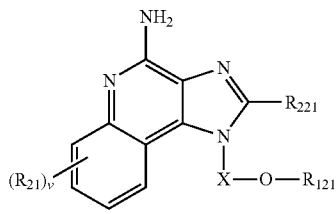

XXI wherein: X is —CHR$_{521}$—, —CHR$_{521}$-alkyl-, or —CHR$_{521}$-alkenyl-;
$R_{121}$ is selected from:
—$R_{421}$—NR$_{321}$—SO$_2$—R$_{621}$-alkyl;
—$R_{421}$—NR$_{321}$—SO$_2$—R$_{621}$-alkenyl;
—$R_{421}$—NR$_{321}$—SO$_2$—R$_{621}$-aryl;
—$R_{421}$—NR$_{321}$—SO$_2$—R$_{621}$-heteroaryl;
—$R_{421}$—NR$_{321}$—SO$_2$—R$_{621}$-heterocyclyl;
—$R_{421}$—NR$_{321}$—SO$_2$—R$_{721}$;
—$R_{421}$—NR$_{321}$—SO$_2$—NR$_{521}$—R$_{621}$-alkyl;
—$R_{421}$—NR$_{321}$—SO$_2$—NR$_{521}$—R$_{621}$-alkenyl;
—$R_{421}$—NR$_{321}$—SO$_2$—NR$_{521}$—R$_{621}$-aryl;
—$R_{421}$—NR$_{321}$—SO$_2$—NR$_{521}$—R$_{621}$-heteroaryl;
—$R_{421}$—NR$_{321}$—SO$_2$—NR$_{521}$—R$_{621}$-heterocyclyl; and
—$R_{421}$—NR$_{321}$—SO$_2$—NH$_2$;
$R_{221}$ is selected from:
-hydrogen;
-alkyl;
-alkenyl;
-aryl;
-heteroaryl;
-heterocyclyl;
-alkyl-Y-alkyl;
-alkyl-Y-alkenyl;
-alkyl-Y-aryl; and
-alkyl or alkenyl substituted by one or more substituents selected from:
—OH;
-halogen;
—N(R$_{521}$)$_2$;
—CO—N(R$_{521}$)$_2$;
—CO—C$_{1-10}$ alkyl;
—CO—O—C$_{1-10}$ alkyl;
—N$_3$;
-aryl;
-heteroaryl;
-heterocyclyl;
—CO-aryl; and
—CO-heteroaryl;
Y is —O— or —S(O)$_{0-2}$—;
$R_{321}$ is H, $C_{1-10}$ alkyl, or arylalkyl;
each $R_{421}$ is independently alkyl or alkenyl, which may be interrupted by one or more —O— groups; or $R_{321}$ and $R_{421}$ can join together to form a ring;
each $R_{521}$ is independently H, $C_{1-10}$ alkyl, or $C_{2-10}$ alkenyl;
$R_{621}$ is a bond, alkyl, or alkenyl, which may be interrupted by one or more —O— groups;

$R_{721}$ is $C_{1-10}$ alkyl; or $R_{321}$ and $R_{721}$ can join together to form a ring;
v is 0 to 4; and
each $R_{21}$ present is independently selected from $C_{1-10}$ alkyl, $C_{1-10}$ alkoxy, hydroxy, halogen, and trifluoromethyl;

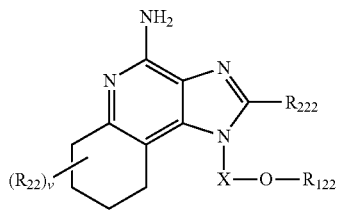

XXII wherein: X is —CHR$_{522}$—, —CHR$_{522}$-alkyl-, or —CHR$_{522}$-alkenyl-;
$R_{122}$ is selected from:
—$R_{422}$—NR$_{322}$—SO$_2$—R$_{622}$-alkyl;
—$R_{422}$—NR$_{322}$—SO$_2$—R$_{622}$-alkenyl;
—$R_{422}$—NR$_{322}$—SO$_2$—R$_{622}$-aryl;
—$R_{422}$—NR$_{322}$—SO$_2$—R$_{622}$-heteroaryl;
—$R_{422}$—NR$_{322}$—SO$_2$—R$_{622}$-heterocyclyl;
—$R_{422}$—NR$_{322}$—SO$_2$—R$_{722}$;
—$R_{422}$—NR$_{322}$—SO$_2$—NR$_{522}$—R$_{622}$-alkyl;
—$R_{422}$—NR$_{322}$—SO$_2$—NR$_{522}$—R$_{622}$-alkenyl;
—$R_{422}$—NR$_{322}$—SO$_2$—NR$_{522}$—R$_{622}$-aryl;
—$R_{422}$—NR$_{322}$—SO$_2$—NR$_{522}$—R$_{622}$-heteroaryl;
—$R_{422}$—NR$_{322}$—SO$_2$—NR$_{522}$—R$_{622}$-heterocyclyl; and
—$R_{422}$—NR$_{322}$—SO$_2$—NH$_2$;
$R_{222}$ is selected from:
-hydrogen;
-alkyl;
-alkenyl;
-aryl;
-heteroaryl;
-heterocyclyl;
-alkyl-Y-alkyl;
-alkyl-Y-alkenyl;
-alkyl-Y-aryl; and
-alkyl or alkenyl substituted by one or more substituents selected from:
—OH;
-halogen;
—N(R$_{522}$)$_2$;
—CO—N(R$_{522}$)$_2$;
—CO—C$_{1-10}$ alkyl;
—CO—O—C$_{1-10}$ alkyl;
—N$_3$;
-aryl;
-heteroaryl;
-heterocyclyl;
—CO-aryl; and
—CO-heteroaryl;
Y is —O— or —S(O)$_{0-2}$—;
$R_{322}$ is H, $C_{1-10}$ alkyl, or arylalkyl;
each $R_{422}$ is independently alkyl or alkenyl, which may be interrupted by one or more —O— groups; or $R_{322}$ and $R_{422}$ can join together to form a ring;
each $R_{522}$ is independently H, $C_{1-10}$ alkyl, or $C_{2-10}$ alkenyl;
$R_{622}$ is a bond, alkyl, or alkenyl, which may be interpreted by one or more —O— groups;

$R_{722}$ is $C_{1-10}$ alkyl; or $R_{322}$ and $R_{722}$ can join together to form a ring;

v is 0 to 4; and each $R_{22}$ present is independently selected from $C_{1-10}$ alkyl, $C_{10}$ alkoxy, hydroxy, halogen, and trifluoromethyl;

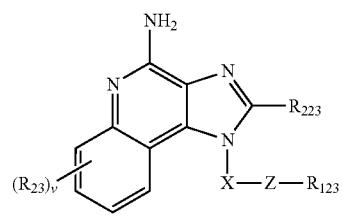

XXIII wherein: X is —$CHR_{323}$—, —$CHR_{323}$-alkyl-, or —$CHR_{323}$-alkenyl-;

Z is —S—, —SO—, or —$SO_2$—;

$R_{123}$ is selected from:
- -alkyl;
- -aryl;
- -heteroaryl;
- -heterocyclyl;
- -alkenyl;
- —$R_{423}$-aryl;
- —$R_{423}$-heteroaryl; and
- —$R_{423}$-heterocyclyl;

$R_{223}$ is selected from:
- -hydrogen;
- -alkyl;
- -alkenyl;
- -aryl;
- -heteroaryl;
- -heterocyclyl;
- -alkyl-Y-alkyl;
- -alkyl-Y-alkenyl;
- -alkyl-Y-aryl; and
- -alkyl or alkenyl substituted by one or more substituents selected from:
  - —OH;
  - -halogen;
  - —$N(R_{323})_2$;
  - —CO—$N(R_{323})_2$;
  - —CO—$C_{1-10}$ alkyl;
  - —CO—O—$C_{1-10}$ alkyl;
  - —$N_3$;
  - -aryl;
  - -heteroaryl;
  - -heterocyclyl;
  - —CO-aryl; and
  - —CO-heteroaryl;

each $R_{323}$ is independently H or $C_{1-10}$ alkyl;

each $R_{423}$ is independently alkyl or alkenyl;

each Y is independently —O— or —$S(O)_{0-2}$—;

v is 0 to 4; and each $R_{23}$ present is independently selected from $C_{1-10}$ alkyl, $C_{1-10}$ alkoxy, hydroxy, halogen, and trifluoromethyl;

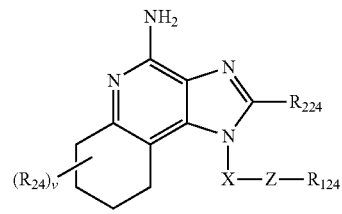

XXIV wherein: X is —$CHR_{324}$—, —$CHR_{324}$-alkyl-, or —$CHR_{324}$-alkenyl-;

Z is —S—, —SO—, or —$SO_2$—;

$R_{124}$ is selected from:
- -alkyl;
- -aryl;
- -heteroaryl;
- -heterocyclyl;
- -alkenyl;
- —$R_{424}$-aryl;
- —$R_{424}$-heteroaryl; and
- —$R_{424}$-heterocyclyl;

$R_{224}$ is selected from:
- -hydrogen;
- -alkyl;
- -alkenyl;
- -aryl;
- -heteroaryl;
- -heterocyclyl;
- -alkyl-Y-alkyl;
- -alkyl-Y-alkenyl;
- -alkyl-Y-aryl; and
- -alkyl or alkenyl substituted by one or more substituents selected from:
  - —OH;
  - -halogen;
  - —$N(R_{324})_2$;
  - —CO—$N(R_{324})_2$;
  - —CO—$C_{1-10}$ alkyl;
  - —CO—O—$C_{1-10}$ alkyl;
  - —$N_3$;
  - -aryl;
  - -heteroaryl;
  - -heterocyclyl;
  - —CO-aryl; and
  - —CO-heteroaryl;

each $R_{324}$ is independently H or $C_{1-10}$ alkyl;

each $R_{424}$ is independently alkyl or alkenyl;

each Y is independently —O— or —$S(O)_{0-2}$—;

v is 0 to 4; and each $R_{24}$ present is independently selected from $C_{1-10}$ alkyl, $C_{1-10}$ alkoxy, hydroxy, halogen, and trifluoromethyl;

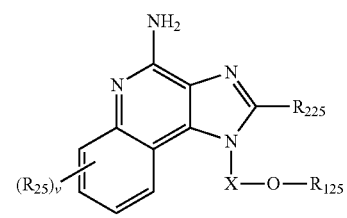

XXV wherein: X is —CHR$_{525}$—, —CHR$_{525}$-alkyl-, or —CHR$_{525}$-alkenyl-;

R$_{125}$ is selected from:
- —R$_{425}$—NR$_{825}$—CR$_{325}$—NR$_{525}$-Z-R$_{625}$-alkyl;
- —R$_{425}$—NR$_{825}$—CR$_{325}$—NR$_{525}$-Z-R$_{625}$-alkenyl;
- —R$_{425}$—NR$_{825}$—CR$_{325}$—NR$_{525}$-Z-R$_{625}$-aryl;
- —R$_{425}$—NR$_{825}$—CR$_{325}$—NR$_{525}$-Z-R$_{625}$-heteroaryl;
- —R$_{425}$—NR$_{825}$—CR$_{325}$—NR$_{525}$-Z-R$_{625}$-heterocyclyl;
- —R$_{425}$—NR$_{825}$—CR$_{325}$—NR$_{525}$R$_{725}$;
- —R$_{425}$—NR$_{825}$—CR$_{325}$—NR$_{925}$-Z-R$_{625}$-alkyl;
- —R$_{425}$—NR$_{825}$—CR$_{325}$—NR$_{925}$-Z-R$_{625}$-alkenyl;
- —R$_{425}$—NR$_{825}$—CR$_{325}$—NR$_{925}$-Z-R$_{625}$-aryl;
- —R$_{425}$—NR$_{825}$—CR$_{325}$—NR$_{925}$-Z-R$_{625}$-heteroaryl; and
- —R$_{425}$—NR$_{825}$—CR$_{325}$—NR$_{925}$-Z-R$_{625}$-heterocyclyl;

R$_{225}$ is selected from:
- -hydrogen;
- -alkyl;
- -alkenyl;
- -aryl;
- -heteroaryl;
- -heterocyclyl;
- -alkyl-Y-alkyl;
- -alkyl-Y-alkenyl;
- -alkyl-Y-aryl; and
- -alkyl or alkenyl substituted by one or more substituents selected from:
    - —OH;
    - -halogen;
    - —N(R$_{525}$)$_2$;
    - —CO—N(R$_{525}$)$_2$;
    - —CO—C$_{1-10}$ alkyl;
    - —CO—O—C$_{1-10}$ alkyl;
    - —N$_3$;
    - -aryl;
    - -heteroaryl;
    - -heterocyclyl;
    - —CO-aryl; and
    - —CO-heteroaryl;

each R$_{325}$ is =O or =S;
each R$_{425}$ is independently alkyl or alkenyl, which may be interrupted by one or more —O— groups;
each R$_{525}$ is independently H or C$_{1-10}$ alkyl;
R$_{625}$ is a bond, alkyl, or alkenyl, which may be interrupted by one or more —O— groups;
R$_{725}$ is H or C$_{1-10}$ alkyl which may be interrupted by a hetero atom, or R$_{725}$ can join with R$_{525}$ to form a ring;
R$_{825}$ is H, C$_{1-10}$ alkyl, or arylalkyl; or R$_{425}$ and R$_{825}$ can join together to form a ring;
R$_{925}$ is C$_{1-10}$ alkyl which can join together with R$_{825}$ to form a ring;
each Y is independently —O— or —S(O)$_{0-2}$—;
Z is a bond, —CO—, or —SO$_2$—;
v is 0 to 4; and
each R$_{25}$ present is independently selected C$_{1-10}$ alkyl, C$_{1-10}$ alkoxy, hydroxy, halogen, and trifluoromethyl;

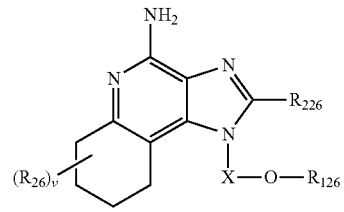

XXVI wherein: X is —CHR$_{526}$—, —CHR$_{526}$-alkyl-, or —CHR$_{526}$-alkenyl-;

R$_{126}$ is selected from:
- —R$_{426}$—NR$_{826}$—CR$_{326}$—NR$_{526}$-Z-R$_{626}$-alkyl;
- —R$_{426}$—NR$_{826}$—CR$_{326}$—NR$_{526}$-Z-R$_{626}$-alkenyl;
- —R$_{426}$—NR$_{826}$—CR$_{326}$—NR$_{526}$-Z-R$_{626}$-aryl;
- —R$_{426}$—NR$_{826}$—CR$_{326}$—NR$_{526}$-Z-R$_{626}$-heteroaryl;
- —R$_{426}$—NR$_{826}$—CR$_{326}$—NR$_{526}$-Z-R$_{626}$-heterocyclyl;
- —R$_{426}$—NR$_{826}$—CR$_{326}$—NR$_{526}$R$_{726}$;
- —R$_{426}$—NR$_{826}$—CR$_{326}$—NR$_{926}$-Z-R$_{626}$-alkyl;
- —R$_{426}$—NR$_{826}$—CR$_{326}$—NR$_{926}$-Z-R$_{626}$-alkenyl;
- —R$_{426}$—NR$_{826}$—CR$_{326}$—NR$_{926}$-Z-R$_{626}$-aryl;
- —R$_{426}$—NR$_{926}$—CR$_{326}$—NR$_{926}$-Z-R$_{626}$-heteroaryl; and
- —R$_{426}$—NR$_{826}$—CR$_{326}$—NR$_{926}$-Z-R$_{626}$-heterocyclyl;

R$_{226}$ is selected from:
- -hydrogen;
- -alkyl;
- -alkenyl;
- -aryl;
- -heteroaryl;
- -heterocyclyl;
- -alkyl-Y-alkyl;
- -alkyl-Y-alkenyl;
- -alkyl-Y-aryl; and
- -alkyl or alkenyl substituted by one or more substituents selected from:
    - —OH;
    - -halogen;
    - —N(R$_{526}$)$_2$;
    - —CO—N(R$_{526}$)$_2$;
    - —CO—C$_{1-10}$ alkyl;
    - —CO—O—C$_{1-10}$ alkyl;
    - —N$_3$;
    - -aryl;
    - -heteroaryl;
    - -heterocyclyl;
    - —CO-aryl; and
    - —CO-heteroaryl;

each R$_{326}$ is =O or =S;
each R$_{426}$ is independently alkyl or alkenyl, which may be interrupted by one or more —O— groups;
each R$_{526}$ is independently H or C$_{1-10}$ alkyl;
R$_{626}$ is a bond, alkyl, or alkenyl, which may be interrupted by one or more —O— groups;
R$_{726}$ is H or C$_{1-10}$ alkyl which may be interrupted by a hetero atom, or R$_{726}$ can join with R$_{526}$ to form a ring;
R$_{826}$ is H, C$_{1-10}$ alkyl, or arylalkyl; or R$_{426}$ and R$_{826}$ can join together to form a ring;
R$_{926}$ is C$_{1-10}$ alkyl which can join together with R$_{826}$ to form a ring;
each Y is independently —O— or —S(O)$_{0-2}$—;
Z is a bond, —CO—, or —SO$_2$—;

v is 0 to 4; and each $R_{26}$ present is independently selected from $C_{1-10}$ alkyl, $C_{1-10}$ alkoxy, hydroxy, halogen, and trifluoromethyl;

and pharmaceutically acceptable salts of any of the foregoing.

In another embodiment, the IRM compound can be chosen from 1H-imidazo[4,5-c]pyridin-4-amines defined by Formula XXVII below:

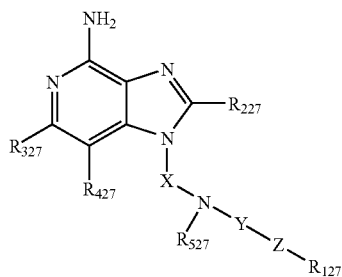

XXVII wherein X is alkylene or alkenylene;

Y is —CO— or —CS;

Z is a bond, —O—, or —S—;

$R_{127}$ is aryl, heteroaryl, heterocyclyl, alkyl or alkenyl, each of which may be unsubstituted or substituted by one or more substituents independently selected from:
- -alkyl;
- -alkenyl;
- -aryl;
- -heteroaryl;
- -heterocyclyl;
- -substituted cycloalkyl;
- -substituted aryl;
- -substituted heteroaryl;
- -substituted heterocyclyl;
- —O-alkyl;
- —O-(alkyl)$_{0-1}$-aryl;
- —O-(alkyl)$_{0-1}$-(substituted aryl);
- —O-(alkyl)$_{0-1}$-heteroaryl;
- —O-(alkyl)$_{0-1}$-(substituted heteroaryl);
- —O-(alkyl)$_{0-1}$-heterocyclyl;
- —O-(alkyl)$_{0-1}$-(substituted heterocyclyl);
- —COOH;
- —CO—O-alkyl;
- —CO-alkyl;
- —S(O)$_{0-2}$-alkyl;
- —S(O)$_{0-2}$-(alkyl)$_{0-1}$-aryl;
- —S(O)$_{0-2}$-(alkyl)$_{0-1}$-(substituted aryl);
- —S(O)$_{0-2}$-(alkyl)$_{0-1}$-heteroaryl;
- —S(O)$_{0-2}$-(alkyl)$_{0-1}$-(substituted heteroaryl);
- —S(O)$_{0-2}$-(alkyl)$_{0-1}$-heterocyclyl;
- —S(O)$_{0-2}$-(alkyl)$_{0-1}$-(substituted heterocyclyl);
- -(alkyl)$_{0-1}$-N(R$_{627}$)$_2$;
- -(alkyl)$_{0-1}$-NR$_{627}$—CO—O-alkyl;
- -(alkyl)$_{0-1}$-NR$_{627}$—CO-alkyl;
- -(alkyl)$_{0-1}$-NR$_{627}$—CO-aryl;
- -(alkyl)$_{0-1}$-NR$_{627}$—CO-(substituted aryl);
- -(alkyl)$_{0-1}$-N$_{627}$—CO-heteroaryl;
- -(alkyl)$_{0-1}$-NR$_{627}$—CO-(substituted heteroaryl);
- —N$_3$;
- -halogen;
- -haloalkyl;
- -haloalkoxy;
- —CO-haloalkyl;
- —CO-haloalkoxy;
- —NO$_2$;
- CN;
- —OH;
- —SH; and in the case of alkyl, alkenyl, and heterocyclyl, oxo;

$R_{227}$ is selected from:
- -hydrogen;
- -alkyl;
- -alkenyl;
- -aryl;
- -substituted aryl;
- -heteroaryl;
- -substituted heteroaryl;
- -alkyl-O-alkyl;
- -alkyl-S-alkyl;
- -alkyl-O-aryl;
- -alkyl-S-aryl:
- -alkyl-O-alkenyl;
- -alkyl-S-alkenyl; and
- -alkyl or alkenyl substituted by one or more substituents selected from:
  - —OH;
  - -halogen;
  - —N(R$_{627}$)$_2$;
  - —CO—N(R$_{627}$)$_2$;
  - —CS—N(R$_{627}$)$_2$;
  - —SO$_2$—N(R$_{627}$)$_2$;
  - —NR$_{627}$—CO—C$_{1-10}$ alkyl;
  - —NR$_{627}$—CS—C$_{1-10}$ alkyl;
  - —NR$_{627}$—SO$_2$—C$_{1-10}$ alkyl;
  - —CO—C$_{1-10}$ alkyl;
  - —CO—O—C$_{1-10}$ alkyl;
  - —N$_3$;
  - -aryl;
  - -substituted aryl;
  - -heteroaryl;
  - -substituted heteroaryl;
  - -heterocyclyl;
  - -substituted heterocyclyl;
  - —CO-aryl;
  - —CO-(substituted aryl);
  - —CO-heteroaryl; and
  - —CO-(substituted heteroaryl);

$R_{327}$ and $R_{427}$ are independently selected from hydrogen, alkyl, alkenyl, halogen, alkoxy, amino, alkylamino, dialkylamino, and alkylthio;

$R_{527}$ is H or $C_{1-10}$ alkyl, or $R_{527}$ can join with X to form a ring that contains one or two heteroatoms; or when $R_{127}$ is alkyl, $R_{527}$ and $R_{127}$ can join to form a ring;

each $R_{627}$ is independently H or $C_{1-10}$alkyl;

and pharmaceutically acceptable salts thereof.

In another embodiment, the IRM compound can be chosen from 1H-imidazo[4,5-c]pyridin-4-amines defined by Formula XXVIII below:

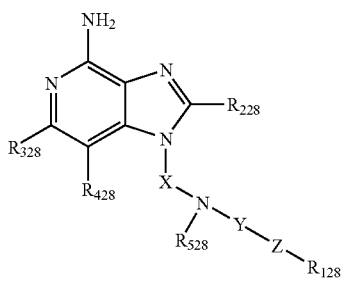

wherein X is alkylene or alkenylene;
Y is —SO$_2$—;
Z is a bond or —NR$_{628}$—;
R$_{128}$ is aryl, heteroaryl, heterocyclyl, alkyl or alkenyl, each of which may be unsubstituted or substituted by one or more substituents independently selected from:
-alkyl;
-alkenyl;
-aryl;
-heteroaryl;
-heterocyclyl;
-substituted cycloalkyl;
-substituted aryl;
-substituted heteroaryl;
-substituted heterocyclyl;
—O-alkyl;
—O-(alkyl)$_{0-1}$-aryl;
—O-(alkyl)$_{0-1}$-(substituted aryl);
—O-(alkyl)$_{0-1}$-heteroaryl;
—O-(alkyl)$_{0-1}$-(substituted heteroaryl);
—O-(alkyl)$_{0-1}$-heterocyclyl;
—O-(alkyl)$_{0-1}$-(substituted heterocyclyl);
—COOH;
—CO—O-alkyl;
—CO-alkyl;
—S(O)$_{0-2}$-alkyl;
—S(O)$_{0-2}$-(alkyl)$_{0-1}$-aryl;
—S(O)$_{0-2}$-(alkyl)$_{0-1}$-(substituted aryl);
—S(O)$_{0-2}$-(alkyl)$_{0-1}$-heteroaryl;
—S(O)$_{0-2}$-(alkyl)$_{0-1}$-(substituted heteroaryl);
—S(O)$_{0-2}$-(alkyl)$_{0-1}$-heterocyclyl;
—S(O)$_{0-2}$-(alkyl)$_{0-1}$-(substituted heterocyclyl);
-(alkyl)$_{0-1}$-N(R$_{628}$)$_2$;
-(alkyl)$_{0-1}$-NR$_{628}$—CO—O-alkyl;
-(alkyl)$_{0-1}$-NR$_{628}$—CO-alkyl;
-(alkyl)$_{0-1}$-NR$_{628}$—CO-aryl;
-(alkyl)$_{0-1}$-NR$_{628}$—CO-(substituted aryl);
-(alkyl)$_{0-1}$-NR$_{628}$—CO-heteroaryl;
-(alkyl)$_{0-1}$-NR$_{628}$—CO-(substituted heteroaryl);
N$_3$;
-halogen;
-haloalkyl;
-haloalkoxy;
—CO-haloalkyl;
—CO-haloalkoxy;
—NO$_2$;
—CN;
—OH;
—SH; and in the case of alkyl, alkenyl, and heterocyclyl, oxo;
R$_{228}$ is selected from:
-hydrogen;
-alkyl;
-alkenyl;
-aryl;
-substituted aryl;
-heteroaryl;
-substituted heteroaryl;
-alkyl-O-alkyl;
-alkyl-S-alkyl;
-alkyl-O-aryl;
-alkyl-S-aryl:
-alkyl-O-alkenyl;
-alkyl-S-alkenyl; and
-alkyl or alkenyl substituted by one or more substituents selected from:
—OH;
-halogen;
—N(R$_{628}$)$_2$;
—CO—N(R$_{628}$)$_2$;
—CS—N(R$_{628}$)$_2$;
—SO$_2$—N(R$_{628}$)$_2$;
—NR$_{628}$—CO—C$_{1-10}$ alkyl;
—NR$_{628}$—CS—C$_{1-10}$ alkyl;
—NR$_{628}$—SO$_2$—C$_{1-10}$ alkyl;
—CO—C$_{1-10}$ alkyl;
—CO—O—C$_{1-10}$ alkyl;
—N$_3$;
-aryl;
-substituted aryl;
-heteroaryl;
-substituted heteroaryl;
-heterocyclyl;
-substituted heterocyclyl;
—CO-aryl;
—CO-(substituted aryl);
—CO-heteroaryl; and
—CO-(substituted heteroaryl);
R$_{328}$ and R$_{428}$ are independently selected from hydrogen, alkyl, alkenyl, halogen, alkoxy, amino, alkylamino, dialkylamino, and alkylthio;
R$_{528}$ is H or C$_{1-10}$ alkyl, or R$_{528}$ can join with X to form a ring; or when R$_{128}$ is alkyl, R$_{528}$ and R$_{128}$ can join to form a ring;
each R$_{628}$ is independently H or C$_{1-10}$alkyl;
and pharmaceutically acceptable salts thereof.

In another embodiment, the IRM compound can be chosen from 1H-imidazo[4,5-c]pyridin-4-amines defined by Formula XXIX below:

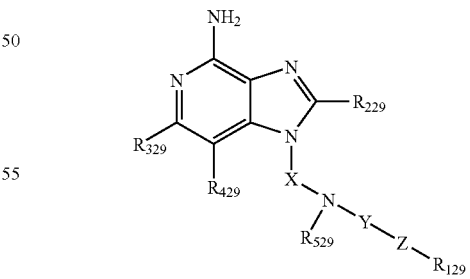

wherein X is alkylene or alkenylene;
Y is —CO— or —CS;
Z is —NR$_{629}$—, —NR$_{629}$—CO—, —NR$_{629}$—SO$_2$—, or —NR$_{729}$—;
R$_{129}$ is aryl, heteroaryl, heterocyclyl, alkyl or alkenyl, each of which may be unsubstituted or substituted by one or more substituents independently selected from:

-alkyl;
-alkenyl;
-aryl;
-heteroaryl;
-heterocyclyl;
-substituted cycloalkyl;
-substituted aryl;
-substituted heteroaryl;
-substituted heterocyclyl;
—O-alkyl;
—O-(alkyl)$_{0-1}$-aryl;
—O-(alkyl)$_{0-1}$-(substituted aryl);
—O-(alkyl)$_{0-1}$-heteroaryl;
—O-(alkyl)$_{0-1}$-(substituted heteroaryl);
—O-(alkyl)$_{0-1}$-heterocyclyl;
—O-(alkyl)$_{0-1}$-(substituted heterocyclyl);
—COOH;
—CO—O-alkyl;
—CO-alkyl;
—S(O)$_{0-2}$-alkyl;
—S(O)$_{0-2}$-(alkyl)$_{0-1}$-aryl;
—S(O)$_{0-2}$-(alkyl)$_{0-1}$-(substituted aryl);
—S(O)$_{0-2}$-(alkyl)$_{0-1}$-heteroaryl;
—S(O)$_{0-2}$-(alkyl)$_{0-1}$-(substituted heteroaryl);
—S(O)$_{0-2}$-(alkyl)$_{0-1}$-heterocyclyl;
—S(O)$_{0-2}$-(alkyl)$_{0-1}$-(substituted heterocyclyl);
-(alkyl)$_{0-1}$-N(R$_{629}$)$_2$;
-(alkyl)$_{0-1}$-NR$_{629}$—CO—O-alkyl;
-(alkyl)$_{0-1}$-NR$_{629}$—CO-alkyl;
-(alkyl)$_{0-1}$-NR$_{629}$—CO-aryl;
-(alkyl)$_{0-1}$-NR$_{629}$—CO-(substituted aryl);
-(alkyl)$_{0-1}$-NR$_{629}$—CO-heteroaryl;
-(alkyl)$_{0-1}$-NR$_{629}$—CO-(substituted heteroaryl);
P(O)(O-alkyl)$_2$;
—N$_3$;
-halogen;
-haloalkyl;
-haloalkoxy;
—CO-haloalkyl;
—CO-haloalkoxy;
—NO$_2$;
—CN;
—OH;
—SH; and in the case of alkyl, alkenyl, and heterocyclyl, oxo;
R$_{229}$ is selected from:
-hydrogen;
-alkyl;
-alkenyl;
-aryl;
-substituted aryl;
-heteroaryl;
-substituted heteroaryl;
-alkyl-O-alkyl;
-alkyl-S-alkyl;
-alkyl-O-aryl;
-alkyl-S-aryl:
-alkyl-O-alkenyl;
-alkyl-S-alkenyl; and
-alkyl or alkenyl substituted by one or more substituents selected from:
—OH;
-halogen;
—N(R$_{629}$)$_2$;
—CO—N(R$_{629}$)$_2$;
—CS—N(R$_{629}$)$_2$;
—SO$_2$—N(R$_{629}$)$_2$;
—NR$_{629}$—CO—C$_{1-10}$ alkyl;
—NR$_{629}$—CS—C$_{1-10}$ alkyl;
—NR$_{629}$—SO$_2$—C$_{1-10}$ alkyl;
—CO—C$_{1-10}$ alkyl;
—CO—O—C$_{1-10}$ alkyl;
—N$_3$;
-aryl;
-substituted aryl;
-heteroaryl;
-substituted heteroaryl;
-heterocyclyl;
-substituted heterocyclyl;
—CO-aryl;
—CO-(substituted aryl);
—CO-heteroaryl; and
—CO-(substituted heteroaryl);

R$_{329}$ and R$_{429}$ are independently selected from hydrogen, alkyl, alkenyl, halogen, alkoxy, amino, alkylamino, dialkylamino, and alkylthio;

R$_{529}$ is H or C$_{1-10}$ alkyl, or R$_{529}$ can join with X to form a ring that contains one or two heteroatoms;

each R$_{629}$ is independently H or C$_{1-10}$alkyl;

R$_{729}$ is H or C$_{1-10}$ alkyl which may be interrupted by a heteroatom; or when R$_{129}$ is alkyl, R$_{729}$ and R$_{129}$ can join to form a ring;

and pharmaceutically acceptable salts thereof.

In another embodiment, the IRM compound can be chosen from 1-position ether or thioether substituted 1H-imidazo[4,5-c]pyridin-4-amines defined by Formula XXX below:

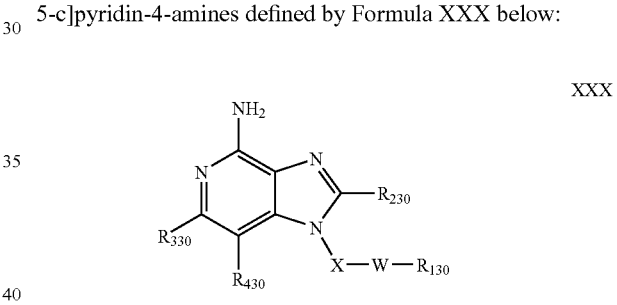

wherein:
X is —CH(R$_{530}$)—, —CH(R$_{530}$)-alkylene-, —CH(R$_{530}$)-alkenylene-, or CH(R$_{530}$)-alkylene-Y-alkylene-;
Y is —O—, or —S(O)$_{0-2}$—;
—W—R$_{130}$ is selected from —O—R$_{130-1-5}$ and —S(O)$_{0-2}$—R$_{130-6}$;
R$_{130-1-5}$ is selected from
—R$_{630}$—C(R$_{730}$)-Z-R$_{830}$-alkyl;
—R$_{630}$—C(R$_{730}$)-Z-R$_{830}$-alkenyl;
—R$_{630}$—C(R$_{730}$)-Z-R$_{830}$-aryl;
—R$_{630}$—C(R$_{730}$)-Z-R$_{830}$-heteroaryl;
—R$_{630}$—C(R$_{730}$)-Z-R$_{530}$-heterocyclyl;
—R$_{630}$—C(R$_{730}$)-Z-H;
—R$_{630}$—N(R$_{930}$)—C(R$_{730}$)—R$_{830}$-alkyl;
—R$_{630}$—N(R$_{930}$)—C(R$_{730}$)—R$_{830}$-alkenyl;
—R$_{630}$—N(R$_{930}$)—C(R$_{730}$)—R$_{830}$-aryl;
—R$_{630}$—N(R$_{930}$)—C(R$_{730}$)—R$_{830}$-heteroaryl;
—R$_{630}$—N(R$_{930}$)—C(R$_{730}$)—R$_{830}$-heterocyclyl;
—R$_{630}$—N(R$_{930}$)—C(R$_{730}$)—R$_{1030}$;
—R$_{630}$—N(R$_{930}$)—SO$_2$—R$_{530}$-alkyl;
—R$_{630}$—N(R$_{930}$)—SO$_2$—R$_{830}$-alkenyl;
—R$_{630}$—N(R$_{930}$)—SO$_2$—R$_{830}$-aryl;
R$_{630}$—N(R$_{930}$)—SO$_2$—R$_{830}$-heteroaryl;
—R$_{630}$—N(R$_{930}$)—SO$_2$—R$_{830}$-heterocyclyl;
—R$_{630}$—N(R$_{930}$)—SO$_2$—R$_{1030}$;
—R$_{630}$—N(R$_{930}$)—SO$_2$—N(R$_{530}$)—R$_{830}$-alkyl;

—$R_{630}$—N($R_{930}$)—SO$_2$—N($R_{530}$)—$R_{830}$-alkenyl;
—$R_{630}$—N($R_{930}$)—SO$_2$—N($R_{530}$)—$R_{830}$-aryl;
—$R_{630}$—N($R_{930}$)—SO$_2$—N($R_{530}$)—$R_{830}$-heteroaryl;
$R_{630}$—N($R_{930}$)—SO$_2$—N($R_{530}$)—$R_{830}$-heterocyclyl;
—$R_{630}$—N($R_{930}$)—SO$_2$—NH$_2$;
—$R_{630}$—N($R_{930}$)—C($R_{730}$)—N($R_{530}$)-Q-$R_{830}$-alkyl;
$R_{630}$—N($R_{930}$)—C($R_{730}$)—N($R_{530}$)-Q-$R_{530}$-alkenyl;
—$R_{630}$—N($R_{930}$)—C($R_{730}$)—N($R_{530}$)-Q-$R_{830}$-aryl;
—$R_{630}$—N($R_{930}$)—C($R_{730}$)—N($R_{530}$)-Q-$R_{830}$-heteroaryl;
—$R_{630}$—N($R_{930}$)—C($R_{730}$)—N($R_{530}$)-Q-$R_{830}$-heterocyclyl;
—$R_{630}$—N($R_{930}$)—C($R_{730}$)—N($R_{530}$)$_2$;

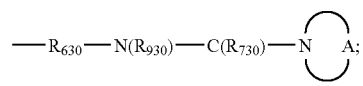

—$R_{630}$—N($R_{930}$)—C($R_{730}$)—N($R_{1130}$)-Q-$R_{830}$-alkyl;
—$R_{630}$—N($R_{930}$)—C($R_{730}$)—N($R_{1130}$)-Q-$R_{830}$-alkenyl;
—$R_{630}$—N($R_{930}$)—C($R_{730}$)—N($R_{1130}$)-Q-$R_{830}$-aryl;
—$R_{630}$—N($R_{930}$)—C($R_{730}$)—N($R_{1130}$)-Q-$R_{830}$-heteroaryl;
—$R_{630}$—N($R_{930}$)—C($R_{730}$)—N($R_{1130}$)-Q-$R_{830}$-heterocyclyl;
—$R_{630}$—N($R_{930}$)—C($R_{730}$)—N($R_{1130}$)H;
-alkenyl;
-aryl;
—$R_{630}$-aryl;
-heteroaryl;
-heterocyclyl;
—$R_{630}$-heteroaryl; and
—$R_{630}$-heterocyclyl;

Z is —N($R_{530}$)—, —O—, or —S—;
Q is a bond, —CO—, or —SO$_2$—;
A represents the atoms necessary to provide a 5- or 6-membered heterocyclic or heteroaromatic ring that contains up to three heteroatoms;
$R_{130\text{-}6}$ is selected from:
-alkyl;
-aryl;
-heteroaryl;
-heterocyclyl;
-alkenyl;
—$R_{630}$-aryl;
—$R_{630}$-heteroaryl; and
—$R_{630}$-heterocyclyl;
each $R_{530}$ is independently hydrogen, C$_{1-10}$ alkyl, or C$_{2-10}$ alkenyl;
$R_{630}$ is alkylene, alkenylene, or alkynylene, which may be interrupted by one or more —O— groups;
$R_{730}$ is =O or =S;
$R_{830}$ is a bond, alkylene, alkenylene, or alkynylene, which may be interrupted by one or more —O— groups;
$R_{930}$ is hydrogen, C$_{1-10}$ alkyl, or arylalkyl; or $R_{930}$ can join together with any carbon atom of $R_{630}$ to form a ring of the formula

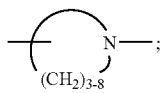

$R_{1030}$ is hydrogen or C$_{1-10}$ alkyl; or $R_{930}$ and $R_{1030}$ can join together to form a ring selected from

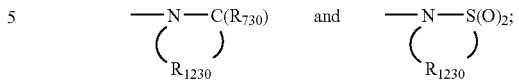

$R_{1130}$ is C$_{1-10}$ alkyl; or $R_{930}$ and $R_{1130}$ can join together to form a ring having the structure

$R_{1230}$ is C$_{2-7}$ alkylene which is straight chain or branched, wherein the branching does not prevent formation of the ring; and
$R_{230}$, $R_{330}$ and $R_{430}$ are independently selected from hydrogen and non-interfering substitutents;
and pharmaceutically acceptable salts thereof.
Illustrative non-interfering $R_{230}$ substitutents include:
-alkyl;
-alkenyl;
-aryl;
-heteroaryl;
-heterocyclyl;
-alkylene-Y-alkyl;
-alkylene-Y-alkenyl;
-alkylene-Y-aryl; and
-alkyl or alkenyl substituted by one or more substituents selected from the group consisting of:
—OH;
-halogen;
—N($R_{530}$)$_2$;
—C(O)—C$_{1-10}$ alkyl;
—C(O)—O—C$_{1-10}$ alkyl;
—N$_3$;
-aryl;
-heteroaryl;
-heterocyclyl;
—C(O)-aryl; and
—C(O)-heteroaryl.
Illustrative non-interfering $R_{330}$ and $R_{430}$ substitutents include:
C$_{1-10}$ alkyl, C$_{2-10}$ alkenyl, C$_{2-10}$ alkynyl, C$_{1-10}$ alkoxy, C$_{1-10}$ alkylthio, amino, alkylamino, dialkylamino, halogen, and nitro.
In another embodiment, the IRM compound can be chosen from 1H-imidazo dimers of the formula (XXXI):

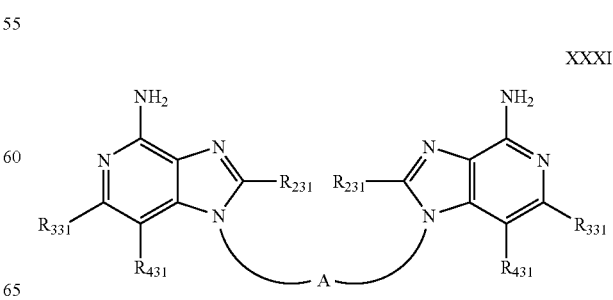

wherein:
A is a divalent linking group selected from the group consisting of:
straight or branched chain $C_{4-20}$ alkylene;
straight or branched chain $C_{4-20}$ alkenylene;
straight or branched chain $C_{4-20}$ alkynylene; and
-Z-Y—W—Y-Z-;
each Z is independently selected from the group consisting of:
straight or branched chain $C_{2-20}$ alkylene;
straight or branched chain $C_{4-20}$ alkenylene; and
straight or branched chain $C_{4-20}$ alkynylene;
any of which may be optionally interrupted by —O—, —N($R_{531}$)—, or —S(O)$_2$—;
each Y is independently selected from the group consisting of:
a bond;
—N($R_{531}$)C(O)—;
—C(O)N($R_{531}$)—;
—N($R_{531}$)C(O)N($R_{531}$)—;
N($R_{531}$)S(O)$_2$—;
—S(O)$_2$N($R_{531}$)—;
—OC(O)O—;
—OC(O)—;
—C(O)O—;
—N($R_{531}$)C(O)O—; and
—OC(O)N($R_{531}$)—;
W is selected from the group consisting of:
straight or branched chain $C_{2-20}$ alkylene;
straight or branched chain $C_{2-20}$ alkenylene;
straight or branched chain $C_{4-20}$ alkynylene;
straight or branched chain perfluoro $C_{2-20}$ alkylene;
$C_{1-4}$ alkylene-O—$C_{1-4}$ alkylene;
—C(O)—;
—S(O)$_2$—;
—OC(O)O—;
—N($R_{551}$)C(O)N($R_{531}$)—;

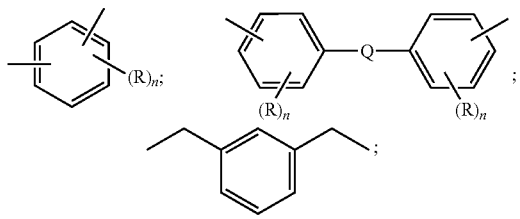

1,5-naphthylene;
2,6-pyridinylene;
1,2-cyclohexylene;
1,3-cyclohexylene;
1,4-cyclohexylene;
trans-1,4-cyclohexylene;

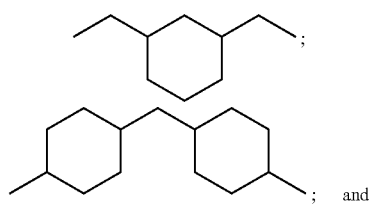
; and trans-5-norbornen-2,3-diyl;
wherein n is 0-4; each R is independently selected from the group consisting of $C_{1-4}$ alkyl, $C_{1-4}$ alkoxy, and halogen; and Q is selected from the group consisting of a bond, —CH$_2$—, and —O—;
$R_{231}$ is selected from the group consisting of:
hydrogen;
-alkyl;
-alkenyl;
-aryl;
-substituted aryl;
-heteroaryl;
-substituted heteroaryl;
-alkyl-X-alkyl;
-alkyl-X-aryl;
-alkyl-X-alkenyl; and
-alkyl or alkenyl substituted by one or more substituents selected from the group consisting of:
—OH;
-halogen;
—N($R_{631}$)$_2$;
—C(O)—N($R_{631}$)$_2$;
—C(S)—N($R_{631}$)$_2$;
—S(O)$_2$—N($R_{631}$)$_2$;
—N($R_{631}$)—C(O)—$C_{1-10}$ alkyl;
—N($R_{631}$)—C(S)—$C_{1-10}$ alkyl;
—N($R_{631}$)—S(O)$_2$—$C_{1-10}$ alkyl;
—C(O)—$C_{1-10}$ alkyl;
—C(O)—O—$C_{1-10}$ alkyl;
—N$_3$;
-aryl;
-substituted aryl;
-heteroaryl;
-substituted heteroaryl;
-heterocyclyl;
-substituted heterocyclyl;
—C(O)-aryl;
—C(O)-(substituted aryl);
—C(O)-heteroaryl; and
—C(O)-(substituted heteroaryl);
$R_{331}$ and $R_{431}$ are each independently selected from the group consisting of:
-hydrogen;
-halogen;
-alkyl;
-alkenyl;
—X-alkyl; and
—N($R_{631}$)$_2$;
or when taken together, $R_{331}$ and $R_{431}$ form a fused aryl or heteroaryl ring that is unsubstituted or substituted by one or more substituents selected from the group consisting of:
-halogen;
-alkyl;
-alkenyl;
—X-alkyl; and
—NR$_{631}$)$_2$;
or when taken together, $R_{331}$ and $R_{431}$ form a fused 5 to 7 membered saturated ring, containing 0 to 2 heteroatoms and unsubstituted or substituted by one or more substituents selected from the group consisting of:
-halogen;
-alkyl;
-alkenyl;
—X-alkyl; and
—N($R_{631}$)$_2$;

each $R_{531}$ is independently selected from the group consisting of:
hydrogen;
$C_{1-6}$ alkyl;
$C_{3-7}$ cycloalkyl; and
benzyl; or
when Y is —N($R_{531}$)C(O)—, —C(O)N($R_{531}$)—, —N($R_{531}$)C(O)N($R_{531}$)—, —N($R_{531}$)S(O)$_2$—, —S(O)$_2$N($R_{531}$)—, —N($R_{531}$)C(O)O—, or —OC(O)N($R_{531}$)— and the nitrogen of the N($R_{531}$) group is bonded to Z, then $R_{531}$ can join with Z to form a ring having the structure

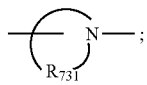

each $R_{631}$ is independently hydrogen or $Cl_{1-10}$ alkyl;
$R_{731}$ is $C_{3-8}$ alkylene; and
X is —O— or —S—;
with the proviso that if W is —C(O)—, —S(O)$_2$—, —OC(O)O—, or —N($R_{531}$)C(O)N($R_{531}$)— then each Y is a bond;
and pharmaceutically acceptable salts thereof.

In another embodiment, the IRM compound can be chosen from 6-, 7-, 8-, or 9-position aryl or heteroaryl substituted 1H-imidazo[4,5-c]quinolin-4-amines of the following Formula (XXXII):

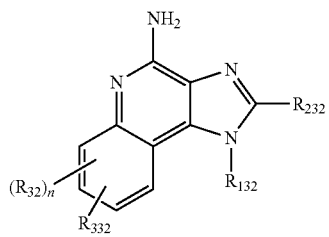

wherein:
$R_{32}$ is selected from the group consisting of alkyl, alkoxy, hydroxy, and trifluoromethyl;
n is 0 or 1;
$R_{132}$ and $R_{232}$ are independently selected from the group consisting of hydrogen and non-interfering substitutents;
$R_{332}$ is selected from the group consisting of:
-Z-Ar,
-Z-Ar'—Y—$R_{432}$,
-Z-Ar'—X—Y—$R_{432}$,
-Z-Ar'—$R_{532}$, and
-Z-Ar'—X—$R_{532}$;
Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkoxy, heteroaryl, heteroaryloxy, heteroarylalkoxy, heterocyclyl, heterocyclylalkyl, amino, alkylamino, and dialkylamino;
Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkoxy, heteroaryl, heteroaryloxy, heteroarylalkoxy, heterocyclyl, heterocyclylalkyl, amino, alkylamino, and dialkylamino;

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;
Y is selected from the group consisting of:
—S(O)$_{0-2}$—,
—S(O)$_2$—N($R_{832}$)—,
—C($R_{632}$)—,
—C($R_{632}$)—O—,
—O—C($R_{632}$)—,
—O—C(O)—O—,
—N($R_{832}$)-Q-,
—C($R_{632}$)—N($R_{832}$)—,
—O—C($R_{632}$)—N($R_{532}$)—,
—C($R_{632}$)—N(O$R_{932}$)—,

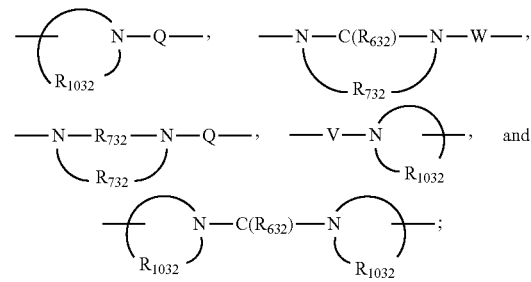

Z is selected from the group consisting of a bond, alkylene, alkenylene, and alkynylene;
$R_{432}$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;
$R_{532}$ is selected from the group consisting of:

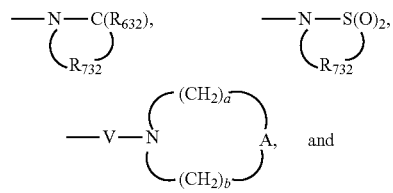

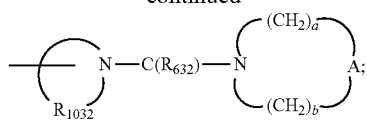

each $R_{632}$ is independently selected from the group consisting of =O and =S;

each $R_{732}$ is independently $C_{2-7}$ alkylene;

each $R_{832}$ is independently selected from the group consisting of hydrogen, alkyl, alkoxyalkylenyl, and arylalkylenyl;

$R_{932}$ is selected from the group consisting of hydrogen and alkyl;

each $R_{1032}$ is independently $C_{3-8}$ alkylene;

A is selected from the group consisting of —O—, —C(O)—, —S(O)$_{0-2}$—, —CH$_2$—, and —N(R$_{432}$)—;

Q is selected from the group consisting of a bond, —C(R$_{632}$)—, —C(R$_{632}$)—C(R$_{632}$), —S(O)$_2$—, —C(R$_{632}$)—N(R$_{832}$)—W—, —S(O)$_2$—N(R$_{832}$)—, —C(R$_{632}$)—O—, and —C(R$_{632}$)—N(OR$_{932}$)—;

V is selected from the group consisting of —C(R$_{632}$)—, —O—C(R$_{632}$)—, —N(R$_{832}$)—C(R$_{632}$)—, and —S(O)$_2$—;

W is selected from the group consisting of a bond, —C(O)—, and —S(O)$_2$—; and a and b are independently integers from 1 to 6 with the proviso that a+b is ≦7;

and pharmaceutically acceptable salts thereof.

Illustrative non-interfering $R_{132}$ substituents include:
—R$_{432}$,
—X—R$_{432}$,
—X—Y—R$_{432}$,
—X—Y—X—Y—R$_{432}$, and
—X—R$_{532}$;

wherein:

each X is independently selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

each Y is independently selected from the group consisting of:
—S(O)$_{0-2}$—,
—S(O)$_2$—N(R$_{832}$)—,
—C(R$_{632}$)—,
—C(R$_{632}$)—O—,
—O—C(R$_{632}$)—,
—O—C(O)—O—,
—N(R$_{832}$)-Q-,
—C(R$_{632}$)—N(R$_{832}$)—,
O—C(R$_{632}$)—N(R$_{832}$)—,
—C(R$_{632}$)—N(OR$_{932}$)—,

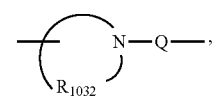

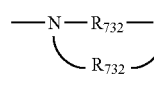

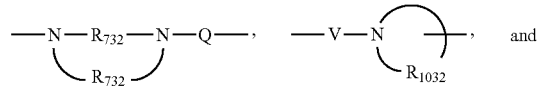

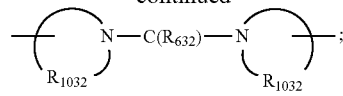

$R_{432}$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_{532}$ is selected from the group consisting of:

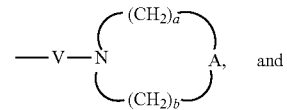

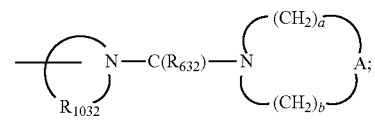

each $R_{632}$ is independently selected from the group consisting of =O and =S;

each $R_{732}$ is independently $C_{2-7}$ alkylene;

each $R_{832}$ is independently selected from the group consisting of hydrogen, alkyl, alkoxyalkylenyl, and arylalkylenyl;

each $R_{932}$ is independently selected from the group consisting of hydrogen and alkyl;

each $R_{1032}$ is independently $C_{3-8}$ alkylene;

A is selected from the group consisting of —O—, —C(O)—, —S(O)$_{0-2}$—, —CH$_2$—, and —N(R$_{432}$)—;

each Q is independently selected from the group consisting of a bond, —C(R$_{632}$)—, —C(R$_{632}$)—C(R$_{632}$)—, —S(O)$_2$—, —C(R$_{632}$)—N(R$_{832}$)—W—, —S(O)$_2$—N(R$_{832}$)—, —C(R$_{632}$)—O—, and —C(R$_{632}$)—N(OR$_{932}$)—;

each V is independently selected from the group consisting of —C(R$_{632}$)—, —O—C(R$_{632}$)—, —N(R$_{832}$)—C(R$_{632}$)—, and —S(O)$_2$—;

each W is independently selected from the group consisting of a bond, —C(O)—, and —S(O)$_2$—; and a and b are independently integers from 1 to 6 with the proviso that a+b is ≦7;

Illustrative non-interfering $R_{232}$ substituents include:
—R$_{432}$,
—X—R$_{432}$,
—X—Y—R$_{432}$, and
—X—R$_{532}$;

wherein:

X is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y is selected from the group consisting of:
—S(O)$_{0-2}$—,
—S(O)$_2$—N(R$_{832}$)—,
—C(R$_{632}$)—,
—C(R$_{632}$)—O—,
—O—C(R$_{632}$)—,
—O—C(O)—O—,
N(R$_{832}$)-Q-,
—C(R$_{632}$)—N(R$_{832}$)—,
—O—C(R$_{632}$)—N(R$_{832}$)—,
—C(R$_{632}$)—N(OR$_{932}$)—,

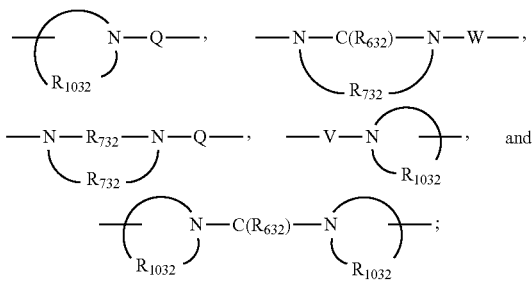

R$_{432}$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_{532}$ is selected from the group consisting of:

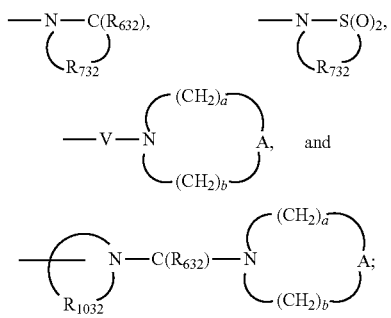

each R$_{632}$ is independently selected from the group consisting of =O and =S;
each R$_{732}$ is independently C$_{2-7}$ alkylene;
each R$_{832}$ is independently selected from the group consisting of hydrogen, alkyl, alkoxyalkylenyl, and arylalkylenyl;

R$_{932}$ is selected from the group consisting of hydrogen and alkyl;
each R$_{1032}$ is independently C$_{3-8}$ alkylene;
A is selected from the group consisting of —O—, —C(O)—, —S(O)$_{0-2}$—, —CH$_2$—, and —N(R$_{432}$)—;
Q is selected from the group consisting of a bond, —C(R$_{632}$)—, —C(R$_{632}$)—C(R$_{632}$)—, —S(O)$_2$—, —C(R$_{632}$)—N(R$_{832}$)—W—, —S(O)$_2$—N(R$_{832}$)—, —C(R$_{632}$)—O—, and —C(R$_{632}$)—N(OR$_{932}$)—;
V is selected from the group consisting of —C(R$_{632}$)—, —O—C(R$_{632}$)—, —N(R$_{832}$)—C(R$_{632}$)—, and —S(O)$_2$—;
W is selected from the group consisting of a bond, —C(O)—, and —S(O)$_2$—; and
a and b are independently integers from 1 to 6 with the proviso that a+b is ≦7;

Herein, "non-interfering" means that the ability of the compound or salt to modulate (e.g., induce or inhibit) the biosynthesis of one or more cytokines is not destroyed by the non-interfering substituent.

As used herein, the terms "alkyl", "alkenyl", "alkynyl" and the prefix "alk-" are inclusive of both straight chain and branched chain groups and of cyclic groups, i.e. cycloalkyl and cycloalkenyl. Unless otherwise specified, these groups contain from 1 to 20 carbon atoms, with alkenyl and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene", "alkenylene", and "alkynylene" are the divalent forms of the "alkyl", "alkenyl", and "alkynyl" groups defined above. Likewise, "alkylenyl", "alkenylenyl", and "alkynylenyl" are the divalent forms of the "alkyl", "alkenyl", and "alkynyl" groups defined above. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. Similarly, the term "fluoroalkyl" is inclusive of groups that are substituted by one or more fluorine atoms, including perfluorinated groups (e.g., trifluoromethyl).

The term "aryl" as used herein includes carbocyclic aromatic rings or ring systems. Examples of aryl groups include phenyl, naphthyl, biphenyl, fluorenyl and indenyl.

The term "heteroatom" refers to the atoms O, S, or N.

The term "heteroaryl" includes aromatic rings or ring systems that contain at least one ring heteroatom (e.g., O, S, N). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, imidazolidinyl, isothiazolidinyl, tetrahydropyranyl, quinuclidinyl, homopiperidinyl, homopiperazinyl, and the like.

The terms "arylene," "heteroarylene," and "heterocyclylene" are the divalent forms of the "aryl," "heteroaryl," and "heterocyclyl" groups defined above. Likewise, "arylenyl," "heteroarylenyl," and "heterocyclylenyl" are the divalent forms of the "aryl," "heteroaryl," and "heterocyclyl" groups defined above. For example, an alkylarylenyl group comprises an arylene moiety to which an alkyl group is attached.

Unless otherwise specified, the aryl, heteroaryl, and heterocyclyl groups of Formulas IX-XXX can be unsubstituted or substituted by one or more substituents independently selected from the group consisting of alkyl, alkoxy, methylenedioxy, ethylenedioxy, alkylthio, haloalkyl, haloalkoxy, haloalkylthio, halogen, nitro, hydroxy, mercapto, cyano, carboxy, formyl, aryl, aryloxy, arylthio, arylalkoxy, arylalkylthio, heteroaryl, heteroaryloxy, heteroarylthio, heteroarylalkoxy, heteroarylalkylthio, amino, alkylamino, dialkylamino, heterocyclyl, heterocycloalkyl, alkylcarbonyl, alkenylcarbonyl, alkoxycarbonyl, haloalkylcarbonyl, haloalkoxycarbonyl, alkylthiocarbonyl, arylcarbonyl, heteroarylcarbonyl, heterocyclylcarbonyl, aryloxycarbonyl, heteroaryloxycarbonyl, arylthiocarbonyl, heteroarylthiocarbonyl, alkanoyloxy, alkanoylthio, alkanoylamino, aroyloxy, aroylthio, aroylamino, alkylaminosulfonyl, alkylsulfonyl, arylsulfonyl, heteroarylsulfonyl, aryldiazinyl, alkylsulfonylamino, arylsulfonylamino, arylalkylsulfonylamino, alkylcarbonylamino, alkenylcarbonylamino, arylcarbonylamino, arylalkylcarbonylamino, heteroarylcarbonylamino, heteroarylalkycarbonylamino, alkylsulfonylamino, alkenylsulfonylamino, arylsulfonylamino, arylalkylsulfonylamino, heteroarylsulfonylamino, heteroarylalkylsulfonylamino, alkylaminocarbonyl, dialkylaminocarbonyl, arylaminocarbonyl, arylalkylaminocarbonyl, alkenylaminocarbonyl, heteroarylaminocarbonyl, heteroarylalkylaminocarbonyl, alkylaminocarbonylamino, alkenylaminocarbonylamino, arylaminocarbonylamino, arylalkylaminocarbonylamino, heteroarylaminocarbonylamino, heteroarylalkylaminocarbonylamino and, in the case of heterocyclyl, oxo. If any other groups are identified as being "substituted" or "optionally substituted", then those groups can also be substituted by one or more of the above enumerated substituents.

When a group (or substituent or variable) is present more that once in any Formula described herein, each group (or substituent or variable) is independently selected, whether explicitly stated or not. For example, for the formula —N($R_{631}$)$_2$ each $R_{631}$ group is independently selected. In another example, when an $R_{232}$ and an $R_{332}$ group both contain an $R_{432}$ group, each $R_{432}$ group is independently selected. In a further example, when more than one Y group is present (i.e. $R_{232}$ and $R_{332}$ both contain a Y group) and each Y group contains one or more $R_{832}$ groups, then each Y group is independently selected, and each $R_{832}$ group is independently selected.

In certain embodiments, the immune response modifier is selected from the group consisting of imidazoquinoline amines, tetrahydroimidazoquinoline amines, imidazopyridine amines, 6,7-fused cycloalkylimidazopyridine amines, 1,2-bridged imidazoquinoline amines, imidazonaphthyridine amines, imidazotetrahydronaphthyridine amines, oxazoloquinoline amines, thiazoloquinoline amines, oxazolopyridine amines, thiazolopyridine amines, oxazolonaphthyridine amines, thiazolonaphthyridine amines, 1H-imidazo dimers fused to pyridine amines, quinoline amines, tetrahydroquinoline amines, naphthyridine amines, or tetrahydronaphthyridine amines, and combinations thereof.

In certain embodiments, the immune response modifier is selected from the group consisting of imidazoquinoline amines, tetrahydroimidazoquinoline amines, imidazopyridine amines, and combinations thereof.

In certain embodiments, the immune response modifier is selected from the group consisting of amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, 6-, 7-, 8-, or 9-aryl or heteroaryl substituted imidazoquinoline amines, amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, thioether substituted tetrahydroimidazoquinoline amines, amide substituted imidazopyridine amines, sulfonamide substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, thioether substituted imidazopyridine amines, and combinations thereof.

In certain embodiments, the immune response modifier is selected from the group consisting of amide substituted imidazoquinoline amines, sulfonamide substituted imidazoquinoline amines, urea substituted imidazoquinoline amines, thioether substituted imidazoquinoline amines, 7-aryl substituted imidazoquinoline amines, 7-heteroaryl substituted imidazoquinoline amines, sulfonamide substituted tetrahydroimidazoquinoline amines, and combinations thereof.

In certain embodiments, the immune response modifier is a sulfonamide substituted imidazoquinoline amine.

In certain embodiments, the immune response modifier is selected from the group consisting of:

$N^1$-{4-[4-amino-2-(2-methoxyethyl)-6,7,8,9-tetrahydro-1H-imidazo[4,5-c]quinolin-1-yl]butyl}-4-fluoro-1-benzenesulfonamide, N-[3-(4-amino-2-butyl-1H-imidazo[4,5-c]quinolin-1-yl)propyl]morpholine-4-carboxamide, N-{3-[4-amino-2-(2-methoxyethyl)-1H-imidazo[4,5-c]quinolin-1-yl]-2,2-dimethylpropyl}-N'-phenylurea, N-{2-[4-amino-2-(ethoxymethyl)-1H-imidazo[4,5-c]quinolin-1-yl]-1,1-dimethylethyl}methanesulfonamide, 2-butyl-1-[2-(propylsulfonyl)ethyl]-1H-imidazo[4,5-c]quinolin-4-amine, N-{2-[4-amino-2-(ethoxymethyl)-1H-imidazo[4,5-c]quinolin-1-yl]-1,1-dimethylethyl}-2-ethoxyacetamide, N-{4-[4-amino-2-(cyclopropylmethyl)-1H-imidazo[4,5-c]quinolin-1-yl]butyl}methanesulfonamide, N-{2-[4-amino-2-(ethoxymethyl)-1H-imidazo[4,5-c]quinolin-1-yl]-1,1-dimethylethyl}-N'-cyclohexylurea, N-{2-[4-amino-2-(ethoxymethyl)-1H-imidazo[4,5-c]quinolin-1-yl]-1,1-dimethylethyl}cyclohexanecarboxamide, N-{2-[4-amino-2-(ethoxymethyl)-6,7,8,9-tetrahydro-1H-imidazo[4,5-c]quinolin-1-yl]-1,1-dimethylethyl}methanesulfonamide, N-[3-(4-amino-2-butyl-1H-imidazo[4,5-c]quinolin-1-yl)-2,
2-dimethylpropyl]methanesulfonamide,
N-[2-(4-amino-2-butyl-1H-imidazo[4,5-c]quinolin-1-yl)-1,
1-dimethylethyl]methanesulfonamide,
N-{2-[4-amino-2-(2-methoxyethyl)-6,7,8,9-tetrahydro-1H-
imidazo[4,5-c]quinolin-1-yl]-1,1-
dimethylethyl}methanesulfonamide,
1-[4-amino-7-(5-hydroxymethylpyridin-3-yl)-2-(2-meth-
oxyethyl)-1H-imidazo[4,5-c]quinolin-1-yl]-2-methylpro-
pan-2-ol,
1-[4-amino-7-(3-hydroxymethyphenyl)-2-(2-methoxy-
ethyl)-1H-imidazo[4,5-c]quinolin-1-yl]-2-methylpropan-
2-ol,
N-{3-[4-amino-1-(2-hydroxy-2-methylpropyl)-2-(methoxy-
ethyl)-1H-imidazo[4,5-c]quinolin-7-yl]
phenyl}methanesulfonamide,
{5-[4-amino-2-(2-methoxyethyl)-1-(2-methylpropyl)-1H-
imidazo[4,5-c]quinolin-7-yl]pyridin-3-yl}methanol,
1-[4-amino-2-(ethoxymethyl)-7-(pyridin-3-yl)-1H-imidazo
[4,5-c]quinolin-1-yl]-2-methylpropan-2-ol,
1-{4-amino-2-(ethoxymethyl)-7-[5-(hydroxymethyl)pyri-
din-3-yl]-1H-imidazo[4,5-c]quinolin-1-yl}-2-methylpro-
pan-2-ol,
N-(2-{4-amino-2-ethoxymethyl-7-[6-(methanesulfony-
lamino)hexyloxy]-1H-imidazo[4,5-c]quinolin-1-yl}-1,1-
dimethylethyl)methanesulfonamide,
N-(6-{[4-amino-2-ethoxymethyl-1-(2-methanesulfony-
lamino-2-methylpropyl)-1H-imidazo[4,5-c]quinolin-7-
yl]oxy}hexyl)acetamide,
N-[2-(4-amino-2-ethoxymethyl-1-propyl-1H-imidazo[4,5-
c]quinolin-7-yloxy)ethyl]methanesulfonamide,
1-[4-amino-2-(ethoxymethyl)-7-(1H-pyrazol-4-yl)-1H-imi-
dazo[4,5-c]quinolin-1-yl]-2-methylpropan-2-ol,
3-[4-amino-2-(ethoxymethyl)-7-(pyridin-3-yl)-1H-imidazo
[4,5-c]quinolin-1-yl]propane-1,2-diol,
and combinations thereof.

In certain embodiments, the immune response modifier is selected from the group consisting of:
N-[3-(4-amino-2-butyl-1H-imidazo[4,5-c]quinolin-1-yl)
propyl]morpholine-4-carboxamide,
N-{3-[4-amino-2-(2-methoxyethyl)-1H-imidazo[4,5-c]
quinolin-1-yl]-2,2-dimethylpropyl}-N'-phenylurea,
N-{2-[4-amino-2-(ethoxymethyl)-1H-imidazo[4,5-c]quino-
lin-1-yl]-1,1-dimethylethyl}methanesulfonamide,
2-butyl-1-[2-(propylsulfonyl)ethyl]-1H-imidazo[4,5-c]
quinolin-4-amine,
N-{2-[4-amino-2-(ethoxymethyl)-1H-imidazo[4,5-c]quino-
lin-1-yl]-1,1-dimethylethyl}-2-ethoxyacetamide,
N-{2-[4-amino-2-(ethoxymethyl)-1H-imidazo[4,5-c]quino-
lin-1-yl]-1,1-dimethylethyl}-N'-cyclohexylurea,
N-{2-[4-amino-2-(ethoxymethyl)-6,7,8,9-tetrahydro-1H-
imidazo[4,5-c]quinolin-1-yl]-1,1-
dimethylethyl}methanesulfonamide,
N-[2-(4-amino-2-butyl-1H-imidazo[4,5-c]quinolin-1-yl)-1,
1-dimethylethyl]methanesulfonamide,
N-{2-[4-amino-2-(2-methoxyethyl)-6,7,8,9-tetrahydro-1H-
imidazo[4,5-c]quinolin-1-yl]-1,1-
dimethylethyl}methanesulfonamide,
1-{4-amino-2-(ethoxymethyl)-7-[5-(hydroxymethyl)pyri-
din-3-yl]-1H-imidazo[4,5-c]quinolin-1-yl}-2-methylpro-
pan-2-ol,
N-(6-{[4-amino-2-ethoxymethyl-1-(2-methanesulfony-
lamino-2-methylpropyl)-1H-imidazo[4,5-c]quinolin-7-
yl]oxy}hexyl)acetamide,
and combinations thereof.

In certain embodiments, the immune response modifier is
N-{2-[4-amino-2-(ethoxymethyl)-1H-imidazo[4,5-c]quino-
lin-1-yl]-1,1-dimethylethyl}methanesulfonamide and phar-
maceutically acceptable salts thereof.

The IRM compounds and salts thereof described herein include any of their pharmaceutically acceptable forms, such as isomers (e.g., diastereomers and enantiomers), solvates, polymorphs, and the like. In particular, if a compound is optically active, the invention specifically includes the use of each of the compound's enantiomers as well as racemic combinations of the enantiomers.

The immune response modifier can, for example, be a salt of an acid selected from the group consisting of a carboxylic acid, a halo acid, sulfuric acid, phosphoric acid, dicarboxylic acid, tricarboxylic acid, and combinations thereof. In certain embodiments, the salt of the immune response modifier can be a salt of an acid selected from the group consisting of hydrobromic acid, hydrochloric acid, lactic acid, glutamic acid, gluconic acid, tartaric acid, succinic acid, and combinations thereof.

The immune response modifier is substantially completely dissolved at a therapeutic level (i.e., therapeutically effective amount) in the formulation at room temperature. This amount is effective to treat and/or prevent a specified condition (e.g., allergic rhinitis, a viral infection, sinusitis, asthma). In general, the amount of the IRM compound present in an aqueous (preferably, sprayable) formulation of the invention will be an amount effective to provide a desired physiological effect, e.g., to treat a targeted condition (e.g., reduce symptoms of allergic rhinitis), to prevent recurrence of the condition, or to promote immunity against the condition. For certain embodiments, an amount effective to treat or inhibit a viral infection is an amount that will cause a reduction in one or more manifestations of viral infections, such as viral load, rate of virus production, or mortality as compared to untreated control animals.

The amount of an IRM compound that will be therapeutically effective in a specific situation will depend on such things as the activity of the particular compound, the dosing regimen, the application site, the particular formulation and the condition being treated. As such, it is generally not practical to identify specific administration amounts herein; however, those skilled in the art will be able to determine appropriate therapeutically effective amounts based on the guidance provided herein, information available in the art pertaining to these compounds, and routine testing.

In certain embodiments of the formulations of the invention, the amount or concentration of the IRM compound (or combinations of IRMs) is at least 0.0001% by weight (wt-%), in other embodiments, at least 0.001 wt-%, in other embodiments at least 0.01 wt-%, in other embodiments at least 0.1 wt-%, in other embodiments at least 0.5 wt-%, in other embodiments at least 1.0 wt-%, and in other embodiments at least 1.5 wt-%, based on the total formulation weight. In certain embodiments, the amount of the IRM compound (or combinations of IRMs) is at most 5.0 wt-%, and in other embodiments at most 3.0 wt-%, based on the total formulation weight.

Hydrophilic Viscosity Enhancing Agents

Formulations of the invention include a hydrophilic viscosity enhancing agent, preferably one that is a mucoadhesive. In this context, hydrophilic means the agent is water soluble or water dispersible.

Examples of suitable hydrophilic viscosity enhancing agents include: cellulose ethers such as hydroxypropyl methylcellulose, hydroxymethyl cellulose, hydroxypropyl cellulose, and carboxymethylcellulose sodium; polysaccharide gums such as xanthan gum and carrageenan; and acrylic acid polymers (i.e., homopolymers and copolymers) made from acrylic acid crosslinked with, for example, allyl sucrose or allyl pentaerythriol such as those polymers designated as carbomers in the United States Pharmacopoeia. Various combinations of these can be used if desired. Certain embodiments of the present invention include an acrylic acid polymer (i.e., polyacrylic acid polymer), carboxymethylcellulose sodium, xanthan gum, and combinations thereof.

Various grades of carboxymethylcellulose sodium are commercially available that have differing aqueous viscosities. Aqueous 1% weight by volume (w/v) solutions with viscosities of 5-13,000 cps may be obtained. Examples include carboxymethylcellulose sodium, high viscosity, USP (CA1494); carboxymethylcellulose sodium, medium viscosity, USP (CA192); and carboxymethylcellulose sodium, low viscosity, USP (CA193); all of which are available from Spectrum Chemicals and Laboratory Products, Inc., Gardena, Calif., USA; and AKUCELL AF 3085 (high viscosity), AKUCELL AF 2785 (medium viscosity), and AKUCELL AF 0305 (low viscosity), all of which are available from Akzo Nobel Functional Chemicals, Amersfoort, The Netherlands. In some embodiments of the invention, grades of carboxymethylcellulose sodium having a low aqueous viscosity are preferred.

In some embodiments of the invention, the hydrophilic viscosity enhancing agent is negatively charged. These include carboxymethylcellulose sodium, xanthan gum, and the carbomers.

In some embodiments of the invention, the hydrophilic viscosity enhancing agent includes carboxylic acid and/or carboxylate groups. Examples of such agents include carboxymethylcellulose sodium, xanthan gum, and the acrylic acid polymers.

In some embodiments of the invention the hydrophilic viscosity enhancing agent is uncrosslinked. Examples of such agents include cellulose ethers and xanthan gum.

The hydrophilic viscosity enhancing agent is present in formulations of the invention in an amount sufficient to bring the viscosity to a level of less than 100 centipoise (cps), preferably less than about 50 cps, more preferably less than about 20 cps, and most preferably less than about 10 cps. The viscosity is determined at 20±0.1° C. using a double-gap concentric cylinder at a controlled strain rate of 10 s$^{-1}$ to 1000 s$^{-1}$.

In certain embodiments, the amount or concentration of the hydrophilic viscosity enhancing agent (or combinations of such agents) is at least 0.01 wt-%, in other embodiments at least 0.025 wt-%, in other embodiments at least 0.05 wt-%, and in other embodiments at least 0.1 wt-%, based on the total formulation weight. In certain embodiments, the amount of the viscosity enhancing agent (or combinations of such agents) is at most 2.0 wt-%, in other embodiments at most 1.0 wt-%, in other embodiments at most 0.5 wt-%, and in other embodiments at most 0.25 wt-%, based on the total formulation weight.

pH Adjusting Agents and Buffers

Formulations of the invention can additionally include a pharmaceutically acceptable pH adjusting agent to adjust the pH of the formulation to the desired range. Generally, the pH is at least 4. Typically, the pH is no greater than 8, usually no greater than 7, and in some cases no greater than 6. The pH adjusting agent may be any pharmaceutically acceptable acid or base. Examples of suitable pH adjusting agents include hydrochloric acid, sodium hydroxide, tromethamine, and potassium hydroxide. Combinations of such agents can be used if desired.

The formulations of the invention can additionally include a pharmaceutically acceptable buffer to maintain the pH of the formulations in the desired range (generally, 4 to 8, usually, 4 to 7, and often, 4 to 6). The buffer may be any pharmaceutically acceptable buffer that provides one or more of the desired pH ranges. Examples of suitable buffers include buffers containing lactic acid, tartaric acid, citric acid, and succinic acid. Combinations of buffers can be used if desired. The buffers can also function as tonicity adjusting agents.

Cosolvents

The formulations of the invention can additionally include a water-miscible cosolvent. The water-miscible cosolvent assists in dissolving the immune response modifier or a salt thereof. The cosolvent can be a single component or a combination. Examples of suitable cosolvents include propylene glycol, glycerin, polyethylene glycol 400, diethylene glycol monoethyl ether, and combinations thereof. Certain water-miscible cosolvents, such as glycerin or propylene glycol, also add beneficial humectant properties to the formulations.

In certain embodiments, the cosolvent (or combination of cosolvents) is present in an amount of at least 5 wt-%, in other embodiments at least 10 wt-%, and in other embodiments at least 15 wt-%, based on the total weight of the formulation. In certain embodiments, the cosolvent (or combination of cosolvents) is present in an amount of at most 25 wt-%, and in other embodiments at most 20 wt-%, based on the total weight of the formulation. In certain preferred formulations, the cosolvent is present in an amount of 5 wt-% to 15 wt-%.

In certain embodiments, if a cosolvent is used, then water is present in an amount of at least 75 wt-%, and in other embodiments at least 80 wt-%, based on the total weight of the formulation. In certain embodiments, if a cosolvent is used, then water is present in an amount of at least 90 wt-%, and in other embodiments at least 95 wt-%, based on the total weight of the formulation.

Preservatives

The formulations of the invention can additionally include a preservative. The preservative includes one or more compounds that inhibit microbial growth (e.g., fungal and bacterial growth) within the composition. Suitable preservatives include benzalkonium chloride, benzethonium chloride, methylparaben, propylparaben, phenyl ethyl alcohol, and combinations thereof. Preferably, the preservative is benzalkonium chloride. Certain water-miscible cosolvents, such as glycerin or propylene glycol, also have antimicrobial properties when present in amounts greater than 15 wt-%.

In certain embodiments, the preservative (or combination of preservatives) is present in an amount of at least 0.005 wt-%, in other embodiments at least 0.01 wt-%, and in other embodiments at least 0.02 wt-%, based on the total weight of the formulation. In certain embodiments, the preservative (or combination of preservatives) is present in an amount of at most 0.5 wt-%, and in other embodiments at most 0.2 wt-%, based on the total weight of the formulation.

Chelating Agents

The formulations of the invention can additionally include a chelating agent. Chelating agents are compounds that complex metal ions. Examples of suitable chelating agents include ethylenediaminetetracetic acid (EDTA) and derivatives thereof such as the disodium salt, and ethylenediaminetetracetic acid disodium salt dihydrate. Preferably, the chelating agent is ethylenediaminetetracetic acid disodium salt dihydrate (edetate disodium).

In certain embodiments, the chelating agent (or combination of chelating agents) is present in an amount of at least 0.005 wt-%, in other embodiments at least 0.01 wt-%, in other embodiments at least 0.02 wt-%, and in other embodiments at least 0.05 wt-%, based on the total weight of the formulation. In certain embodiments, the chelating agent (or combination of chelating agents) is present in an amount of at most 0.5 wt-%, and in other embodiments at most 0.2 wt-%, based on the total weight of the formulation.

Applications

Formulations of the invention can be applied to the respiratory tract (e.g., nasal passages) of a subject (particularly, e.g., a mammal). Depending on the particular IRM compound, IRM compound concentration, and formulation composition, the therapeutic effect of the IRM compound may extend only to the superficial layers of the respiratory tract (e.g., nasal passages) or to tissues below the surface. Thus, another aspect of the present invention is directed to a method for the treatment of a nasal-associated condition by applying (preferably by spraying) one of the foregoing formulations into the nasal passages.

As used herein, a "nasal-associated condition" is defined as a condition in which an extrinsic protein (i.e., allergen, viral, bacterial, fungal) contacts the nasal mucosa creating an allergic and/or flu-like immune response. Examples include allergic rhinitis, sinusitis, asthma, and influenza.

Allergic rhinitis is a nasal-associated condition in which a subject is sensitized to one or more antigens (i.e., allergens). When a sensitized subject is re-exposed to an antigen, mediators are released quickly leading to rhinorrhea, increased nasal mucosal secretions, increased vascular permeability and vasodilation in the subject's nasal mucosa. IRMs have the ability to desensitize a subject to one or more antigens. As can be seen in Table 7, the formulation of Example 61 which contains IRM 22, when dosed at 0.375 wt-%, was able to inhibit 95% of nasal perfusion of Evan's blue when the sensitized subjects were re-exposed to the antigen ovalbumin. Thus, when a subject is treated with an IRM prior to a re-exposure to an antigen, the IRM is capable of desensitizing subjects who have been sensitized to an antigen.

Accordingly, the present invention includes use of the formulations described herein for treating and/or preventing allergic rhinitis, treating and/or preventing a viral infection, treating and/or preventing sinusitis, and treating and/or preventing asthma. For treatment of asthma, the formulations would generally be delivered to the lung via inhalation, e.g., by a nebulizer or spray.

The present invention also provides a method of desensitizing a subject to an antigen, the method involves administering to the subject an IRM compound in a formulation of the present invention, after the subject has been sensitized to the antigen, in an amount effective to desensitize the subject to the antigen. Preferably, the IRM compound is administered to the subject at least four hours prior to re-exposure of the subject to the antigen.

The formulations of the present invention can also be used administered together (e.g., in one composition or separately but simultaneously) with a vaccine for enhanced vaccine effectivity.

In some embodiments, the methods of the present invention include administering sufficient formulation to provide a dose of IRM compound of, for example, from 100 ng/kg to 50 mg/kg to the subject, although in some embodiments the methods may be performed by administering IRM compound in concentrations outside this range. In some of these embodiments, the method includes administering sufficient formulation to provide a dose of IRM compound of from 10 µg/kg to 5 mg/kg to the subject, for example, a dose of from 100 µg/kg to 1 mg/kg.

In some embodiments, the above-described formulations are particularly advantageous for application for a period of time sufficient to obtain a desired therapeutic effect without undesired systemic absorption of the IRM.

EXAMPLES

Objects and advantages of this invention are further illustrated by the following examples, but the particular materials and amounts thereof recited in these examples, as well as other conditions and details, should not be construed to unduly limit this invention.

IRM Compounds

The IRM compounds that were used to prepare the aqueous formulations are shown in Table 1 below.

TABLE 1

| Compound | Chemical Name | Reference |
|---|---|---|
| IRM 1 | N-{2-[4-amino-2-(ethoxymethyl)-1H-imidazo[4,5-c]quinolin-1-yl]-1,1-dimethylethyl}methanesulfonamide | U.S. Pat. No. 6,677,349 Example 268 |
| IRM 2 | 4-amino-2-butyl-α,α-dimethyl-1H-imidazo[4,5-c][1,5]naphthyridine-1-ethanol | U.S. Pat. No. 6,194,425 Example 62 |
| IRM 3 | 2-(2-methoxyethyl)-1-(2-methylpropyl)-1H-imidazo[4,5-c]quinolin-4-amine | U.S. Pat. No. 5,389,640 Example 72 |
| IRM 4 | 4-amino-α,α,2-trimethyl-6,7,8,9-tetrahydro-1H-imidazo[4,5-c]quinoline-1-ethanol | U.S. Pat. No. 5,342,784 Example 87 |
| IRM 5 | 4-amino-2-ethyl-α,α-dimethyl-1H-imidazo[4,5-c]quinoline-1-ethanol | U.S. Pat. No. 5,266,575 Example 6 |
| IRM 6 | 2-hydroxymethyl-1-(2-methylpropyl)-6,7,8,9-tetrahydro-1H-imidazo[4,5-c]quinolin-4-amine | U.S. Pat. No. 5,352,784 Example 94 |
| IRM 7 | 4-amino-α,α,2-trimethyl-1H-imidazo[4,5-c]quinoline-1-ethanol | U.S. Pat. No. 5,266,575 Example C1 |
| IRM 8 | 2-ethoxymethyl-1-[2-(3-phenylpropxy)ethyl]-1H-imidazo[4,5-c]quinolin-4-amine hydrochloride | U.S. Pat. No. 6,670,372 Example 16 |
| IRM 9 | N-[4-(4-amino-2-butyl-6,7-dimethyl-1H-imidazo[4,5-c]pyridin-1-yl)butyl]methanesulfonamide | U.S. Pat. No. 6,525,064 Example 2 |
| IRM 10 | N-{4-[4-amino-2-(2-methoxyethyl)-1H-imidazo[4,5-c]quinolin-1-yl]butyl}-1-isoquinolinecarboxamide | U.S. Pat. No. 6,451,810 Example 57 |
| IRM 11 | N-[3-(4-amino-2-butyl-1H-imidazo[4,5-c]quinolin-1-yl)propyl]morpholine-4-carboxamide | U.S. Pat. No. 6,573,273 Example 151 |
| IRM 12 | 4-amino-2-(ethoxymethyl)-α,α-dimethyl-6,7,8,9-tetrahydro-1H-imidazo[4,5-c]quinoline-1-ethanol | U.S. Pat. No. 5,352,784 Example 91 |
| IRM 13 | N-[3-(4-amino-2-butyl-1H-imidazo[4,5-c]quinolin-1-yl)propyl]-N'-butylurea | U.S. Pat. No. 6,573,273 Example 150 |
| IRM 14 | N-[2-(4-amino-2-butyl-1H-imidazo[4,5-c]quinolin-1-yl)ethyl]methanesulfonamide | U.S. Pat. No. 6,677,349 Example 265 |

TABLE 1-continued

| Compound | Chemical Name | Reference |
|---|---|---|
| IRM 15 | 2-butyl-1-[4-(1,1-dioxidoisothiazolidin-2-yl)butyl]-1H-imidazo[4,5-c]quinolin-4-amine | U.S. Pat. No. 6,677,349 Example 267 |
| IRM 16 | 2-methyl-1-[5-(methylsulfonyl)pentyl]-1H-imidazo[4,5-c]quinolin-4-amine | U.S. Pat. No. 6,664,264 Example 12 |
| IRM 17 | N-[2-(4-amino-2-butyl-6,7-dimethyl-1H-imidazo[4,5-c]pyridin-1-yl)-1,1-dimethylethyl]methanesulfonamide | U.S. Pat. No. 6,525,064# |
| IRM 18 | 2-butyl-1-{2-[2-(methylsulfonyl)ethoxy]ethyl}-1H-imidazo[4,5-c]quinolin-4-amine | U.S. Ser. No. 60/526,772 Example 2 |
| IRM 19 | 1-[2-(4-amino-2-ethoxymethyl-7-hydroxy-1H-imidazo[4,5-c]quinolin-1-yl)-1,1-dimethylethyl]-3-isopropylurea | U.S. Ser. No. 60/581,254 Example 145 |
| IRM 20 | 1-(2-amino-2-methylpropyl)-2-(ethoxymethyl)-1H-imidazo[4,5-c]quinolin-4-amine | U.S. Pat. No. 6,677,349 Example 268 Part G |
| IRM 21 | N-{2-[4-amino-2-(2-methoxyethyl)-6,7,8,9-tetrahydro-1H-imidazo[4,5-c]quinolin-1-yl]-1,1-dimethylethyl}methanesulfonamide | U.S. Pat. No. 6,331,539# |
| IRM 22 | N-[2-(4-amino-2-butyl-1H-imidazo[4,5-c]quinolin-1-yl)-1,1-dimethylethyl]methanesulfonamide | U.S. Pat. No. 6,677,349# |
| IRM 23 | N-{4-[4-amino-2-(cyclopropylmethyl)-1H-imidazo[4,5-c]quinolin-1-yl]butyl}methanesulfonamide | U.S. Pat. No. 6,677,349 Example 270 |
| IRM 24 | N-(2-{4-amino-2-ethoxymethyl-7-[6-(methanesulfonylamino)hexyloxy]-1H-imidazo[4,5-c]quinolin-1-yl}-1,1-dimethylethyl)methanesulfonamide | U.S. Ser. No. 60/508,634 Example 45 |
| IRM 25 | N-(6-{[4-amino-2-ethoxymethyl-1-(2-methanesulfonylamino-2-methylpropyl)-1H-imidazo[4,5-c]quinolin-7-yl]oxy}hexyl)acetamide | U.S. Ser. No. 60/508,634 Example 46 |
| IRM 26 | 1-{4-amino-2-(ethoxymethyl)-7-[5-(hydroxymethyl)pyridin-3-yl]-1H-imidazo[4,5-c]quinolin-1-yl}-2-methylpropan-2-ol | WO 04/058,759 Example 133 |
| IRM 27 | 1-(2-methylpropyl)-1H-imidazo[4,5-c][1,5]naphthyridin-4-amine | U.S. Pat. No. 6,194,425 Example 32 |
| IRM 28 | N-{4-[4-amino-2-(3-phenoxypropyl)-1H-imidazo[4,5-c]quinolin-1-yl]butyl}methanesulfonamide | U.S. Pat. No. 6,677,349 Example 262 |
| IRM 29 | 2-butyl-1-[2-(propylsulfonyl)ethyl]-1H-imidazo[4,5-c]quinolin-4-amine | U.S. Pat. No. 6,667,312 Example 62 |
| IRM 30 | N-{3-[4-amino-2-(2-methoxyethyl)-1H-imidazo[4,5-c]quinolin-1-yl]propyl}-N'-phenyl urea | U.S. Pat. No. 6,573,273 Example 161 |
| IRM 31 | 4-amino-2-ethoxymethyl-α,α,6,7-tetramethyl-1H-imidazo[4,5-c]pyridine-1-ethanol | U.S. Pat. No. 5,494,916 Example 47 |
| IRM 32 | N-{2-[4-amino-2-(ethoxymethyl)-1H-imidazo[4,5-c]quinolin-1-yl]-1,1-dimethylethyl}-N'-cyclohexylurea | U.S. Pat. No. 6,573,273# |
| IRM 33 | N-{2-[4-amino-2-(ethoxymethyl)-1H-imidazo[4,5-c]quinolin-1-yl]-1,1-dimethylethyl}cyclohexanecarboxamide | U.S. Pat. No. 6,756,382# |
| IRM 34 | N-{2-[4-amino-2-(ethoxymethyl)-1H-imidazo[4,5-c]quinolin-1-yl]-1,1-dimethylethyl}-2-ethoxyacetamide | U.S. Pat. No. 6,756,382 Example 209 |
| IRM 35 | N-{2-[4-amino-2-(ethoxymethyl)-6,7,8,9-tetrahydro-1H-imidazo[4,5-c]quinolin-1-yl]-1,1-dimethylethyl}methanesulfonamide | U.S. Pat. No. 6,677,349# |
| IRM 36 | N-[4-(4-amino-2-propyl-1H-imidazo[4,5-c]quinolin-1-yl)butyl]methanesulfonamide | U.S. Pat. No. 6,677,349 Example 235 |
| IRM 37 | N-{2-[4-amino-2-(ethoxymethyl)-6,7-dimethyl-1H-imidazo[4,5-c]pyridin-1-yl]-1,1-dimethylethyl}-N'-phenylurea | U.S. Pat. No. 6,545,017# |
| IRM 38 | N-[4-(4-amino-2-ethyl-1H-imidazo[4,5-c]quinolin-1-yl)butyl]methanesulfonamide | U.S. Pat. No. 6,677,349 Example 236 |
| IRM 39 | N-{8-[4-amino-2-(methoxyethyl)-1H-imidazo[4,5-c]quinolin-1-yl]octyl}methanesulfonamide | U.S. Pat. No. 6,677,349 Example 243 |
| IRM 40 | N-{2-[4-amino-2-(ethoxymethyl)-6,7-dimethyl-1H-imidazo[4,5-c]pyridin-1-yl]ethyl}benzamide | U.S. Pat. No. 6,545,016# |
| IRM 41 | 6-(4-amino-2-propyl-1H-imidazo[4,5-c]quinolin-1-yl)-1-morpholin-4-ylhexan-1-one | U.S. Ser. No. 60/555,753 Example 6 |
| IRM 42 | 1-{3-[4-amino-7-(3-hydroxymethylphenyl)-2-(2-methoxyethyl)-1H-imidazo[4,5-c]quinolin-1-yl]propyl}pyrrolidin-2-one | WO 04/058,759 Example 185 |
| IRM 43 | 1-{4-[4-amino-2-ethoxymethyl-7-(pyridin-3-yl)-1H-imidazo[4,5-c]quinolin-1-yl]buytl}3-cyclopentylurea | WO 04/058,759 Example 377 |
| IRM 44 | 1-{4-[4-amino-2-ethoxymethyl-7-(pyridin-3-yl)-1H-imidazo[4,5-c]quinolin-1-yl]buytl}3-isopropylurea | WO 04/058,759 Example 379 |
| IRM 45 | N-[4-(4-amino-2-methyl-6,7,8,9,-tetrahydro-1H-imidazo[4,5-c]quinolin-1-yl)butyl]morpholine-4-carboxamide | U.S. Pat. No. 6,573,273 Example 170 |
| IRM 46 | 4-(4-amino-2-propyl-1H-imidazo[4,5-c]quinolin-1-yl)-N-methoxy-N-methylbutyramide | U.S. Ser. No. 60/524,961 Example 20 |

This compound is not specifically exemplified but can be readily prepared using the synthetic methods disclosed in the cited reference.

Excipients

The excipients that were used to prepare the aqueous sprayable formulations are shown in Table 2 below.

TABLE 2

Carboxymethylcellulose sodium, low viscosity, USP (CMC)
Hydroxypropyl methylcellulose (hypromellose, 2910, 50 cps, USP; HPMC)
Acetic acid, NF
Citric acid, USP
L-Lactic acid
Succinic acid
L-Tartaric acid
Polyethylene glycol 400, NF (PEG 400),
Propylene glycol, USP
Glycerin, USP
Diethylene glycol monoethyl ether, NF
Benzalkonium chloride, Ph. Eur.
Ethylenediaminetetraacetic acid disodium salt dihydrate (Edetate disodium, USP)
1 N Sodium hydroxide, NF (1 N NaOH)
10 N Sodium hydroxide, NF (10 N NaOH)
1N Hydrochloric acid, NF (1 N HCl)
Water, USP USP United States Pharmacopeia
NF National Formulary (USA)
Ph. Eur. European Pharmacopeia Preparation of the Formulations The aqueous formulations were prepared using the following general method. The hydrophilic viscosity enhancing agent was hydrated in water (about 50% of total) for about 20 minutes with stirring. The edetate sodium was added and mixed until dissolved. The resulting solution was mixed with the benzalkonium chloride. Separately, the buffering agent (if used) and the cosolvent (if used) were mixed with water; the IRM compound was added to this combination and stirred. The two combinations were combined and mixed. A pH adjuster was added, as necessary, to adjust each formulation to the desired pH. Finally, water was added to each formulation to adjust to the final formulation weight.

Test Method

Inhibition of Ovalbumin-Induced Changes in Plasma Extravasation in a Model of Allergic Rhinitis in Brown-Norway Rats Formulations of the invention were tested for their ability to inhibit ovalbumin-induced changes in plasma extravasation using the following test method.

Male Brown-Norway rats (150-250 g) are used to monitor pulmonary and nasal responses to aerosolized antigen challenge in conscious animals and establish late pulmonary responses which can be measured by various functional or cellular measures. Groups of rats (4 to 5 per group) are sensitized to ovalbumin (grade V or VI), 4 mg/Kg, with $Al(OH)_3$, 400 mg/Kg in 0.9% saline by intraperitoneal administration on 3 consecutive days. At $\geq 21$ days a drug solution or vehicle (control groups) is administered by nasal instillation. Nasal instillation is performed by lightly anesthetizing an animal with a combination of a solution consisting of 10 mL of ketamine HCl (100 mg/mL) and acepromazine (10 mg/mL) dosed at a rate of 60-90 mg/Kg. A solution of drug or vehicle is instilled in a drop-by-drop manner (each drop is cleared from the nasal passage before the next drop is administered) to each nare (10 μL/nare) for a total of 20 μL/animal. Ophthalmic ointment will be used in conjunction with the ketamine/xylazine combination. The animal is placed back into the cage and becomes fully alert within 1-2 hours. Twenty (20) hours later the animal is dosed a second time using the same procedure.

Four (4) hours after the second dosing, animals are placed inside an inverted desiccator jar, which is placed onto a Plexiglas platform forming a chamber with a diameter of 6 inches (15 cm) and a height of 6 inches (15 cm). The platform has several ports which allow for aerosolization, for monitoring breathing patterns, for exhausting aerosolized particles and for providing a constant flow of air into the chamber from a continuous air source to prevent hypoxia. Aerosolization of $H_2O$, ovalbumin ($\leq 100$ mg/mL) is done using a DeVilbiss Ultra-Neb large volume ultrasonic nebulizer system for 10-30 minutes in duration. Following ovalbumin aerosol challenge, the animals are returned to their cages.

Twenty-four (24) hours after the ovalbumin challenge, the animals are initially anesthetized using a combination of 10 mL of ketamine HCl (100 mg/mL) and 2 mL of acepromazine maleate (10 mg/mL) dosed intraperitoneally at 60-90 mg/Kg (dose to effect). Once the animal is exhibiting no response to external stimuli (toe pinch, eye reflex, etc.) about 1 mL of lidocaine is injected subcutaneously over the trachea and surrounding neck area. An incision is made midline over the trachea and the internal or external jugular vein is exposed and cannulated (INTRAMEDIC polyethylene tubing size PE50 is used with a 23 g luer stub adapter). The trachea is exposed and a modified tracheotomy is performed (a longitudinal incision about 5 mm long). A 6f-tracheal catheter is inserted caudally and a catheter (PE40-60) inserted cranally. Both tubes are tied in place and the animal is hooked up to a HARVARD small animal respirator (a 58 breaths/min, 4 cc stroke volume). At this point the animal is given 0.1-0.25 mL of a solution consisting of 0.3 mL sodium pentobarbital and 0.7 mL saline (dose to effect). Animals in the drug treatment groups and in the ovalbumin control group receive an additional challenge with ovalbumin. A nasal perfusion line is attached to a HARVARD compact infusion pump set to deliver 0.2 mL/min and a 10% solution of ovalbumin in saline is manually "pushed" through the nasal infusion catheter slowly until 1 or 2 drops of the ovalbumin solution is expressed through the nose. Once the air is flushed out of the line with ovalbumin solution the line is attached to the infusion pump, the pump is turned on and allowed to run for 3 min at a rate of 0.2 mL/min. Animals in the saline control group are treated with saline alone. After the 3 minute exposure period the ovalbumin solution is flushed out of the line and nasal cavities with air. The nasal infusion catheter is then filled with pH adjusted PBS (about pH 5) and PBS is manually "pushed" through the nasal perfusion catheter slowly until 1 or 2 drops of PBS is expressed through the nose. Once the air is flushed out of the line with PBS, the line is attached to the infusion pump and the pump is allowed to run for 3 min. Evans Blue dye (1 mL of 1.0%) is injected intravenously; the infusion pump is turned on and a timer is started for a 40 min collection period. The nasal perfusate is collected in a 15 mL-collection tube. One sample is collected (8 mLs for 40 min). The amount of Evans blue dye in the sample is determined spectrophotometrically (610 nm wavelength).

The percent inhibition is calculated using the equation below:

$$\% \text{ Inhibition} = \left\{ 1 - \left( \frac{(\mu g \text{ Evans Blue})_{Drug} - (\mu g \text{ Evans Blue})_{Saline\ Control}}{(\mu g \text{ Evans Blue})_{OVA\ Control} - (\mu g \text{ Evans Blue})_{Saline\ Control}} \right) \right\} \times 100$$

Where the OVA control is the group of animals that is dosed with vehicle and receives an additional challenge with ovalbumin and the saline control is the group of animals that is dosed with vehicle and receives an additional challenge with saline.

Examples 1-17

A series of aqueous formulations containing IRM 1 were prepared and tested in a model of allergic rhinitis using the test method described above. Tables 3 and 4 show the composition of each formulation and the test result.

TABLE 3

| Ingredients | Formulations (percentage weight by weight) | | | | | | | | |
|---|---|---|---|---|---|---|---|---|---|
| | Ex 1 | Ex 2 | Ex 3 | Ex 4 | Ex 5 | Ex 6 | Ex 7 | Ex 8 | Ex 9 |
| IRM 1 | 0.0375 | 0.125 | 0.375 | 0.125 | 0.0375 | 0.125 | 0.375 | 0.125 | 0.125 |
| CMC | 0.1 | 0.1 | 0.1 | 0.1 | 0.1 | 0.1 | 0.1 | 0.1 | 0.1 |
| L-Tartaric acid | — | — | — | 1.65 | — | — | — | — | — |
| L-Lactic Acid | 1.53 | 1.53 | 1.53 | — | 1.53 | 1.53 | 1.53 | — | — |
| Succinic Acid | — | — | — | — | — | — | — | — | 1.2 |
| PEG 400 | 15 | 15 | 15 | 15 | — | — | — | — | — |
| Diethylene glycol monoethyl ether | — | — | — | — | 15 | 15 | 15 | 15 | — |
| Benzalkonium chloride | 0.02 | 0.02 | 0.02 | 0.02 | 0.02 | 0.02 | 0.02 | 0.02 | 0.02 |
| Edetate disodium | 0.1 | 0.1 | 0.1 | 0.1 | 0.1 | 0.1 | 0.1 | 0.1 | 0.1 |
| 1 N NaOH | qs | qs | qs | qs | qs | qs | qs | — | qs |
| 1 N HCl | — | — | — | — | — | — | — | — | — |
| Water | qs | qs | qs | qs | qs | qs | qs | qs | qs |
| PH | 3.9 | 4.0 | 3.8 | 5.1 | 4.0 | 4.2 | 3.9 | 7.4 | 5.0 |
| % Inhibition | 0 | 33 | 69 | 38 | 0 | 49 | 42 | 29 | 21 |

TABLE 4

| Ingredients | Formulations (percentage weight by weight) | | | | | | | |
|---|---|---|---|---|---|---|---|---|
| | Ex 10 | Ex 11 | Ex 12 | Ex 13 | Ex 14 | Ex 15 | Ex 16 | Ex 17 |
| IRM 1 | 0.125 | 0.125 | 0.125 | 0.00375 | 0.0125 | 0.0375 | 0.125 | 0.375 |
| CMC | 0.1 | 0.2 | 0.05 | 0.1 | 0.1 | 0.1 | 0.1 | 0.1 |
| L-Tartaric acid | — | 1.65 | 1.65 | 1.65 | 1.65 | 1.65 | 1.65 | 1.65 |
| L-Lactic Acid | 1.53 | — | — | — | — | — | — | — |
| Succinic Acid | — | — | — | — | — | — | — | — |
| PEG 400 | — | — | — | — | — | — | — | — |
| Diethylene glycol monoethyl ether | — | — | — | — | — | — | — | — |
| Benzalkonium chloride | 0.02 | 0.02 | 0.02 | 0.02 | 0.02 | 0.02 | 0.02 | 0.02 |
| Edetate disodium | 0.1 | 0.1 | 0.1 | 0.1 | 0.1 | 0.1 | 0.1 | 0.1 |
| 1 N NaOH | — | qs | qs | qs | qs | qs | qs | qs |
| 1 N HCl | qs | — | — | — | — | — | — | — |
| Water | qs | qs | qs | qs | qs | qs | qs | qs |
| pH | 4.1 | 4.9 | 5.0 | 5.0 | 5.0 | 5.0 | 5.0 | 5.0 |
| % Inhibition | 68 | 27 | 14 | 33 | 39 | 43 | 61 | 69 |

Examples 18-23

A series of aqueous formulations containing IRM 2 were prepared and tested in a model of allergic rhinitis using the test method described above. Table 5 shows the composition of each formulation and the test result.

TABLE 5

| | Formulations (percentage weight by weight) | | | | | |
|---|---|---|---|---|---|---|
| Ingredients | Ex 18 | Ex 19 | Ex 20 | Ex 21 | Ex 22 | Ex 23 |
| IRM 2 | 0.0375 | 0.00375 | 0.0125 | 0.0375 | 0.0375 | 0.0375 |
| CMC | 0.1 | 0.1 | 0.1 | 0.1 | 0.1 | 0.1 |
| L-Tartaric acid | 1.65 | 1.65 | 1.65 | 1.65 | — | — |
| L-Lactic Acid | — | — | — | — | 1.53 | 1.53 |
| PEG 400 | 10 | 10 | 10 | 10 | — | 15 |
| Diethylene glycol monoethyl ether | — | — | — | — | 10 | — |
| Benzalkonium chloride | 0.02 | 0.02 | 0.02 | 0.02 | 0.02 | 0.02 |
| Edetate disodium | 0.1 | 0.1 | 0.1 | 0.1 | 0.1 | 0.1 |
| 1 N NaOH | qs | — | — | — | — | — |
| 10 N NaOH | — | qs | qs | qs | qs | qs |
| Water | qs | qs | qs | qs | qs | qs |
| pH | 5.2 | 4.1 | 4.1 | 4.1 | 4.1 | 3.9 |
| % Inhibition | 50 | 3 | 48 | 73 | 61 | 80 |

Examples 24-131

A series of aqueous formulations containing IRMs were prepared and tested in a model of allergic rhinitis using the test method described above. Each IRM was formulated using one or more of the vehicles shown in Table 6. Table 7 shows the composition of each formulation and the test result.

TABLE 6

| | Vehicle (percentage weight by weight) | | | | | | | | | | |
|---|---|---|---|---|---|---|---|---|---|---|---|
| Ingredients | A | B | C | D | E | F | G | H | I | J | K |
| CMC | 0.1 | 0.1 | 0.1 | 0.1 | 0.1 | 0.1 | 0.1 | 0.1 | — | 0.1 | 0.1 |
| HPMC | — | — | — | — | — | — | — | — | 0.1 | — | — |
| L-Tartaric acid | 1.65 | — | — | 1.65 | — | — | — | — | 1.65 | 1.65 | — |
| L-Lactic Acid | — | 1.53 | 1.53 | — | — | — | — | — | — | — | 1.53 |
| Citric acid | — | — | — | — | 1.53 | 1.53 | — | — | — | — | — |
| Acetic acid | — | — | — | — | — | — | 1.1 | 1.1 | — | — | — |
| PEG 400 | — | — | 15 | 10 | 15 | — | — | 10 | 15 | — | — |
| Diethylene glycol monoethyl ether | — | 15 | — | — | — | — | — | — | — | — | 15 |
| Glycerin | — | — | — | — | — | 15 | — | — | — | — | — |
| 1:1 propylene glycol:PEG 400 | — | — | — | — | — | — | 15 | — | — | — | — |
| Benzalkonium chloride | 0.02 | 0.02 | 0.02 | 0.02 | 0.02 | 0.02 | 0.02 | 0.02 | 0.02 | 0.02 | 0.02 |
| Edetate disodium | 0.1 | 0.1 | 0.1 | 0.1 | 0.1 | 0.1 | 0.1 | 0.1 | 0.1 | 0.1 | 0.1 |
| 1 N NaOH | qs | qs | qs | qs | qs | qs | qs | qs | qs | qs | qs |
| Water | qs | qs | qs | qs | qs | qs | qs | qs | qs | qs | qs |
| pH | 5.0-5.1 | 3.8-4.1 | 3.8-4.0 | 5.1-5.2 | 4.0 | 4.0 | 5.0 | 5.2 | 6.0 | 4.0 | 5.0 |

TABLE 7

| Example | IRM | Wt % IRM | Vehicle | % Inhibition |
|---|---|---|---|---|
| 24 | 3 | 0.125 | A | 25 |
| 25 | 4 | 0.0375 | A | 19 |
| 26 | 5 | 0.0375 | A | 12 |
| 27 | 6 | 0.0375 | A | 0 |
| 28 | 7 | 0.0125 | A | 7 |
| 29 | 7 | 0.0375 | A | 0 |
| 30 | 7 | 0.125 | G | 40 |
| 31 | 8 | 0.0375 | H | 0 |
| 32 | 9 | 0.0375 | D | 19 |
| 33 | 10 | 0.0375 | D | 14 |
| 34 | 10 | 0.0375 | B | 0 |
| 35 | 10 | 0.125 | B | 12 |
| 36 | 11 | 0.0375 | B | 36 |
| 37 | 11 | 0.0125 | B | 37 |
| 38 | 11 | 0.125 | B | 54 |
| 39 | 11 | 0.125 | C | 0 |
| 40 | 12 | 0.0375 | B | 34 |
| 41 | 13 | 0.0375 | B | 0 |

TABLE 7-continued

| Example | IRM | Wt % IRM | Vehicle | % Inhibition |
|---|---|---|---|---|
| 42 | 14 | 0.0375 | B | 15 |
| 43 | 14 | 0.0375 | C | 25 |
| 44 | 15 | 0.0375 | C | 0 |
| 45 | 16 | 0.125 | K | 50 |
| 46 | 16 | 0.00375 | J | 0 |
| 47 | 16 | 0.0375 | J | 0 |
| 48 | 16 | 0.375 | J | 0 |
| 49 | 16 | 0.00375 | C | 0 |
| 50 | 16 | 0.0375 | C | 0 |
| 51 | 16 | 0.125 | C | 0 |
| 52 | 17 | 0.375 | E | 78 |
| 53 | 18 | 0.375 | E | 0 |
| 54 | 19 | 0.375 | E | 0 |
| 55 | 20 | 0.0375 | C | 57 |
| 56 | 21 | 0.00375 | A | 0 |
| 57 | 21 | 0.0375 | A | 42 |
| 58 | 21 | 0.375 | A | 40 |
| 59 | 22 | 0.00375 | A | 0 |
| 60 | 22 | 0.0375 | A | 49 |
| 61 | 22 | 0.375 | A | 95 |
| 62 | 23 | 0.00375 | A | 0 |
| 63 | 23 | 0.0375 | A | 1 |
| 64 | 23 | 0.375 | A | 0 |
| 65 | 24 | 0.00375 | A | 7 |
| 66 | 24 | 0.0375 | A | 13 |
| 67 | 24 | 0.125 | A | 0 |
| 68 | 25 | 0.00375 | A | 22 |
| 69 | 25 | 0.0375 | A | 63 |
| 70 | 25 | 0.375 | A | 38 |
| 71 | 26 | 0.00375 | A | 29 |
| 72 | 26 | 0.0375 | A | 43 |
| 73 | 26 | 0.125 | A | 37 |
| 74 | 27 | 0.0125 | C | 24 |
| 75 | 28 | 0.0375 | C | 62 |
| 76 | 28 | 0.0375 | B | 0 |
| 77 | 28 | 0.125 | B | 0 |
| 78 | 28 | 0.375 | B | 29 |
| 79 | 29 | 0.0375 | C | 15 |
| 80 | 29 | 0.0125 | B | 5 |
| 81 | 29 | 0.0375 | B | 32 |
| 82 | 29 | 0.125 | B | 0 |
| 83 | 30 | 0.0375 | C | 0 |
| 84 | 31 | 0.0375 | C | 0 |
| 85 | 32 | 0.0375 | B | 60 |
| 86 | 33 | 0.0375 | B | 0 |
| 87 | 34 | 0.0375 | B | 36 |
| 88 | 35 | 0.0375 | B | 32 |
| 89 | 35 | 0.125 | B | 58 |
| 90 | 35 | 0.00375 | A | 0 |
| 91 | 35 | 0.0375 | A | 26 |
| 92 | 35 | 0.375 | A | 0 |
| 93 | 36 | 0.00375 | A | 0 |
| 94 | 36 | 0.0375 | A | 35 |
| 95 | 36 | 0.125 | A | 56 |
| 96 | 36 | 0.125 | C | 35 |
| 97 | 36 | 0.00375 | I | 0 |
| 98 | 36 | 0.0375 | I | 0 |
| 99 | 36 | 0.375 | I | 14 |
| 100 | 37 | 0.125 | B | 54 |
| 101 | 38 | 0.125 | C | 0 |
| 102 | 38 | 0.00375 | A | 0 |
| 103 | 38 | 0.0375 | A | 0 |
| 104 | 38 | 0.125 | A | 0 |
| 105 | 39 | 0.00375 | A | 0 |
| 106 | 39 | 0.0375 | A | 0 |
| 107 | 39 | 0.125 | A | 0 |
| 108 | 40 | 0.00375 | C | 0 |
| 109 | 40 | 0.0375 | C | 32 |
| 110 | 40 | 0.125 | C | 0 |
| 111 | 41 | 0.00375 | A | 0 |
| 112 | 41 | 0.0375 | A | 37 |
| 113 | 41 | 0.125 | A | 18 |
| 114 | 42 | 0.00375 | A | 9 |
| 115 | 42 | 0.0375 | A | 27 |
| 116 | 42 | 0.125 | A | 23 |
| 117 | 42 | 0.00375 | C | 11 |
| 118 | 42 | 0.0375 | C | 44 |
| 119 | 42 | 0.125 | C | 0 |
| 120 | 43 | 0.00375 | F | 0 |
| 121 | 43 | 0.0375 | F | 0 |
| 122 | 43 | 0.125 | F | 5 |
| 123 | 44 | 0.00375 | F | 12 |
| 124 | 44 | 0.0375 | F | 33 |
| 125 | 44 | 0.125 | F | 0 |
| 126 | 45 | 0.00375 | A | 0 |
| 127 | 45 | 0.0375 | A | 0 |
| 128 | 45 | 0.125 | A | 12 |
| 129 | 46 | 0.00375 | A | 27 |
| 130 | 46 | 0.0375 | A | 43 |
| 131 | 46 | 0.125 | A | 24 |

Example 132

IRM 1 was prepared as a 0.375% solution formulation capable of being nasally administered via a spray pump. The formulation vehicle was prepared as follows:

TABLE 9

| Excipient | w/w % |
|---|---|
| Carboxymethylcellulose sodium, low viscosity, USP (Spectrum Chemicals and Laboratory Products, Inc., Gardena, CA,) | 0.1 |
| Benzalkonium chloride, Ph. Eur. (Fluka, Buchs Switzerland) | 0.02 |
| Disodium EDTA, USP (Spectrum Chemicals) | 0.1 |
| L-Lactic acid, Purac (Lincolnshire, IL) | 1.53 |
| PEG 400, NF (Spectrum Chemicals) | 15 |
| 1 N NaOH, NF (Spectrum Chemicals) | qs |
| Water | qs |
| Total | 100.00 |
| pH | 4.0 |

Carboxymethylcellulose sodium, low viscosity, USP (CMC) was hydrated in water (about 50% of total) for 20 minutes with stirring. The EDTA was added and dissolved. The CMC/EDTA solution was mixed with the benzalkonium chloride to form a CMC/EDTA/BAC solution. Separately, the lactic acid and PEG 400 were mixed with water. For the IRM 1 formulation, IRM 1 was dissolved into the lactic acid/PEG 400 solution. The CMC/EDTA/BAC solution was mixed with lactic acid/PEG 400 solution to prepare the Vehicle formulation. The CMC/EDTA/BAC solution was mixed with lactic acid/PEG 400/IRM 1 solution to prepare the IRM 1 formulation. 1 N NaOH was added, as necessary, to adjust each formulation to a pH of 4.0. Finally, water was added to each formulation to adjust to the final formulation weight.

Fisher 344 rats (Charles River Laboratories, Raleigh, N.C.) were divided into six treatment groups. Rats in each group were infected intranasally with humanized, non-lethal influenza virus. 24 hours after infection, viral titers were measured in nasal lavage fluid and whole lung homogenates. The influenza virus and methods for measuring viral titers are described in Burleson, Gary L., "Influenza Virus Host Resistance Model for Assessment of Immunotoxicity, Immunostimulation, and Antiviral Compounds," *Methods in Immunology* 2:181-202, Wiley-Liss Inc., 1995.

Figure 2:
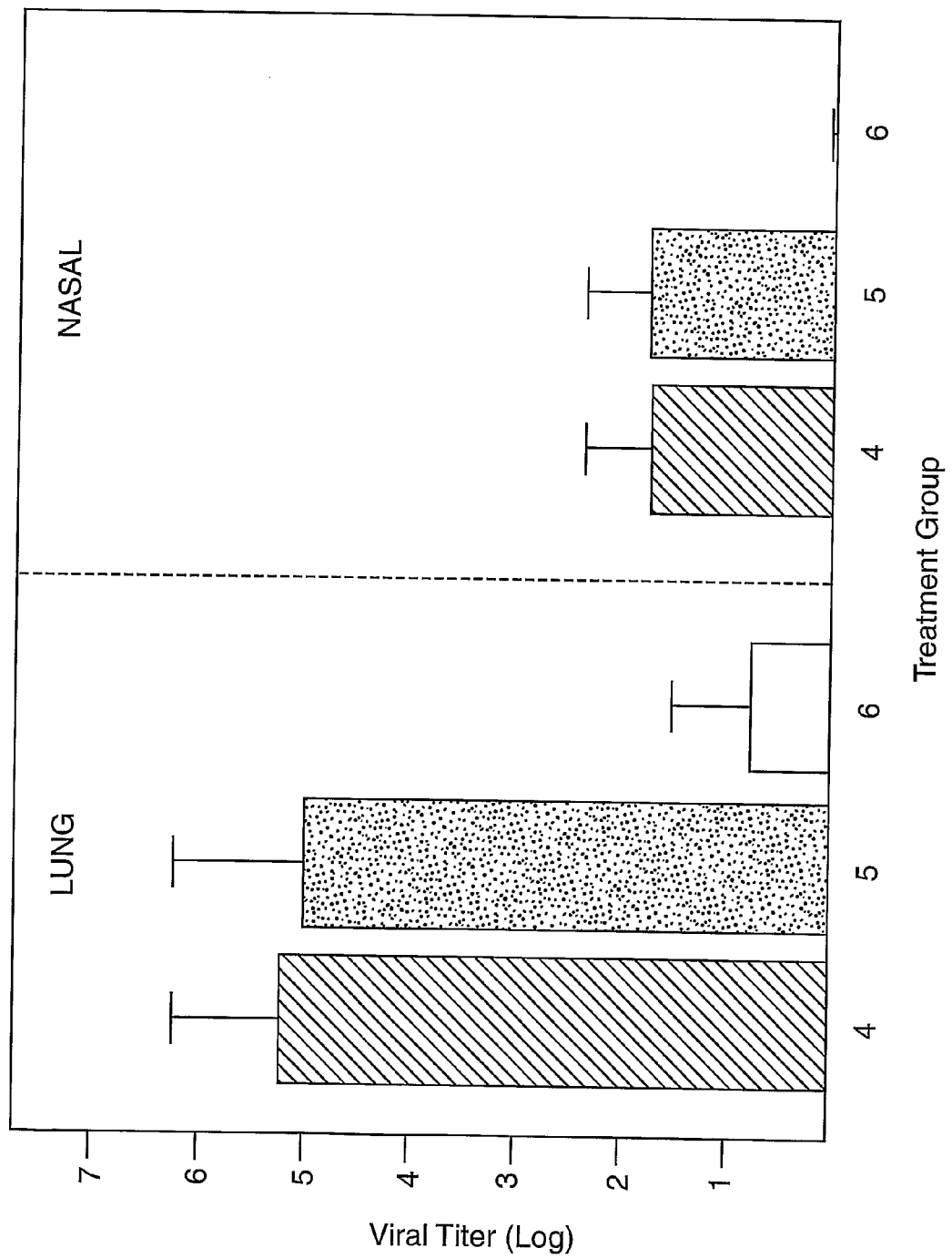
FIG. 2 is a bar graph comparing viral titers in rats after treatment with vehicle, IFN-α, or IRM compound twenty-four hours and again at four hours before viral challenge.

Each of the six treatment groups received a different pre-infection treatment. Rats in each group received the treatment indicated in Table 10. The results are summarized in FIG. 1 and FIG. 2.

TABLE 10

| Group | Treatment |
|---|---|
| 1 | Vehicle formulation (Table 9), 50 μL (25 μL per nare), 1x* |
| 2 | Interferon-α (rat recombinant IFN-α, Cat. No. PRP13, Serotec Inc., Raleigh, NC), 10,000 IU, 1x |
| 3 | IRM 1 formulation (Table 9), 50 μL (25 μL per nare), 1x |
| 4 | Vehicle formulation (Table 9), 50 μL (25 μL per nare), 2x** |
| 5 | Interferon-α, 10,000 IU, 2x (Day −1: Product No. RR2030U, Pierce Biotechnology, Inc., Rockford, IL; Day 0: Serotec Inc. Cat. No. PRP13) |
| 6 | IRM 1 formulation (Table 9), 50 μL (25 μL per nare), 2x |

*1x: one dose of treatment provided four hours before viral infection.
**2x: one dose of treatment 24 hours (Day −1) before viral infection, second treatment four hours before viral infection (Day 0).

Example 133

A formulation containing 4-amino-α,α-dimethyl-2-ethoxymethyl-1H-imidazo[4,5-c]quinoline-1-ethanol (U.S. Pat. No. 5,389,640; Example 99) was prepared using the method described above. The composition is shown in Table 11 below.

TABLE 11

| Ingredient | w/w % |
|---|---|
| IRM | 0.0125 |
| CMC | 0.1 |
| Benzalkonium chloride | 0.02 |
| Edetate disodium | 0.1 |
| L-Tartaric acid | 1.65 |
| 10 N NaOH | qs |
| Water | qs |
| Total | 100.00 |
| pH | 5.0 |

The viscosity of the formulation was measured using a controlled stress step test. Rheometer: Haake RS150; sensor: double-gap concentric cylinder (DG41); gap: 5.100 mm; sample size: sufficient to fill the sample holder; temperature 20.0±0.1° C.; initial stress: 0.10 Pa; final stress: 1.20 Pa. Three (3) separate samples were measured. The measured viscosity was 1.4 cps for each of the samples.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. An aqueous sprayable formulation for delivery of an immune response modifier to the nasal passage of a subject comprising:
    an immune response modifier, wherein the immune response modifier is N-{2-[4-amino-2-(ethoxymethyl)-1H-imidazo[4,5-c]quinolin-1-yl]-1,1-dimethylethyl}methanesulfonamide, or a pharmaceutically acceptable salt thereof;
    water; and
    a hydrophilic viscosity enhancing agent;
    with the proviso that the hydrophilic viscosity enhancing agent is not covalently bonded to the immune response modifier;
    wherein the formulation is a solution at room temperature, has a viscosity of less than 100 cps at room temperature, and is contained in a nasal spray device.

2. The aqueous formulation of claim 1 wherein the hydrophilic viscosity enhancing agent is negatively charged.

3. The aqueous formulation of claim 1 wherein the hydrophilic viscosity enhancing agent is uncrosslinked.

4. The aqueous formulation of claim 1 wherein the hydrophilic viscosity enhancing agent is selected from the group consisting of cellulose ethers, polysaccharide gums, acrylic acid polymers, and combinations thereof.

5. The aqueous formulation of claim 1 wherein the hydrophilic viscosity enhancing agent comprises carboxylic acid groups and/or carboxylate groups.

6. The aqueous formulation of claim 5 wherein the hydrophilic viscosity enhancing agent is selected from the group consisting of an acrylic acid polymer, carboxymethyl cellulose sodium, xanthan gum, and combinations thereof.

7. The aqueous formulation of claim 1 wherein the immune response modifier is a salt of an acid selected from the group consisting of a carboxylic acid, a halo acid, sulfuric acid, phosphoric acid, dicarboxylic acid, tricarboxylic acid, and combinations thereof.

8. The aqueous formulation of claim 7 wherein the salt of the immune response modifier is a salt of an acid selected from the group consisting of hydrobromic acid, hydrochloric acid, lactic acid, glutamic acid, gluconic acid, tartaric acid, succinic acid and combinations thereof.

9. A method of treating allergic rhinitis, the method comprising applying the formulation of claim 1 into a nasal passage or a subject.

10. A method of treating a viral infection, the method comprising applying the formulation of claim 1 into a nasal passage of a subject.

11. A method of treating sinusitis, the method comprising applying the formulation of claim 1 into a nasal passage of a subject.

12. A method of treating asthma, the method comprising applying the formulation of claim 1 into the respiratory tract of a subject.

13. A method of desensitizing a subject to an antigen comprising:
    administering to the subject an IRM compound in the formulation of claim 1, after the subject has been sensitized to the antigen, in an amount effective to desensitize the subject to the antigen.

14. The aqueous formulation of claim 1 wherein the hydrophilic viscosity enhancing agent is selected from the group consisting of cellulose ethers, polysaccharide gums, acrylic acid polymers, and combinations thereof; and wherein the hydrophilic viscosity enhancing agent further comprises carboxylic acid groups and/or carboxylate groups.

15. An aqueous sprayable formulation for delivery of an immune response modifier to the nasal passage of a subject comprising:
    an immune response modifier, wherein the immune response modifier is N-{2-[4-amino-2-(ethoxymethyl)-1H-imidazo[4,5-c]quinolin-1-yl]-1,1-dimethylethyl}methanesulfonamide, or a pharmaceutically acceptable salt thereof;
    water; and
    a hydrophilic viscosity enhancing agent selected from the group consisting of cellulose ethers, polysaccharide gums, acrylic acid polymers, and combinations thereof;

with the proviso that the hydrophilic viscosity enhancing agent is not covalently bonded to the immune response modifier;

wherein the formulation is a solution at room temperature, has a viscosity of less than 100 cps at room temperature, and is contained in a nasal spray device.

16. A method for delivering an immune response modifier to a nasal passage of a subject, the method comprising:

selecting a formulation comprising:

an immune response modifier, wherein the immune response modifier is N-{2-[4-amino-2-(ethoxymethyl)-1H-imidazo[4,5-c]quinolin-1-yl]-1,1-dimethylethyl}methanesulfonamide, or a pharmaceutically acceptable salt thereof;

water; and a hydrophilic viscosity enhancing agent;

with the proviso that the hydrophilic viscosity enhancing agent is not covalently bonded to the immune response modifier;

wherein the formulation is a solution at room temperature and has a viscosity of less than 100 cps at room temperature, and is contained in a nasal spray device; and applying the selected formulation into a nasal passage of a subject.

* * * * *